US009719981B2

(12) United States Patent
Cosgrove

(10) Patent No.: US 9,719,981 B2
(45) Date of Patent: Aug. 1, 2017

(54) RAC1 INHIBITORS FOR THE TREATMENT OF ALPORT GLOMERULAR DISEASE

(71) Applicant: Father Flanagan's Boys' Home, Omaha, NE (US)

(72) Inventor: Dominic Cosgrove, Omaha, NE (US)

(73) Assignee: Father Flanagan's Boys' Home, Omaha, NE (US)

( * ) Notice: Subject to any disclaimer, the term of this patent is extended or adjusted under 35 U.S.C. 154(b) by 184 days.

(21) Appl. No.: 14/580,680

(22) Filed: Dec. 23, 2014

(65) Prior Publication Data

US 2015/0175695 A1 Jun. 25, 2015

Related U.S. Application Data

(63) Continuation-in-part of application No. PCT/US2013/032432, filed on Mar. 15, 2013.

(60) Provisional application No. 61/684,566, filed on Aug. 17, 2012, provisional application No. 61/764,389, filed on Feb. 13, 2013, provisional application No. 61/920,055, filed on Dec. 23, 2013, provisional application No. 62/079,988, filed on Nov. 14, 2014.

(51) Int. Cl.
| | |
|---|---|
| *A61K 39/395* | (2006.01) |
| *G01N 33/50* | (2006.01) |
| *A61K 31/506* | (2006.01) |
| *A61K 31/505* | (2006.01) |
| *A61K 31/5377* | (2006.01) |
| *G01N 33/68* | (2006.01) |
| *A61K 31/4025* | (2006.01) |

(52) U.S. Cl.
CPC ..... *G01N 33/5026* (2013.01); *A61K 31/4025* (2013.01); *A61K 31/505* (2013.01); *A61K 31/506* (2013.01); *A61K 31/5377* (2013.01); *A61K 39/395* (2013.01); *G01N 33/5044* (2013.01); *G01N 33/6893* (2013.01); *G01N 2500/10* (2013.01); *G01N 2800/347* (2013.01); *G01N 2800/50* (2013.01)

(58) Field of Classification Search
CPC ........... A61K 31/506; G01N 2800/347; C07K 16/00–16/468
See application file for complete search history.

(56) References Cited

U.S. PATENT DOCUMENTS

| 5,644,065 A | 7/1997 | Benoist et al. |
|---|---|---|
| 6,492,325 B1 | 12/2002 | Cosgrove |
| 7,348,002 B2 | 3/2008 | Cosgrove |
| 7,662,382 B2 | 2/2010 | Cosgrove |
| 2004/0186083 A1 | 9/2004 | McMahon et al. |
| 2011/0212083 A1 | 9/2011 | Reiser |
| 2011/0236397 A1 | 9/2011 | Reiser et al. |
| 2013/0216547 A1* | 8/2013 | Morton .................. C07K 16/26 424/139.1 |

FOREIGN PATENT DOCUMENTS

| EP | 0406628 B1 * | 11/1994 |
|---|---|---|
| WO | WO 2014/028059 A1 | 2/2014 |

OTHER PUBLICATIONS

Gross et al., Kidney Int'l 2009; 76:599-603.*
Gross et al., Kidney Int'l 2003; 63:438-446.*
Jain et al., Am. J. Pathol. 2012; 180(6):2309-20.*
Nishida et al., Am. J. Physiol Gastrointest Liver Physiol. 2006; 290:G1041-50.*
Abrahamson et al., "Laminin-1 reexpression in Alport mouse glomerular basement membranes," *Kidney Int.*, 2003; 63:826-834.
Abrahamson et al., "Laminin Compensation in Collagen α3(IV) Knockout (Alport) Glomeruli Contributes to Permeability Defects," *J Am Soc Nephrol.*, 2007; 18:2465-2472.
Abrahamson, "Steps on the Alport path to proteinuria," *Kidney International*, 2016, 90:242-244.
Andrews et al., "Gelatinase B (MMP-9) Is Not Essential in the Normal Kidney and Does Not Influence Progression of Renal Disease in a Mouse Model of Alport Syndrome," *Am J Pathol.*, 2000; 157(1):303-311.
Aumailley et al., "A simplified laminin nomenclature," *Matrix Biology*, 2005; 24:326-332.
Babu et al., "Mechanism of Stretch-Induced Activation of the Mechanotransducer Zyxin in Vascular Cells," *Science Signaling*, 2012; 5(254):ra91.
Baleato et al., "Deletion of Cd151 Results in a Strain-Dependent Glomerular Disease Due to Severe Alterations of the Glomerular Basement Membrane," *Am J Pathol.*, 2008; 173(4):927-937.
Barker et al., "Identification of mutations in the COL4A5 collagen gene in Alport syndrome," *Science*, Jun. 1990; 248(4960):1224-7.
Beg et al., "IκB interacts with the nuclear localization sequences of the subunits of NF-κB: a mechanism for cytoplasmic retention," *Genes Dev.*, 1992; 6:1899-1913.
Boffa et al., "Regression of renal vascular fibrosis by endothelin receptor antagonism," *Hypertension*, Feb. 2001; 37(2):490-496.
Boor et al., "Treatment targets in renal fibrosis," *Nephrol Dial Transplant.*, Aug. 2007; 22(12):3391-3407.
Bossy et al., "Characterization of the integrin α8 subunit: a new integrin β1-associated subunit, which is prominently expressed on axons and on cells in contact with basal laminae in chick embryos," *EMBO J.*, 1991; 10(9):2375-2385.

(Continued)

*Primary Examiner* — Jessica H Roark
(74) *Attorney, Agent, or Firm* — Mueting, Raasch & Gebhardt, P.A.

(57) ABSTRACT

The present invention provides methods of treating Alport syndrome in a subject by the administration of an agent that can block the activation of RAC1/CDC42 members of the rho family of small GTPases. Such agents include, but are not limited to, the endothelin receptor antagonists such as bosentan and letairis and neutralizing antibodies to endothelin-1. Such administration prevents invasion of the glomerular capillary tufts by mesangial lamellipodial/filopodial processes, blocks mesangial process invasion abrogates the deposition of laminin 211 in the GBM, and prevents the activation of maladaptive expression of proteins known to contribute to glomerular disease progression.

12 Claims, 31 Drawing Sheets

(56) References Cited

OTHER PUBLICATIONS

Bottero et al., "Monitoring NF-κB Transactivation Potential Via Real-Time PCR Quantification of I-κB-α Gene Expression," *Molecular Diagnosis*, 2003; 7(3-4):187-194.
Bursten et al., "Mesangial cell activation by bacterial endotoxin. Induction of rapid cytoskeletal reorganization and gene expression," *Am J Pathol.*, 1991; 139(2):371-382.
Cattaruzza et al., "Shear Stress Insensitivity of Endothelial Nitric Oxide Synthase Expression as a Genetic Risk Factor for Coronary Heart Disease," *Circ Res.*, 2004; 95(8):841-847.
Chandi et al., "The Rac/Cdc42 guanine nucleotide exchange factor β₁Pix enhances mastoparan-activated G$_i$-dependent pathway in mast cells," *Biochem Biophys Res Commun*, 2004; 317(2):384-389.
Chandi et al., Endothelin 1 Induces β₁Pix Translocation and Cdc42 Activation via Protein Kinase A-dependent Pathway, *J. Biol. Chem.*, 2005; 280(1):578-584.
Chandi et al., "Endothelin 1 stimulates beta1Pix-dependent activation of Cdc42 through the G(salpha) pathway," *Exp. Biol. Med.*, Jun. 2006; 231(6):761-5.
Chen et al., "Osteopontin increases migration and MMP-9 up-regulation via αvβ3 integrin, FAK, ERK, and NF-κB-dependent pathway in human chondrosarcoma cells," *J Cell Physiol.*, 2009; 221:98-108.
Choe et al., "Wnt-Dependent Epithelial Transitions Drive Pharyngeal Pouch Formation," *Dev Cell*, 2013; 24(3):296-309.
Cosgrove, Dominic "Molecular Aspects of Alport Renal Disease Progression," Grant Abstract, Grant No. 5R01-DK055000-12. National Institutes of Health. Project dates Apr. 15, 1999 to Aug. 31, 2014 [retrieved on Sep. 23, 2016]. Retrieved from the Internet:<URL:https://projectreporter.nih.gov/project_info_description.cfm?aid=8534087&icde=31224167>; 2 pgs.
Cosgrove et al., "Collagen COL4A3 knockout: a mouse model for autosomal Alport syndrome," *Genes Dev*, 1996; 10(23):2981-2992.
Cosgrove et al., "Integrin α1β1 and Transforming Growth Factor-β1 Play Distinct Roles in Alport Glomerular Pathogenesis and Serve as Dual Targets for Metabolic Therapy," *Am. J. Pathol.*, 2000; 157(5):1649-1659.
Cosgrove et al., "Integrin α1β1 Regulates Matrix Metalloproteinases via P38 Mitogen-Activated Protein Kinase in Mesangial Cells: Implications for Alport Syndrome," *Am. J. Pathol.*, 2008; 172(3):761-773.
Cosgrove et al., "Collagen IV diseases: a focus on the glomerular basement membrane in Alport syndrome," *Matrix Biol.* Epub ahead of print Aug. 27, 2016. DOI: 10.1016/j.matbio.2016.08.005.
Crean et al., "Connective tissue growth factor [CTGF]/CCN2 stimulates mesangial cell migration through integrated dissolution of focal adhesion complexes and activation of cell polarization," *The FASEB Journal*, 2004; 18(13):1541-1543.
Daniel et al., "Transgelin is a marker of repopulating mesangial cells after injury and promotes their proliferation and migration," *Lab Invest*, 2012; 92(6):812-826.
Deinhardt et al. "Neuronal Growth Cone Retraction Relies on Proneurotrophin Receptor Signaling Through Rac," *Sci Signal.*, 2011; 4(202):ra82.
Delimont et al., "Laminin β2-Mediated Focal Adhesion Kinase Activation Triggers Alport Glomerular Pathogenesis," *PLOS One*, 2014; 9(6):e99083; 14 pgs.
Dennis et al., "Collagen XIII Induced in Vascular Endothelium Mediates α1β1 Integrin-Dependent Transmigration of Monocytes in Renal Fibrosis," *Am J Pathol.*, 2010; 177:2527-2540.
Dufek et al., "Endothelin A receptor activation on mesangial cells initiates Alport glomerular disease," *Kidney International*, 2016; 90(2):300-310.
Durvasula et al., "Mechanical strain increases SPARC levels in podocytes: implications for glomerulosclerosis," *Am J Physiol Renal Physiol.*, 2005; 289:F577-F584.
Edlund et al., "Transforming Growth Factor-β-induced Mobilization of Actin Cytoskeleton Requires Signaling by Small GTPases Cdc42 and RhoA," *Mol. Bio. Cell*, 2002; 13:902-914.

Ehrig et al., "Merosin, a tissue-specific basement membrane protein, is a laminin-like protein," *Proc. Natl. Acad. Sci.*, May 1990; 87:3264-3268.
Etienne-Manneville et al., "Integrin-Mediated Activation of Cdc42 Controls Cell Polarity in Migrating Astrocytes through PKCζ," *Cell*, 2001; 106:489-498.
European Search Report and Search Opinion for European patent application No. 13829878.1, Mar. 21, 2016; 9 pages.
Ferri et al., "Virtual Screening Approach for the Identification of New Rac1 Inhibitors," *J. Med. Chem.*, 2009; 52(14):4087-4090.
Fessler et al., "Lipid Rafts Regulate Lipopolysaccharide-induced Activation of Cdc42 and Inflammatory Functions of the Human Neutrophil," *J Biol Chem*, 2004; 279(38):39989-39998.
Fischer et al., "Abnormal expression of glomerular basement membrane laminins in membranous glomerulonephritis," *Nephrol Dial Transplant*, 2000; 15:1956-1964.
Frampton, "Ambrisentan," *Am J Cardiovasc Drugs*, Aug. 2011; 11(4):215-226.
Gao et al., "Trp$^{56}$ of Rac1 Specifies Interaction with a Subset of Guanine Nucleotide Exchange Factors," *J Biol Chem*, 2001; 276(50):47530-47541.
Gao et al., "Rational design and characterization of a Rac GRPase-specific small molecule inhibitor," *Proc. Natl. Acad. Sci.*, May 2004; 101(20):7618-7623.
Gardner et al., "Deletion of Integrin α1 by Homologous Recombination Permits Normal Murine Development but Gives Rise to a Specific Deficit in Cell Adhesion," *Developmental Biology*, 1996; 175:301-313.
Gunwar et al., "Glomerular Basement Membrane," *J. Biol. Chem.*, 1998; 273(15):8767-8775.
Hartner et al., "α8 Integrin in glomerular mesangial cells and in experimental glomerulonephritis," *Kidney Int.*, 1999; 56:1468-1480.
Harvey et al., "Role of distinct type IV collagen networks in glomerular development and function," *Kidney Int.*, 1998; 54:1857-1866.
Helbling-Leclerc et al., "Mutations in the laminin α2-chain gene (LAMA2) cause merosin-deficient congenital muscular dystrophy," *Nat. Genet.*, 1995; 11:216-218.
Hernández et al., "Novel Inhibitors of Rac1 in Metastatic Breast Cancer," *Puerto Rico Health Sciences Journal*, Dec. 2010; 29(4):348-356.
Hishikawa et al., "Pressure Enhances Endothelin-1 Release From Cultured Human Endothelial Cells," *Hypertension*, 1995; 25(3):449-452.
Hocher et al., "Endothelial-1 Transgenic Mice Develop Glomerulosclerosis, Interstitial Fibrosis, and Renal Cysts but Not Hypertension," *J Clin Invest.*, 1997; 99(6):1380-1389.
Horikoshi et al., "Abnormal Distribution of Mesangium-Specific Laminin in Glomeruli of Patients with Idiopathic Membranous Nephropathy," *Nephron*, 1999; 81(3):284-288.
Huang et al., "RhoB links PDGF signaling to cell migration by coordinating activation and localization of Cdc42 and Rac," *J. Cell Biochem.*, 2011; 112(6):1572-1584. NIH Public Access Author Manuscript available online Jun. 1, 2012.
International Preliminary Report on Patentability for PCT Application No. PCT/US2013/032432 dated Feb. 17, 2015; 6 pgs.
International Search Report and Written Opinion for PCT Application No. PCT/US2013/032432 dated Jun. 5, 2013; 8 pgs.
Just et al., "Dual constrictor and dilator actions of ET$_B$ receptors in the rat renal microcirculation: interactions with ET$_A$ receptors," *Am J Physiol Renal Physiol.*, 2004; 265(4):F660-F668.
Just et al., "NO and NO-independent mechanisms mediate ET$_B$ receptor buffering of ET-1-induced renal vasoconstriction in the rat," *Am J Physiol Regul Integr Comp Physiol.*, 2005; 288(5):R1168-R1177.
Kalluri et al., "Isoform Switching of Type IV Collagen is Developmentally Arrested in X-Linked Alport Syndrome Leading to Increased Susceptibility of Renal Basement Membranes to Endoproteolysis," *J. Clin. Invest.*, 1997; 99(10):2470-2478.
Kalluri et al., "Assembly of Type IV Collagen," *J. Biol. Chem.*, 2000; 275(17):12719-12724.

(56) References Cited

OTHER PUBLICATIONS

Kamentetsky et al., "Analysis of the Glomerular Basement Membrane in Images of Renal Biopsies Using the Split-and-Merge Method: A Pilot Study," *Journal of Digital Imaging*, 2010; 23(4):463-474.

Kashtan et al., "Alport syndrome," *Kidney Int.*, 1996; 50(5):1445-1463.

Kashtan et al., "Chronology of renal scarring in males with Alport syndrome," *Pediatric Nephrology*, May 1998; 12(4):269-274.

Kashtan et al., "Abnormal Glomerular Basement Membrane Laminins in Murine, Canine, and Human Alport Syndrome: Aberrant Laminin α2 Deposition Is Species Independent," *J. Am. Soc. Nephrol.*, 2001; 12:252-260.

Kisanuki et al., "Low Blood Pressure in Endothelial Cell-Specific Endothelin 1 Knockout Mice," *Hypertension*, 2010; 56(1):121-128.

Klabunde, "Endothelin," Cardiovascular Physiology Concepts website, 2009. Retrieved on Sep. 15, 2016 from the Internet: <URL:http://www.cvphysiology.com/Blood%20Flow/BF012.htm>; 2 pgs.

Kleppel et al., "Evidence for Separate Networks of Classical and Novel Basement Membrane Collagen," *J. Biol. Chem.*, 1992; 267(6):4137-4142.

Kodani et al., "GM130-dependent Control of Cdc42 Activity at the Golgi Regulates Centrosome Organization," *Mol Biol Cell*, 2009; 20(4):1192-1200.

Koepke et al., "Nephroprotective effect of the HMG-CoA-reductase inhibitor cerivastatin in a mouse model of progressive renal fibrosis in Alport syndrome," *Nephrol Dial Transplant*, 2007; 22:1062-1069.

Kruegel et al., "Alport syndrome-insights from basic and clinical research," *Nature Reviews Nephrology*, 2013; 9:170-178.

Kurihara et al., Aortic Arch Malformations and Ventricular Septal Defect in Mice Deficient in Endothelin-1, *J Clin Invest.*, 1995; 96(1):293-300.

Leivo et al., "Merosin, a protein specific for basement membranes of Schwann cells, striated muscle, and trophoblast, is expressed late in nerve and muscle development," *Proc. Natl. Acad. Sci.*, Mar. 1988; 85:1544-1548.

Li et al., "A Calcium-dependent Tyrosine Kinase Splice Variant in Human Monocytes," *J Biol Chem.*, 1998; 273(16):9361-9364.

Ma et al., "Inhibition of Podocyte FAK Protects against Proteinuria and Foot Process Effacement," *J Am Soc Nephrol.*, 2010; 21:1145-1156.

Madrid et al., "The Formin INF2 Regulates Basolateral-to-Apical Transcytosis and Lumen Formation in Association with Cdc42 and MAL2," *Dev Cell*, 2010; 18(5):814-27.

Marsden et al., "Endothelial cell biology in relation to current concepts of vessel wall structure and function," *J Am Soc Nephrol.*, Jan. 1991; 1(7):931-948.

Marsden et al., "Regulated expression of endothelin 1 in glomerular capillary endothelial cells," *Am J Physiol.*, Jul. 1991, 261 (1):F117-F125.

Meehan et al., "Biomechanical strain causes maladaptive gene regulation, contributing to Alport glomerular disease," *Kidney Int.*, 2009; 76:968-976.

Meehan et al., "Endothelin-1 mediated induction of extracellular matrix genes in strial marginal cells underlies strial pathology in Alport mice," *Hearing Research*, 2016, 341:100-108.

Miner et al., "The Laminin α Chains: Expression, Developmental Transitions, and Chromosomal Locations of α1-5, Identification of Heterotrimeric Laminins 8-11, and Cloning of a Novel α3 Isoform," *J. Cell. Biol.*, 1997; 137(3):685-701.

Mochizuki et al., "Identification of mutations in the α3(IV) and α4(IV) collagen genes in autosomal recessive Alport syndrome," *Nature Genetics*, 1994; 8:77-82.

Nagase, "Substrate Specificity of MMPs," *Cancer Drug Discovery and Development: Matrix Metalloproteinase Inhibitors in Cancer Therapy*, Totowa, NJ 2001, pp. 39-66.

Neuhofer et al., "Role of endothelin and endothelin receptor antagonists in renal disease," European Journal of Clinical Investigation, 2006; 36(Suppl. 3):78-88.

Nishiuchi et al., "Potentiation of the ligand-binding activity of integrin α1β1 via association with tetraspanin CD151," *Proc Natl Acad Sci USA*, 2005;102(6):1939-44.

Nobes et al., "Rho, Rac, and Cdc42 GTPases Regulate the Assembly of Multimolecular Focal Complexes Associated with Actin Stress Fibers, Lamellipodia, and Filopodia," *Cell*, 1995; 81:53-62.

Oh et al., "Syndecan-1 enhances the endometrial cancer invasion by modulating matrix metalloproteinase-9 expression through nuclear factor κB," *Gynecol Oncol.*, 2009; 114:509-515.

Osmani et al., "Cdc42 localization and cell polarity depend on membrane traffic," *J Cell Biol.*, 2010; 191(7):1261-9.

Ostrow et al., "Stretch-Induced Endothelin-1 Production by Astrocytes," *J Cardiovasc Pharmacol.*, 2000; 36(Suppl. 1):S274-S277.

Ostrow et al., "Stretch induced endothelin-1 secretion by adult rat astrocytes involves calcium influx via stretch-activated ion channels (SACs)," *Biochem Biophys Res Commun.*, 2011; 410(1):81-86. NIH Public Access Author Manuscript available online Jun. 24, 2012.

Parsons, "Focal adhesion kinase: the first ten years," *J Cell Sci.*, 2003; 116(8):1409-1416.

Parsons et al., "Focal Adhesion Kinase: Targeting Adhesion Signaling Pathways for Therapeutic Intervention," *Clinical Cancer Research*, 2008; 14:627-632.

Patton et al., "Distribution and Function of Laminins in the Neuromuscular System of Developing, Adult, and Mutant Mice," *J Cell Biol.*, 1997; 139:1507-1521.

Pelish et al., "Secramine inhibits Cdc42-dependent functions in cells and Cdc42 activation in vitro," *Nature Chemical Biology*, 2006; 2:39-46.

Person et al., "Modulation of Mesangial Cell Migration by Extracellular Matrix Components," *Am J Pathol*; 1988; 133(3):609-614.

Rao et al., "Role for Macrophage Metalloelastase in Glomerular Basement Membrane Damage Associated with Alport Syndrome," *Am. J. Pathol.*, 2006; 169(1):32-46.

Ritz et al., "Endothelin Receptor Antagonists in Proteinuric Renal Disease: Every Rose Has Its Thorn," *J Am. Soc. Nephrol.*, 2010; 21(3):392-394.

Rubin et al., "Bosentan Therapy for Pulmonary Arterial Hypertension," *N. Engl. J. Med.*, 2002; 346(12):896-903.

Sachs et al., "Kidney failure in mice lacking the tetraspanin CD151," *J Cell Biol.*, 2006; 175(1):33-39.

Sachs et al., "Blood pressure influences end-stage renal disease of Cd151 knockout mice," *J. Clin. Invest.*, 2012; 122(1):348-358.

Sampson et al., "Global Gene Expression Analysis Reveals a Role for the $\alpha_1$ Integrin in Renal Pathogenesis," *J Biol Chem.*, 2001; 276(36):34182-34188.

Sanchez-Lopez et al., "Role of Zinc-binding- and Hemopexin Domain-encoded Sequences in the Substrate Specificity of Collagenase and Stromelysin-2 as Revealed by Chimeric Proteins," *J Biol Chem.*, 1993; 268(10):7238-7247.

Sanlioglu et al., "Lipopolysaccharide Induces Rac1-dependent Reactive Oxygen Species Formation and Coordinates Tumor Necrosis Factor-α Secretion through IKK Regulation of NF-κB," *J Biol Chem*, 2001; 276(32):30188-98.

Sayers et al., "Role for transforming growth factor-β1 in Alport renal disease progression," *Kidney International*, 1999; 56:1662-1673.

Schlöndorff et al., "The Mesangial Cell Revisited: No Cell Is an Island," *J Am Soc Nephrol.*, 2009; 20:1179-87.

Schnapp et al., "Sequence and tissue distribution of the human integrin $\alpha_8$ subunit: a $\beta_1$-associated α subunit expressed in smooth muscle cells," *J Cell Sci.*, 1995; 108:537-544.

Shutes et al., "Specificity and Mechanism of Action of EHT 1864, a Novel Small Molecule Inhibitor of Rac Family Small GTPases," *J. Biol. Chem.*, 2007; 282:32666-35678.

Simonson et al., "Endothelin-1 Stimulates Contraction of Rat Glomerular Mesangial Cells and Potentiates α-Adrenergic-mediated Cyclic Adenosine Monophosphate Accumulation," *J Clin Invest.*, 1990; 85(3):790-797.

(56) References Cited

OTHER PUBLICATIONS

Sorokin, "Endothelin signaling and actions in the renal mesangium," *Contrib. Nephrol.*, 2011; 172:50-62.

St. John et al., "Glomerular endothelial cells and podocytes jointly synthesize laminin-1 and -11 chains," *Kidney International*, 2001; 60:1037-1046.

Surviladze et al., "A Potent and Selective Inhibitor of Cdc42 GTPase," Probe Reports from the NIH Molecular Libraries Program [Internet], National Center for Biotechnology Information, 2010; 27 pgs.

Takeda et al., "Deletion of tetraspanin Cd151 results in decreased pathologic angiogenesis in vivo and in vitro," *Blood*, 2007; 109(4):1524-1532.

"Tracleer Bonsentan Tablets" datasheet. Actelion Pharmaceuticals US, Inc., South San Francisco, CA, 2012; 6 pgs.

Tseng et al., "FAK activation is required for TNF-α-induced IL-6 production in myoblasts," *J Cell Physiol.*, 2010; 223:389-396.

Van Slambrouck et al., "Activation of the FAK-src molecular scaffolds and p130Cas-JNK signaling cascades by α1-integrins during colon cancer cell invasion," *Int J Oncol.*, 2007; 31:1501-1508.

Vatter et al., "Ambrisentan, a Non-peptide Endothelin Receptor Antagonist," *Cardiovascular Drug Reviews*, 2006; 24(1):63-76.

Vincente-Manzanares et al., "Integrins in cell migration—the actin connection," *J. Cell Sci.*, 2009; 122(2):199-206.

Vincente-Manzanares et al., "Integrins in cell migration—the actin connection," Author Correction, *J. Cell Sci.*, 2009; 122:1473.

Wendel et al., "Distribution of Endothelin Receptor Subtypes $ET_A$ and $ET_B$ in the Rat Kidney," *J Histochem Cytochem.*, 2006; 54(11):1193-1203.

Wójtowicz et al., "Zyxin Mediation of Stretch-Induced Gene Expression in Human Endothelial Cells," *Circ Res.*, 2010; 107(7):898-902.

Wyss et al., "Biophysical properties of normal and diseased renal glomeruli," *Am. J. Physiol. Cell Physiol.*, 2011; 300:C397-C405.

Yamamoto et al., "Endothelin B Receptor-like Immunoreactivity in Podocytes of the Rat Kidney," *Arch Histol Cytol.*, 2002; 65(3):245-250.

Yeh et al., "The antioxidative effect of bone morphogenetic protein-7 against high glucose-induced oxidative stress in mesangial cells," *Biochem Biophys Res Commun.*, 2009; 382(2):292-297.

Zallocchi et al., "α1β1 Integrin/Rac1-Dependent Mesangial Invasion of Glomerular Capillaries in Alport Syndrome," *Am. J. Pathol.*, 2013; 183(4):1269-1280.

Zamudio-Meza et al., "Cross-talk between Rac1 and Cdc42 GTPases regulates formation of filopodia required for dengue virus type-2 entry into HMEC-1 cells," *J Gen Virol.*, 2009; 90:2902-2911.

Zeisberg et al., "Stage-Specific Action of Matrix Metalloproteinases Influences Progressive Hereditary Kidney Disease," *PLOS Medicine*, 2006; 3(4), el00:535-546.

Zeng et al., "Role of Focal Adhesion Kinase and Phosphatidylinositol 3'-Kinase in Integrin Fibronectin Receptor-Mediated, Matrix Metalloproeinase-1-Dependent Invasion by Metastatic Prostate Cancer Cells," *Cancer Res.*, 2006; 66(16):8091-8099.

Licht et al., "ETB-Receptor Blockade Reduces Tubulointerstitial Fibrosis Caused by Chronic Proteinuria in COL4A3 Knockout Mice," Poster No. TH-PO471, Presented at American Society of Nephrology Renal Week, Nov. 8-13, 2005, Philadelphia, PA. *J Am Soc Nephrol*, 2005; 16:220A.

\* cited by examiner

RAC1 INHIBITORS FOR THE TREATMENT OF ALPORT GLOMERULAR DISEASE

CONTINUING APPLICATION DATA

This application is a continuation-in-part of International Application No. PCT/US2013/032432, filed Mar. 15, 2013, which claims the benefit of U.S. Provisional Application Ser. No. 61/684,566, filed Aug. 17, 2012, and U.S. Provisional Application Ser. No. 61/764,389, filed Feb. 13, 2013, all of which is incorporated by reference herein. This application also claims priority to U.S. Provisional Application No. 61/920,055, filed Dec. 23, 2013, and U.S. Provisional Application No. 62/079,988, filed Nov. 14, 2014, each of which is incorporated by reference herein.

GOVERNMENT FUNDING

This invention was made with government support under Grant No. R01-DK55000 awarded by the National Institutes of Health. The Government has certain rights in the invention.

BACKGROUND

Alport syndrome (also referred to as hereditary nephritis) is a genetic disorder characterized by abnormalities in the basement membranes of the glomerulus (leading to hematuria, glomerulosclerosis, and end-stage kidney disease (ESRD)), cochlea (causing deafness), and eye (resulting in lenticonus and perimacular flecks). Alport syndrome is a primary basement membrane disorder caused by mutations in the collagen type IV COL4A3, COL4A4, or COL4A5 genes. Mutations in any of these genes prevent the proper production or assembly of the type IV collagen network, which is an important structural component of basement membranes in the kidney, inner ear, and eye. Basement membranes are thin, sheet-like structures that separate and support cells in many tissues. The abnormalities of type IV collagen in kidney glomerular basement membranes leads to irregular thickening and thinning and splitting of these basement membranes, causing gradual scarring (fibrosis) of the kidneys. Alport Syndrome has a delayed onset and causes progressive kidney damage. The glomeruli and other normal kidney structures such as tubules are gradually replaced by scar tissue, leading to kidney failure. Hearing loss and an abnormality in the shape of the lens called anterior lenticonus are other important features of Alport Syndrome. People with anterior lenticonus may have problems with their vision and may develop cataracts. The prevalence of Alport syndrome is estimated at approximately 1 in 5,000 births and it is estimated that the syndrome accounts for approximately 2.1 percent of pediatric patients with ESRD. Currently there is no specific treatment for Alport Syndrome; treatments are symptomatic. Patients are advised on how to manage the complications of kidney failure and the proteinuria that develops is often treated with ACE inhibitors. Once kidney failure has developed, patients are given dialysis or can benefit from a kidney transplant, although this can cause problems. The body may reject the new kidney as it contains normal type IV collagen, which may be recognized as foreign by the immune system. Thus there is a need for improved therapeutic approaches for the treatment of Alport syndrome.

SUMMARY OF INVENTION

The present invention includes a method of treating Alport syndrome in a subject, the method including administering an effective amount of a RAC1 inhibitor and/or a CDC42 inhibitor.

The present invention includes a method of preventing glomerular disease progression in a subject diagnosed with Alport syndrome, the method including administering an effective amount of a RAC1 inhibitor and/or a CDC42 inhibitor.

The present invention includes a method of treating glomerulonephritis in a subject, the method including administering an effective amount of a RAC1 inhibitor and/or a CDC42 inhibitor.

The present invention includes a method of treating kidney injury due to biomechanical strain in Alport syndrome, the method including administering an effective amount of a RAC1 inhibitor and/or a CDC42 inhibitor.

The present invention includes a method of inhibiting deposition of laminin 211 in the glomerular basement membrane (GBM) in a subject, the method including administering an effective amount of a RAC1 inhibitor and/or a CDC42 inhibitor.

The present invention includes a method of inhibiting mesangial cell process invasion of the glomerular capillary loops in a kidney of a subject, the method including administering an effective amount of a RAC1 inhibitor and/or a CDC42 inhibitor.

The present invention includes a method of inhibiting Alport glomerular pathogenesis in a subject; the method including: determining that the subject is at risk for developing Alport glomerular disease; and administering an effective amount of a RAC1 inhibitor and/or a CDC42 inhibitor to the subject. In some aspects, the determination that the subject is at risk for developing Alport glomerular disease is determined by family medical history, genetic testing, immunodiagnostic skin biopsy testing, and/or molecular diagnostic marker testing. In some aspects, the determination that the subject is at risk for developing Alport glomerular disease is made prior to the onset of proteinuria in the subject.

The present invention includes a method of treating or preventing one or more aspects of a sensory loss and/or hearing loss associated with Alport syndrome in a subject, the method including administering an effective amount of a RAC1 inhibitor and/or a CDC42 inhibitor.

In some aspects of the methods of the present invention, the administration of an effective amount of a RAC1 inhibitor and/or a CDC42 inhibitor is initiated prior to the onset of proteinuria in the subject.

In some aspects of the methods of the present invention, the RAC1 inhibitor and/or a CDC42 inhibitor is an agent that blocks activation of the endothelin type I receptor and/or the endothelin type II receptor.

In some aspects of the methods of the present invention, the RAC1 inhibitor and/or a CDC42 inhibitor is an endothelin (ET) receptor antagonist. In some aspects, the endothelin (ET) receptor antagonist is a dual antagonist of both the $ET_A$ receptor and $ET_B$ receptor. In some aspects, the endothelin (ET) receptor antagonist is an antagonist of the $ET_A$ receptor. In some aspects, the endothelin (ET) receptor antagonist is an antagonist of the $ET_B$ receptor. In some aspects of the methods of the present invention, the endothelin (ET) receptor antagonist is bosentan or a derivative thereof.

In some aspects of the methods of the present invention, the RAC1 inhibitor and/or a CDC42 inhibitor is bosentan or a derivative thereof. In some aspects of the methods of the present invention, the RAC1 inhibitor and/or a CDC42 inhibitor is letairius or a derivative thereof. In some aspects of the methods of the present invention, the RAC1 inhibitor is NSC23766 or a derivative thereof.

In some aspects of the methods of the present invention, the endothelin (ET) receptor antagonist is letairius or a derivative thereof.

In some aspects of the methods of the present invention, the endothelin (ET) receptor antagonist is NSC23766 or a derivative thereof.

In some aspects of the methods of the present invention, the RAC1 and/or CDC42 inhibitor includes macitentan (OPSUMIT®) or a derivative thereof.

In some aspects of the methods of the present invention, the RAC1 and/or CDC42 inhibitor includes altrasentan or a derivative thereof.

In some aspects of the methods of the present invention, the RAC1 and/or CDC42 inhibitor includes an antibody that specifically binds to endothelin-1 or a derivative thereof. In some aspects, the antibody against endothelin-1 or derivative thereof neutralizes one or more functions of endothelin-1.

In some aspects of the methods of the present invention, the RAC1 and/or CDC42 inhibitor includes an antibody that specifically binds an endothelin receptor or a derivative thereof. In some aspects, the antibody against an endothelin receptor or derivative thereof neutralizes one or more functions of an endothelin receptor.

In some aspects of the methods of the present invention, the RAC1 and/or CDC42 inhibitor includes an antibody that specifically binds the endothelin A receptor or a derivative thereof. In some aspects, the antibody against endothelin A receptor or derivative thereof neutralizes one or more functions of endothelin A receptor.

The present invention also includes an in vitro bioassay for identifying agents effective for treating Alport syndrome in a subject, preventing glomerular disease progression in a subject diagnosed with Alport syndrome, treating glomerulonephritis in a subject, treating kidney injury due to biomechanical strain in Alport syndrome, inhibiting deposition of laminin 211 in the glomerular basement membrane (GBM) in a subject, inhibiting mesangial cell process invasion of the glomerular capillary loop in a kidney of a subject, and/or inhibiting Alport glomerular pathogenesis in a subject.

BRIEF DESCRIPTION OF THE FIGURES

FIGS. 2G-2L show localization of laminin $\alpha 5$ (a GBM marker) and integrin $\alpha 8$. Note circumferential co-localization of laminin $\alpha 2$ and integrin $\alpha 8$ in the Alport glomerulus in D-F, and the co-localization of integrin $\alpha 8$ and laminin $\alpha 5$ in J-L indicating invasion of the glomerular capillary tufts with mesangial processes.

DETAILED DESCRIPTION OF ILLUSTRATIVE EMBODIMENTS

Figure 1:
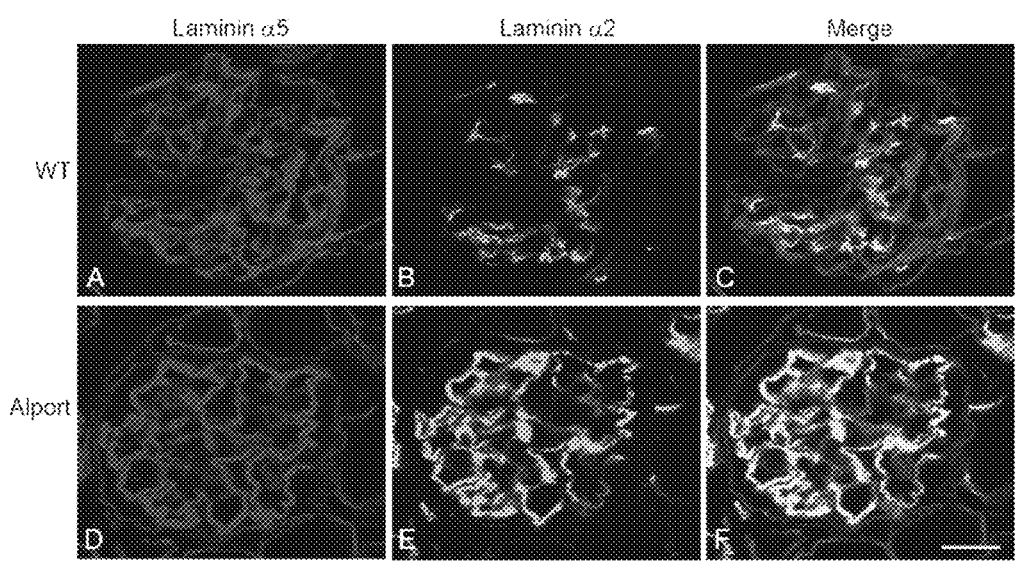
FIG. 1. Laminin 211 localizes to the glomerular basement membrane (GBM) in Alport glomeruli. Dual immunofluorescence immunostaining was performed on wild type (A-C) and Alport (D-F) glomeruli from 7 week 129 Sv mice. Glomerular basement membranes were labeled with labeled with anti-laminin $\alpha 5$ antibodies (A and D). Anti-laminin $\alpha 2$ immunostaining is shown in B and E. Note the irregular deposits of laminin 211 in the Alport GBM, especially in the thickened regions of the GBM (overlapping staining in D and E). Anti-laminin $\alpha 2$ immunostaining is not observed in the GBM of wild type mice (note the absence of overlapping immunostaining in A and B).

Alport syndrome (also referred to as hereditary nephritis) is a genetic disorder characterized by abnormalities in the basement membranes of the glomerulus (leading to hematuria, glomerulosclerosis, and end-stage kidney disease (ESRD)), cochlea (causing hearing loss), and eye (resulting in lenticonus and perimacular flecks). Alport syndrome is a primary basement membrane disorder caused by mutations in the collagen type IV COL4A3, COL4A4, or COL4A5 genes. Mutations in any of these genes prevent the proper production or assembly of the type IV collagen network, which is an important structural component of basement membranes in the kidney, inner ear, and eye. Basement membranes are thin, sheet-like structures that separate and support cells in many tissues. The abnormalities of type IV collagen in kidney basement membranes leads to irregular thickening and thinning and splitting of basement membranes, causing gradual scarring of the kidneys. Alport Syndrome causes progressive kidney damage. The glomeruli and other normal kidney structures such as tubules are gradually replaced by scar tissue, leading to kidney failure. Deafness and an abnormality in the shape of the lens called anterior lenticonus are other important features of Alport Syndrome. People with anterior lenticonus may have problems with their vision and may develop cataracts. The prevalence of Alport syndrome is estimated at approximately 1 in 5,000 births and it is estimated that the syndrome accounts for approximately 2.1 percent of pediatric patients with ESRD. Currently there is no specific treatment for Alport Syndrome; treatments are symptomatic. Patients are advised on how to manage the complications of kidney failure and the proteinuria that develops is often treated with ACE inhibitors. Once kidney failure has developed, patients are given dialysis or can benefit from a kidney transplant, although this can cause problems. The body may reject the new kidney as it contains normal type IV collagen, which may be recognized as foreign by the immune system. Thus there is a need for improved therapeutic agents for the treatment of individuals with Alport syndrome, especially for the treatment of presymptomatic individuals, before the onset of proteinuria.

Alport syndrome is characterized by delayed onset progressive glomerulonephritis associated with sensorineural hearing loss and retinal flecks (Kashtan and Michael, 1996, *Kidney Int*; 50(5):1445-1463). The most common form (80%) is X-linked and caused by mutations in the type IV collagen COL4A5 gene (Barker et al., 1990, *Science*; 8; 248(4960):1224-7). The two autosomal forms of the disease account for the remaining 20% of Alport patients, and result from mutations in the COL4A3 and COL4A4 genes (Mochizuki et al., 1994, *Nat Genet*; 8(1):77-81). The α3(IV), α4(IV) and α5(IV) proteins form a heterotrimer and is assembled into a subepithelial network in the glomerular basement membrane that is physically and biochemically distinct from a subendothelial type IV collagen network comprised of α1(IV) and α2(IV) heterotrimers (Kleppel et al., 1992, *J Biol Chem*; 267(6):4137-4142). Mutations in any one of the three type IV collagen genes that cause Alport syndrome results in the absence of all three proteins in the GBM due to an obligatory association to form functional heterotrimers (Kalluri and Cosgrove, 2000, *J Biol Chem*; 275(17):12719-12724). Thus, the net result for all genetic forms of Alport syndrome is the absence of the α3(IV) α4(IV) α5(IV) subepithelial collagen network, resulting in a GBM type IV collagen network comprised only of α1(IV) and α2(IV) heterotrimers.

This change in basement membrane composition does not result in immediate pathology. The GBM appears to function adequately for the first few years of life and sometimes past the first decade (Kashtan et al., 1998, *Pediatr Nephrol*; 12(4):269-27). This delayed onset predicts a triggering mechanism for glomerular disease initiation and a theoretical window for therapeutic intervention that may arrest or significantly ameliorate Alport renal disease in its earliest stages.

Alport syndrome may result from mutations in type IV collagen COL4A3, COL4A4, or COL4A5 genes. These mutations may be either autosomal recessive (mutations in either COL4A3 or COL4A4 genes (Mochizuki et al., 1994, *Nat Genet*; 8(1):77-81)) or X-linked (mutations in COL4A5 (Barker et al., 1990, *Science*; 248(4960):1224-7)). Mutations in any of these genes results in the absence of all three collagens (α3(IV), α4(IV), and α5(IV) in the GBM type IV collagen network due to an obligatory association to form heterotrimers. The result is a thinner and less cross-linked GBM collagen network resulting in delayed onset progressive glomerulonephritis. Until the observations of the present invention, the molecular trigger for disease onset was unknown.

Alport syndrome is also known as congenital hereditary hematuria, hematuria-nephropathy-deafness syndrome, hematuric hereditary nephritis, hemorrhagic familial nephritis, hemorrhagic hereditary nephritis, hereditary familial congenital hemorrhagic nephritis, hereditary hematuria syndrome, hereditary interstitial pyelonephritis, and hereditary nephritis.

With the present invention, it has been discovered that the pathology of Alport glomerular disease is based on an entirely different mechanism. Alport syndrome results from a change in the type IV collagen composition in the glomerular basement membrane where the normally present α3(IV)/α4(IV)/α5(IV) network is absent, and thus the type IV collagen composition of the GBM is thus comprised of a network of α1(IV) and α2(IV) chains. This latter network is known to contain fewer interchain crosslinks and is thinner than a normal GBM, and thus we expect that the GBM would have a greater elasticity under normal glomerular pressures, which are very high relative to blood pressures in most tissues in the body. This enhanced elasticity imparts unusually high biomechanical stresses on the cells that adhere to the GBM, including podocytes, endothelial cells, and mesangial cells. Consistent with this, Alport mice made hypertensive by including salt in the drinking water showed higher proteinuria, elevated levels of glomerular matrix metalloproteinase expression, and accelerated damage to the GBM (Meehan et al., 2009, *Kidney Int*; 76(9):968-76).

The present invention shows that hypertensive mice express much higher levels of endothelin-1, specifically in the endothelial cells, and endothelin A receptors, specifically on mesangial cells. Activation of endothelin receptors on glomerular mesangial cells, specifically endothelin receptor A, has been linked to activation of the rho-GTPases, Rac1 and CDC42 (reviewed in Sorokin, 2011, *Contrib Nephrol*; 172:50-62). Classically, CDC42 activation results in filopodial formation in cultured cells. The present examples show crosstalk between Rac1 and CDC42 in cultured mesangial cells and demonstrated mesangial filopodial invasion of the glomerular capillary tufts, and showed that blocking RAC 1 ameliorated this invasion, restored GBM ultrastructural pathology, and reduced pathologic gene expression in the glomeruli from Alport mice (see Example 1 and Zallocchi et al., 2013, *Am J Pathol*; 183(4):1269-802013). These invading mesangial filopodia secrete laminin 211, which activates focal adhesion kinase (FAK) on glomerular podocytes. Blocking FAK reduces pathologic expression of MMPs and ameliorates GBM damage. The present examples also show that endothelin blockade also reduces pathologic expression of MMPs as well.

Collectively, the present invention defines a mechanism whereby biomechanical strain induces expression of endothelin-1 in glomerular endothelial cells and endothelin A receptor on mesangial cells in Alport glomeruli. Endothelin A activation leads to mesangial filopodial invasion of the glomerular capillary tufts. The filopodia deposit laminin 211, which activates FAK in podocytes, resulting in marked elevation of pro-pathologic genes including MMP-10 and MMP-12. These MMPs proteolytic degrade the GBM driving glomerulosclerosis. Blocking endothelin receptor activation using Bosentan or activation of cytoskeletal dynamics using Rac1 inhibitors arrests the invasion of the capillary tufts by mesangial filopodia. This activation of mesangial filopodia invasion has never been described before and is thus a new etiology.

The present invention provides for the administration of an endothelin receptor antagonist to prevent the damage induced by biomechanical strain and to prevent the initiation of disease pathology. The present invention provides new methods of use for endothelin receptor antagonists. Blocking the activation of this process with an endothelin receptor antagonist such as bosentan represents a new use for such drugs.

The present invention includes methods of treating Alport syndrome in a subject by the administration of a RAC1 inhibitor and/or a CDC42 inhibitor. The administration of a RAC1 inhibitor and/or a CDC42 inhibitor may result in, for example, inhibiting migration of mesangial cells, inhibiting irregular deposition of mesangial laminin 211 in the GBM, inhibiting invasion of the capillary loops by mesangial cell processes, inhibiting mesangial filopodial invasion of the glomerular capillary tuft, and/or preventing, or slowing the onset of proteinuria.

The present invention includes methods of preventing, slowing, and/or managing glomerular disease progression in a subject diagnosed with Alport syndrome by the administration of a RAC1 inhibitor and/or a CDC42 inhibitor.

The present invention includes methods of treating glomerulonephritis associated with Alport syndrome in a subject by administering a RAC1 inhibitor and/or a CDC42 inhibitor.

The present invention includes methods of treating kidney injury due to biomechanical strain in Alport syndrome by administering a RAC1 inhibitor and/or a CDC42 inhibitor.

The present invention includes methods of inhibiting deposition of laminin 211 in the glomerular basement membrane (GBM) by administering a RAC1 inhibitor and/or a CDC42 inhibitor. The laminins are major proteins in the basal lamina, a layer of the basement membrane, a protein network foundation for most cells and organs. Laminins are heterotrimeric proteins that contain an α-chain, a β-chain, and a γ-chain, found in five, four, and three genetic variants, respectively. The laminin molecules are named according to their chain composition. Thus, laminin-511 contains α5, β1, and γ1 chains (Aumailley et al., 2005, *Matrix Biol.;* 24(5): 326-32). Fourteen other chain combinations have been identified in vivo. Laminin-211 (composed of α2, β1 and γ1 chains (Ehrig et al., 1991, *PNAS;* 87:3264-3268) is the main laminin isoform in skeletal muscle (Leivo and Engvall, 1988, *PNAS;* 85:1544-1588; and Patton, 1997, *J Cell Biol.;* 139:1507-1521) and identification of laminin α2 chain mutations in a severe form of congenital muscular dystrophy (merosin-deficient congenital muscular dystrophy; MDC1A) established the importance of laminin-211 for normal muscle function (Helbling-Leclerc et al., 1995, *Nat Genet;* 11:216-218). The present invention demonstrates for the first time, the role of the deposition of laminin 211 in the glomerular basement membrane (GBM) in the pathogenesis of Alport syndrome. Its role is to activate focal adhesion kinase in glomerular podocytes. As shown in the examples included herewith, laminin 211 mediates FAK activation in Alport podocytes and FAK inhibitors ameliorate Alport kidney disease. This demonstrates that laminin 211 in the GBM activates FAK on podocytes which results in propathologic changes in gene expression.

The present invention includes methods of inhibiting mesangial cell process invasion of the glomerular capillary loop of the kidney by administering a RAC1 inhibitor and/or a CDC42 inhibitor. RAC1 (also referred to herein as Rac1) is a member of the Rac subfamily (Rac1-Rac4) of the Rho family of GTPases. Members of this superfamily appear to regulate a diverse array of cellular events, including the control of cell growth, cytoskeletal reorganization, and the activation of protein kinases. Together with Rho (regulator of stress fibers) and Cdc42 (regulator of filopodia), Rac modulates the formation of focal adhesion (FA) complexes; membrane ruffles and lamellipodia that contribute to important cell functions related to cell attachment and movement.

The methods of the present invention may be used for the presymptomatic treatment of individuals, with the administration of a RAC1 inhibitor and/or a CDC42 inhibitor beginning after the determination or diagnosis of Alport syndrome, prior to the onset of symptoms, such as for, example, proteinuria. The diagnosis of Alport syndrome in an individual may be made, for example, by family medical history, genetic testing, immunodiagnostic skin biopsy testing, and/or molecular diagnostic marker testing. Methods of the present invention may also include one or more steps of obtaining a diagnosis of Alport syndrome by the use of one or more such diagnostic means.

A RAC1 inhibitor or a CDC42 inhibitor may block the activation of RAC1/CDC42 members of the rho family of small GTPases. Any of a wide variety of RAC1 inhibitors or CDC42 inhibitors may be used with the methods of the present invention. In some aspects, a RAC1 inhibitor or a CDC42 inhibitor may include a small molecule inhibitor. In some aspects, a RAC1 inhibitor or a CDC42 inhibitor may include a biologic, such as, for example, an antibody or receptor polypeptide.

In some aspects, a RAC1 inhibitor or a CDC42 inhibitor is an antibody that binds to endothelin-1 and/or the endothelin A receptor. In some aspects, such an antibody inhibits, blocks, and/or neutralizes one or more functions of endothelin-1 and/or the endothelin A receptor. Antibodies that bind to endothelin-1 or the endothelin A receptor can be produced and characterized by any of a variety of means known to the skilled artisan. Likewise, antibodies that inhibit and/or neutralize one of more functions of endothelin-1 or the endothelin A receptor can also be produced and characterized by any of a variety of means known to the skilled artisan.

As will be understood by those in the art, the term "antibody" extend to all antibodies from all species, and antigen binding fragments thereof, including dimeric, trimeric and multimeric antibodies; bispecific antibodies; chimeric antibodies; human and humanized antibodies; recombinant and engineered antibodies, and fragments thereof. The term "antibody" is thus used to refer to any antibody-like molecule that has an antigen binding region, and this term includes antibody fragments such as, for example, Fab', Fab, F(ab')$_2$, single domain antibodies (DABs), Fv, scFv (single chain Fv), linear antibodies, diabodies, and the like. The techniques for preparing and using various antibody-based constructs and fragments are well known in the art.

In certain embodiments, the antibodies employed may be "humanized" antibodies. Humanized" antibodies are generally chimeric monoclonal antibodies from mouse, rat, or other non-human species, bearing human constant and/or variable region domains. Various humanized monoclonal antibodies for use in the present invention will be chimeric antibodies wherein at least a first antigen binding region, or complementarity determining region (CDR), of a mouse, rat or other non-human monoclonal antibody is operatively attached to, or "grafted" onto, a human antibody constant region or "framework." Humanized monoclonal antibodies for use herein may also be monoclonal antibodies from non-human species wherein one or more selected amino acids have been exchanged for amino acids more commonly observed in human antibodies. This can be readily achieved through the use of routine recombinant technology, particularly site-specific mutagenesis.

Entirely human antibodies may also be prepared and used in the present invention. Such human antibodies may be obtained from healthy subjects by simply obtaining a population of mixed peripheral blood lymphocytes from a human subject, including antigen-presenting and antibody-producing cells, and stimulating the cell population in vitro.

In some aspects, a RAC1 inhibitor or a CDC42 inhibitor may be a small molecule inhibitor. For example, a RAC1 inhibitor or a CDC42 inhibitor may include, but is not limited to, NSC23766 and derivatives thereof (Gao et al., 2004, *PNAS*; 101:7618-7623), EHT 1864 and derivatives thereof (Shutes et al., 2007, *J Biol Chem*; 282:35666-35678), W56 (Gao et al., 2001, *J Biol Chem*; 276:47530), F56 (Gao et al., 2001, *J Biol Chem*; 276:47530), and any of the RAC1 inhibitors described by Ferri et al. (*J Med Chem* 2009; 52(14):4087-90) and Hernandez et al. (*P R Health Sci J* 2010; 29(4):348-356). In some aspects of the methods described herein, a RAC1 inhibitor may be NSC23766 or a derivative thereof. Human CDC42 is a small GTPase of the Rho-subfamily, which regulates signaling pathways that control diverse cellular functions including cell morphology, migration, endocytosis and cell cycle progression.

Any of a wide variety of CDC42 inhibitors may be used with the methods described herein, including, but not limited to, secramine (Pelish et al., 2006, *Nat Chem Biol.*; 2(1):39-46), ML141 (Surviladze et al., "A Potent and Selective Inhibitor of Cdc42 GTPase," Probe Reports from the NIH Molecular Libraries Program [Internet], Bethesda (Md.): National Center for Biotechnology Information (US); 2010), or an endothelin receptor antagonist, such as, for example, bosentan, ambrisentan, or derivatives thereof.

In some aspects of the methods described herein, a RAC1 inhibitor or a CDC42 inhibitor may include an endothelin receptor antagonist. Such an endothelin receptor antagonist includes, but is not limited to, small molecule antagonists and biologics, such as for example, an antibody or receptor polypeptide.

Endothelin receptor antagonists include, for example, bosentan, a dual endothelin receptor antagonist, is currently indicated mainly for the treatment of pulmonary arterial hypertension (PAH) (see Rubin et al., 2002, *N Engl J Med*; 346(12): 896-903). In 2007, bosentan was also approved in the European Union for reducing the number of new digital ulcers in patients with systemic sclerosis and ongoing digital ulcer disease. It is also known by the trade name TRACLEER® (Actelion Pharmaceuticals US, Inc.), is designated chemically as 4-tert-butyl-N-[6-(2-hydroxy-ethoxy)-5-(2-methoxy-phenoxy)[2,2']-bipyrimidin-4-yl]-benzenesulfonamide monohydrate, has the chemical formula $C_{27}H_{31}N_5O_7S$, and the CAS Registry number 157212-55-0.

While bosentan has been used experimentally to treat diabetic nephropathy (Ritz and Wenzel, 2010, *J Am Soc Nephrol*; 21(3):392-4), the molecular basis for this use is that endothelin causes vasoconstriction through its activation of endothelin receptors, and thus blockade of these receptors results in vasodilation and a drop in blood pressure in the glomerulus, thus reducing proteinuria. Since these blocking agents are mechanistically distinct from angiotensin converting enzyme (ACE) inhibitors, it has been thought that a combination therapy could be quite beneficial; similar to the FDA approved use of Bosentan to treat pulmonary hypertension, which is also often employed in combination with ACE inhibitors.

Endothelin receptor antagonists include, for example, ambrisentan, an endothelin receptor antagonist selective for the type A endothelin receptor (ETA) (reviewed by Vatter and Seifert, 2006, *Cardiovasc Drug Rev*; 24(1):63-76), is currently indicated for the treatment of pulmonary arterial hypertension (PAH) (see Frampton, 2011, *Am J Cardiovascul Drugs*; 11(4):215-226). In the United States it is also known by the trade name LETARIS®, is also known as Volobris, and pulmonest, is designated chemically as (2S)-2-[(4,6-dimethylpyrimidin-2-yl)oxy]-3-methoxy-3,3-diphenylpropanoic acid, CAS 7036-94-1, and has the CAS Registry number 177036-94-1.

Endothelin receptor antagonists include, for example, macitentan (trade name OPSUMIT®; designated chemically as N-[5-(4-Bromophenyl)-6-[2-[(5-bromo-2-pyrimidinyl)oxy]ethoxy]-4-pyrimidinyl]-N'propylsulfamide), an orally available endothelin receptor antagonist (ERA) indicated for the treatment of pulmonary arterial hypertension.

Endothelin receptor antagonists include, for example, atrasentan (chemically designated as 2R,3R,4S)-4-(1,3-benzodioxol-5-yl)-1-[2-(dibutylamino)-2-oxoethyl]-2-(4-methoxyphenyl)pyrrolidine-3-carboxylic acid), an endothelin receptor antagonist selective for subtype A (ETA). While other drugs of this type (sitaxentan, ambrisentan) exploit the vasoconstrictive properties of endothelin and are mainly used for the treatment of pulmonary arterial hypertension, atrasentan blocks endothelin induced cell proliferation.

Endothelin receptor antagonists include, for example, sitaxentan (also known as TBC-11251 sodium salt, Thelin; chemically designated as N-(4-chloro-3-methyl-1,2-oxazol-5-yl)-2-[2-(6-methyl-2H-1,3-benzodioxol-5-yl)acetyl]thiophene-3-sulfonamide), a small molecule that blocks the action of endothelin (ET) on the endothelin-A (ETA) receptor selectively (by a factor of 6000 compared to the ETB). It is a sulfonamide class endothelin receptor antagonist (ERA). Endothelin receptor antagonists include, for example, darusentan, an endothelin-1 receptor A antagonist, chemically designated as (2S)-2-(4,6-Dimethoxypyrimidin-2-yl)oxy-3-methoxy-3,3-di(phenyl)propanoic acid).

In some aspects of the methods described herein, an endothelin receptor antagonist blocks CDC42 activation in glomerular mesangial cells. This is well established in cultured cells (Chadi and Sorokin, 2006, *Exp Biol Med*; 6:761). Three main kinds of ERAs are known: selective $ET_A$ receptor antagonists (sitaxentan, ambrisentan (LETAIRIS), atrasentan, BQ-123, zibotentan), which affect endothelin A receptors; dual antagonists (bosentan (TRACLEER), macitentan, tezosentan), which affect both endothelin A and B receptors; and selective $ET_B$ receptor antagonists (BQ-788 and A192621).

In some aspects of the methods described herein, an endothelin receptor antagonist is bosentan or a derivative thereof.

In some aspects of the methods described herein, an endothelin receptor antagonist is ambrisentan or a derivative thereof.

In some aspects of the methods described herein, an endothelin receptor antagonist is macitentan or a derivative thereof.

In some aspects of the methods described herein, an endothelin receptor antagonist is altrasentan or a derivative thereof.

With the present invention, a novel mechanism responsible for the pathology of Alport glomerular disease has been discovered. This mechanism, described in more detail in the examples included herewith, includes one or more of the following:

changes in basement membrane type IV collagen composition result in distension of the capillary in response to normal blood pressure;

biomechanical strain results in activation of endothelin-1 expression in glomerular endothelial cells;

binding of endothelin-1 to endothelin receptors on mesangial cells activates the rho GTPases Rac1 and CDC42, resulting in the activation of actin cytoskeletal dynamics and the invasion of the glomerular capillaries by mesangial filopodia;

mesangial filopodia secrete mesangial matrix molecules into the GBM microenvironment, including laminin 211;

laminin 211 directly activates focal adhesion kinase on glomerular podocytes;

FAK activation results in NFkappaB-mediated induction of MMPs and pro-inflammatory cytokines that degrade the GBM, progressively resulting in classical Alport ultrastructural abnormalities (irregular thickening and thinning with multi-lamination) and proteinuria; and/or progressive glomerular disease results in interstitial fibrosis.

With this newly gained understanding of the mechanism responsible for the pathology of Alport glomerular disease, agents that block one or more of the mechanisms listed above may be used to prevent and/or treat the symptoms of Alport disease.

The present invention also includes in vitro and in vivo assays for the screening and identification of agents with endothelin receptor antagonist activity for use in the treatment of Alport syndrome. Such assays include, but are not limited to, any one of the various cell culture and animal model systems described herein. In vitro assays include, for example, cultured primary mesangial cells (for example, as described by Cosgrove et al., 2008, *Am J Pathol;* 172: 761-773), cultured podocytes, and conditional immortalized glomerular epithelial cells (GEC's) (Rao et al., 2006, *Am J Pathol;* 169: 32-46). The treatment (contacting) of such cultured cells with endothelin-1 induces the formation of drebrin-positive filopodial microspikes. Potential endothelin receptor antagonist activity of an agent may be identified and/or assayed by pretreatment (contacting) of the cells with the agent, with a potential endothelin receptor antagonist inhibiting, reducing and/or blocking the formation of microspikes in comparison to cells not pretreated with the agent. Any such assay may also include appropriate controls, including, but not limited to negative and/or positive controls.

With the method of the present invention, one or more additional therapeutic modalities may be administered along with one or more agents of the present disclosure. In some aspects of the present invention, the administration of agents of the present disclosure may allow for the effectiveness of a lower dosage of other therapeutic modalities when compared to the administration of the other therapeutic modalities alone, providing relief from the toxicity observed with the administration of higher doses of the other modalities. One or more additional therapeutic agents may be administered before, after, and/or coincident to the administration of agents of the present disclosure. Agents of the present disclosure and additional therapeutic agents may be administered separately or as part of a mixture of cocktail. As used herein, an additional therapeutic agent may include, for example, an agent whose use for the treatment of Alport syndrome, kidney disease, kidney failure, and/or proteinuria is known to the skilled artisan. For example, an angiotensin-converting enzyme (ACE) inhibitor, such as ramipril or analapril, may be administered.

As used herein "treating" or "treatment" can include therapeutic and/or prophylactic treatments. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis.

The agents of the present disclosure can be administered by any suitable means including, but not limited to, for example, oral, rectal, nasal, topical (including transdermal, aerosol, buccal and sublingual), vaginal, parenteral (including subcutaneous, intramuscular, intravenous and intradermal), intravesical, or injection. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants.

The present invention includes compositions of one or more of the inhibitors described herein. A composition may also include, for example, buffering agents to help to maintain the pH in an acceptable range or preservatives to retard microbial growth. Such compositions may also include a pharmaceutically acceptable carrier. As used herein, the term "pharmaceutically acceptable carrier" refers to one or more compatible solid or liquid filler, diluents or encapsulating substances which are suitable for administration to a human or other vertebrate animal. The compositions of the present disclosure are formulated in pharmaceutical preparations in a variety of forms adapted to the chosen route of administration.

Therapeutically effective concentrations and amounts may be determined for each application herein empirically by testing the compounds in known in vitro and in vivo systems, such as those described herein, dosages for humans or other animals may then be extrapolated therefrom. With the methods of the present disclosure, the efficacy of the administration of one or more agents may be assessed by any of a variety of parameters known in the art.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

An agent of the present disclosure may be administered at once, or may be divided into a number of smaller doses to be administered at intervals of time. For example, an agent of the present disclosure may be administered twice a day, three times a day, four times a day, or more. For example an agent of the present disclosure may be administered every other day, every third day, once a week, every two weeks, or once a month. In some applications, an agent of the present disclosure may be administered continuously, for example by a controlled release formulation or a pump.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some applications, administration on agent of the present disclosure may be short term or long term. In some aspects, long term administration may be for weeks, months, years, or decades.

In some applications, administration on agent of the present disclosure may be at a dosage similar to the accepted dosage for previously known applications. For example, an agent such as bosentan or a derivative thereof may be administered at a dosage similar to the dosage that is administered for the treatment of pulmonary arterial hypertension (PAH) at about 62.5, about 125, or about 250 mg/day. For example, an agent such as ambrisentan or a derivative thereof may be administered at a dosage similar to the dosage that is administered for the treatment of pulmonary arterial hypertension (PAH) at about 2.5 to about 10 mg/day.

In some applications, administration on agent of the present disclosure may be at a dosage considerably less than the accepted dosage for previously known applications. For example, dosage may be ½, ⅕, 1/10, 1/20, 1/50, 1/100, 1/250, 1/500, 1/1,000, 1/2,500, 1/5,000, 1/10,000, 1/25,000, 1/50,000, or 1/100,000 the accepted dosage.

For example, an agent, such as, for example, bosentan or ambrisentan, or a derivative thereof, may be administered at a dosage of about 0.1, about 0.2, about 0.25, about 0.4, about 0.5, about 0.6, about 0.7, about 0.75, about 0.8, about 0.9, about 1 ug daily, about 1.5, about 2, about 2.5, about 3, about 4, about 5, about 6, about 7, about 7.5, about 8, about 9, about 10, about 15, about 20, about 25, about 30, about 40, about 50, about 60, about 70, about 75, about 80, about 90, or about 100 microgram (μg) daily, or any range thereof.

For example, an agent, such as, for example, bosentan or ambrisentan, or a derivative thereof, may be administered at a dosage of about 0.1, about 0.2, about 0.25, about 0.3, about 0.4, about 0.5, about 0.6, about 0.7, about 0.75, about 0.8, about 0.9, about 1, about 1.25, about 2, about 2.5, about 3, about 4, about 5, about 6.25, about 10, about 12.5, about 20, about 25, about 30, about 40, about 50, or about 62.5 mg daily, or any range thereof.

For example, an agent, such as, for example, bosentan or ambrisentan, or a derivative thereof, may be administered at a dosage of less than about 0.1, about 0.2, about 0.25, about 0.4, about 0.5, about 0.6, about 0.7, about 0.75, about 0.8, about 0.9, about 1 ug daily, about 1.5, about 2, about 2.5, about 3, about 4, about 5, about 6, about 7, about 7.5, about 8, about 9, about 10, about 15, about 20, about 25, about 30, about 40, about 50, about 60, about 70, about 75, about 80, about 90, or about 100 microgram (μg) daily.

For example, an agent, such as, for example, bosentan or ambrisentan, or a derivative thereof, may be administered at a dosage of less than about 0.1, about 0.2, about 0.25, about 0.3, about 0.4, about 0.5, about 0.6, about 0.7, about 0.75, about 0.8, about 0.9, about 1, about 1.25, about 2, about 2.5, about 3, about 4, about 5, about 6.25, about 10, about 12.5, about 20, about 25, about 30, about 40, about 50, or about 62.5 mg daily.

In some applications, administration on agent of the present disclosure may be at a dosage greater than the accepted dosage for previously known applications for the treatment of pulmonary arterial hypertension (PAH). For example, an agent, such as, for example, bosentan or a derivative thereof may be administered at a dosage of about 250 mg/day or more, about 300 mg/day or more, about 450 mg/day or more, about 500 mg/day or more, about 600 mg/day or more, about 750 mg/day or more, about 1000 mg/day or more, about 1500 mg/day or more, about 2000 mg/day or more, or about 2500 mg/day or more. For example, an agent such as ambrisentan or a derivative thereof may be administered at a dosage of about 10 mg/day or more, about 12 mg/day or more, about 15 mg/day or more, about 20 mg/day or more, about 25 mg/day or more, about 30 mg/day or more, about 40 mg/day or more, about 50 mg/day or more, or about 100 mg/day or more.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

As used herein, the term "subject" includes, but is not limited to, humans and non-human vertebrates. In preferred embodiments, a subject is a mammal, particularly a human. A subject may be an individual. A subject may be an "individual," "patient," or "host." In some aspects, a subject is an individual diagnosed with Alport syndrome. Diagnosis may be by any of a variety of means, including, but not limited to, family history, clinical presentation, pathological determination, and/or genetic testing. Such as subject may be a male or a female. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject.

As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Also herein, the recitations of numerical ranges by endpoints include all numbers subsumed within that range (e.g., 1 to 5 includes 1, 1.5, 2, 2.75, 3, 3.80, 4, 5, etc.).

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

For any method disclosed herein that includes discrete steps, the steps may be conducted in any feasible order. And, as appropriate, any combination of two or more steps may be conducted simultaneously.

All headings are for the convenience of the reader and should not be used to limit the meaning of the text that follows the heading, unless so specified.

The above discussion of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein.

EXAMPLES

Example 1

α1β1 Integrin-Mediated Rac1/CDC42-Dependent Mesangial Process Invasion of Glomerular Capillary Tufts in Alport Syndrome With this example, a comparative analysis of glomerular disease progression in Alport mice and CD151 knockout mice revealed a progressive irregular deposition of mesangial laminin 211 in the GBM. Co-localization studies showed that the mesangial integrin α8β1 also progressively accumulates in the capillary loops of both models as well as in human Alport glomeruli, indicating an invasion of the capillary loops by mesangial cell processes. L-NAME salt-induced hypertension accelerated mesangial cell process invasion and laminin 211 accumulation, suggesting biomechanical strain plays a role in this mechanism. Cultured mesangial cells showed reduced migratory potential when treated with either integrin linked kinase inhibitor, Rac1 inhibitors, CDC42 inhibitors, or by deletion of integrin α1. Biomechanical stretching of cultured mesangial cells induced pro-migratory cytokines TGF-β1 and CTGF. Treatment of Alport mice with a Rac1 inhibitor reduced mesangial cell process invasion of the glomerular capillary tuft. Laminin α2-deficient Alport mice show reduced mesangial process invasion, and laminin α2-null cells show reduced migratory potential, indicating a central role for mesangial laminins in progression of Alport glomerular pathogenesis. Collectively, these findings predict a role for biomechanical insult in the induction of mesangial cell process invasion of the glomerular capillary tuft leading to the irregular deposition of mesangial laminin 211 as an initiation mechanism of Alport glomerular pathology.

The activation of genes encoding GBM matrix molecules, matrix metalloproteinases (MMPs), and proinflammatory cytokines have all been linked to the progression of Alport glomerular disease. These, however, are events that occur after the onset of proteinuria therefore downstream of disease initiation events (Sayers et al., 1999, *Kidney Int;* 56(5):1662-1673; Cosgrove et al., 2000, *Am J Pathol;* 157(5):1649-59; Rao et al., 2006, *Am J Pathol;* 169(1):32-46; Zeisberg et al., 2006, *PLoS Medicine;* 3(4), e100; and Cosgrove et al., 2008, *Am J Pathol;* 172(3):761-7737-11). Consistent with this notion, experiments aimed at blocking these pathways have offered only limited therapeutic benefit in mouse models for Alport syndrome (Cosgrove et al., 2000, *Am J Pathol;* 157(5):1649-59; Rao et al., 2006, *Am J Pathol;* 169(1):32-46; Zeisberg et al., 2006, *PLoS Medicine;* 3(4), e100; and Koepke et al., 2007, *Nephrol Dial Transplant;* 22(4):1062-9). One of the earliest events is the appearance of an irregular deposition of laminin 211 in the GBM of Alport mice (Cosgrove et al., 2000, *Am J Pathol;* 157(5):1649-59), an observation confirmed in both Alport dogs and human patients with the disease (Kashtan et al., 2001, *J Am Soc Nephrol;* 12:252-60). This laminin is normally found only in the mesangium of the glomerulus, and is not expressed in the GBM at any stage of embryonic development (Miner et al., 1997, *J Cell Biol;* 137(3):685-701). Indeed several other mesangial matrix proteins appear in the GBM of Alport mice, including laminin 111 and fibronectin (Cosgrove et al., 1996, *Genes Dev;* 10(23): 2981-2992; and St John and Abrahamson, 2001, *Kidney Int;* 60(3):1037-1046).

In the Alport glomerulus, the podocytes are exposed to GBM that has an embryonic type IV collagen composition (Kalluri et al., 1997, *J Clin Invest;* 99(10):2470-2478; and Harvey et al., 1998, *Kidney Int;* 54(6):1857-1866). This could result in altered cell signaling that may trigger the onset of the disease. It has been proposed this type of mechanism may account for the reactivation of laminin 111 expression in podocytes (Abrahamson et al., 2003, *Kidney Int;* 63:826-34), a laminin found in the GBM during development (Miner et al., 1997, J Cell Biol; 137(3):685-701). Since the α1(IV)/α2 (IV) collagen network contains significantly fewer interchain disulfide crosslinks (Gunwar et al., 1998, *J Biol Chem;* 273(15):8767-75), and since the Alport GBM is thinner than normal (Kamenetsky et al., 2010, *J Digital Imaging;* 23:463-474) the Alport GBM is likely to be more elastic, resulting in elevated biomechanical strain on the glomerular cells at their points of contact the GBM. Consistent with this, glomeruli from Alport mice have been shown to have elevated deformability relative to wild type glomeruli (Wyss et al., 2011, *Am J Physiol Cell Physiol;* 300:C397-C405), and salt-induced hypertension has been shown to accelerate glomerular disease progression in Alport mice (Meehan et al., 2009, *Kidney Int;* 76:968-976).

This example shows that deletion of laminin 211 in Alport mice ameliorates the mesangial process invasion of the glomerular capillary loops in Alport mice, demonstrating for the first time a functional role for GBM laminin 211 in Alport glomerular pathogenesis. The cellular origin of GBM laminin 211 has not been previously determined. This example shows that the source of GBM laminin 211 in Alport GBM is mesangial cell processes, which are invading the capillary tufts. Salt-mediated hypertension exacerbates this mesangial process invasion. A knockout mouse for the integrin α3β1 co-receptor CD151, which results in reduced adhesion of podocytes pedicles to GBM laminin 521, also develops mesangial process invasion of the capillary loops with GBM deposition of laminin 211, demonstrating the same phenotype for a completely unrelated component of the capillary structural barrier. The CD151 knockout mouse model also shows accelerated glomerular disease progression in response to hypertension (Sachs et al., 2012, *J Clin Invest;* 122(1):348-58). Mesangial cell culture studies show that biomechanical stretching induces pro-migratory cytokines TGF-β1 and CTGF, both known to be induced in Alport glomeruli (Sayers et al., 1999, *Kidney Int;* 56(5):1662-1673; and Koepke et al., 2007, *Nephrol Dial Transplant;* 22(4): 1062-9) Inhibitor studies indicate that migration is mediated through α1β1 integrin signaling through the Rho GTPases RAC1 and CDC42. Consistent with this, α1 integrin deletion in Alport mice was previously shown to ameliorate glomerular disease progression and slow the accumulation of laminin 211 in Alport GBM (Cosgrove et al., 2000, *Am J Pathol;* 157(5):1649-59). This example shows that mesangial process invasion of the capillary loops is ameliorated in α1 integrin null Alport mice. These data define a surprising role for biomechanical strain mediated-induction of mesangial cell process invasion as a key aspect of Alport glomerular disease initiation, and identify novel therapeutic targets to blocking this process.

Results

Figure 2:
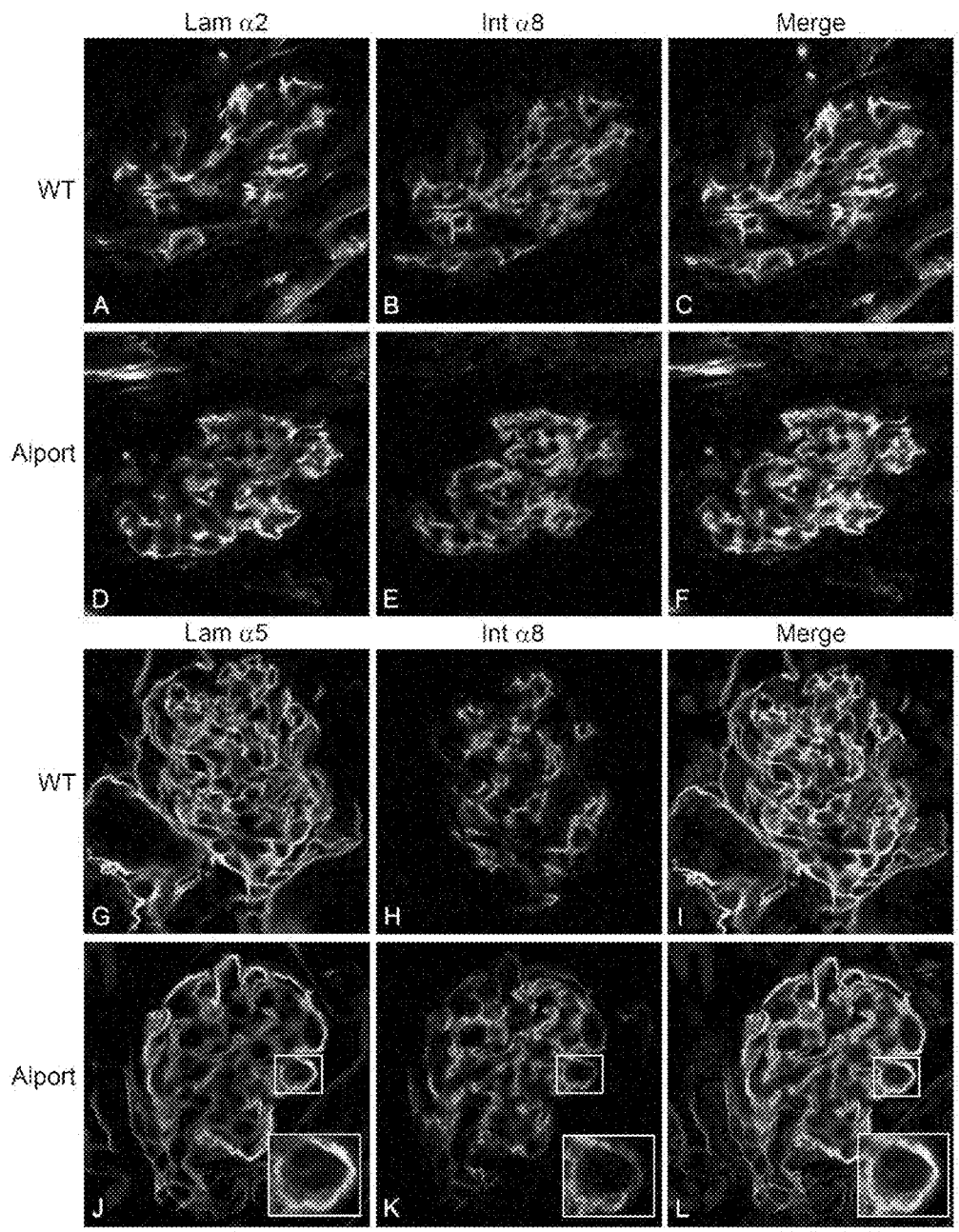
FIG. 2. Mesangial processes invade the capillary loops of Alport glomeruli where they co-localize with laminin 211 deposits. Dual immunofluorescence immunostaining was performed on wild type or Alport kidney sections from 7 week old 129 Sv mice. A-F show localization of laminin $\alpha 2$ and integrin $\alpha 8$ (a mesangial cell marker), and G-L

GBM laminin 211 in Alport mice is of mesangial origin. In the glomerulus, laminin 211 is normally found only in the mesangial matrix. FIG. 1 (A-C) demonstrates mesangial distribution of laminin 211 in wild type mice, which is distinct from the glomerular basement membrane (collagen α3(IV)). In Alport glomeruli, FIG. 1 (D-F) demonstrates the irregular distribution of laminin 211 in the GBM which appears to accumulate preferentially in irregularly thickened regions of the GBM (here the GBM is marked by immunostaining with antibodies specific for laminin α5). The cellular source of the GBM laminin 211 has never been determined. Dual immunofluorescence labeling with antibodies against laminin α2 and integrin α8 show mesangial specific immunostaining in wild type glomeruli (FIG. 2 (A-C)), as reported previously (Hartner et al., 1999, *Kidney Int;* 56(4):1468-80). In Alport glomeruli (at 7 weeks of age) immunostaining for both laminin α2 and integrin α8 appears to have spread into the capillary loops consistent with a mesangial cell process invasion of the capillary loops (FIG. 2 (D-F)). Dual immunofluorescence immunostaining using the basement membrane marker laminin α5 with the mesangial marker integrin α8 confirms that integrin α8 immunostaining, while absent from the GBM in wild type mice (FIG. 2 (G-I)), is clearly present in most of the GBM of Alport mice (FIG. 2 (J-L)). Collectively these data indicate that GBM laminin 211 arises from a mesangial cell process invasion of the capillary loops, and thus is of mesangial cell origin.

Figure 3:
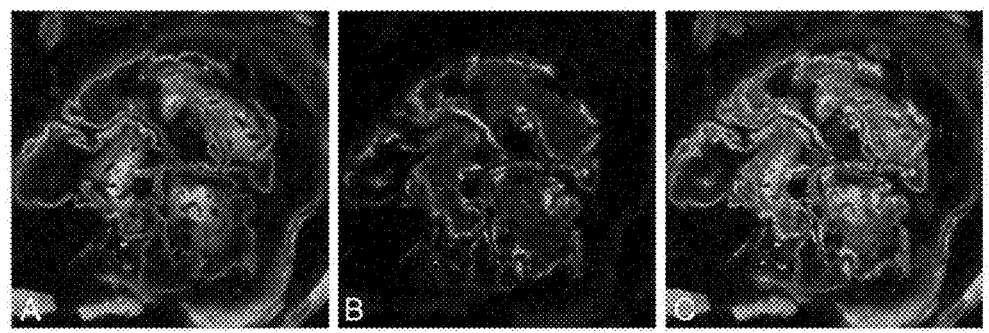
FIG. 3. Mesangial processes invade the capillary loops of human Alport glomeruli where they co-localize with laminin 511. Cryosections from human Alport kidneys were stained with antibodies specific for laminin $\alpha 5$ (A) and integrin $\alpha 8$ (B). The integrin $\alpha 8$-specific mesangial processes localize adjacent to the laminin $\alpha 5$-positive GBM, consistent with mesangial process invasion. C represents a merging of A and B.

To determine the relevance of this observation to human Alport syndrome cryosections from human Alport necropsy kidney sections were stained with antibodies specific for integrin α8 and laminin α5. The results in FIG. 3 (A-C) show that mesangial processes are clearly present adjacent to the laminin α5-immunopisitive GBM in the human specimen.

Figure 4:
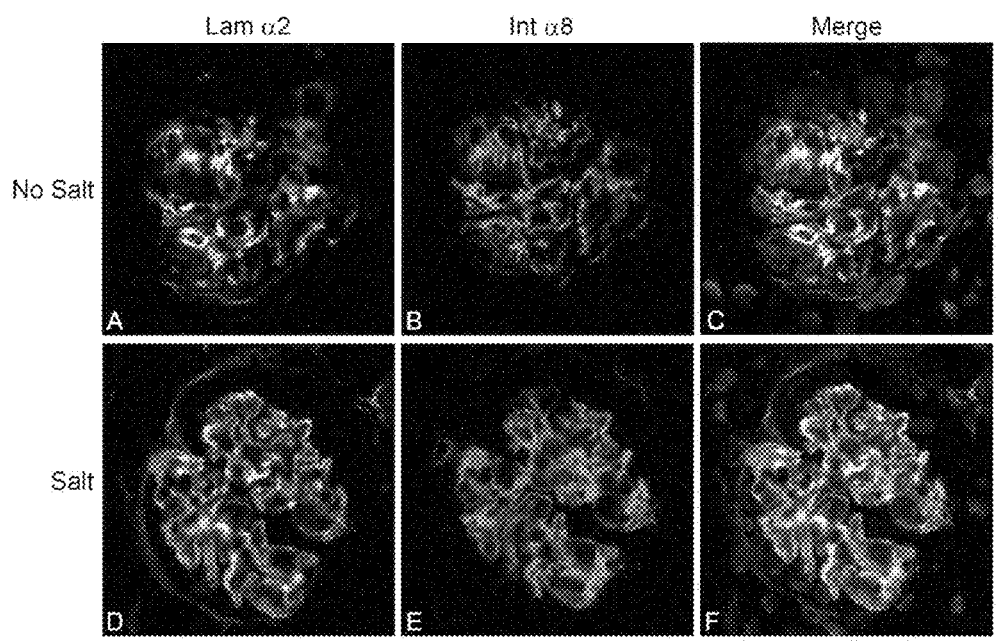
FIG. 4. Hypertension exacerbates mesangial invasion of the glomerular capillary tufts in Alport mice. The X-linked Alport mouse model (on the C57 Bl/6 background) was made hypertensive by providing L-NAME salts in the drinking water from 5 weeks to 10 weeks of age. Control Alport mice were given normal drinking water. Glomeruli were analyzed by dual immunofluorescence immunostaining using antibodies against either laminin $\alpha 2$ (A and D) or integrin $\alpha 8$ (B and E). Panels C and F represent a merging of results with laminin $\alpha 2$ and integrin $\alpha 8$ staining. Extensive mesangial process invasion of the capillary tuft is observed in the glomeruli from the salt-treated mice relative to the mice given normal drinking water.

Mesangial process invasion of the capillary loops is exacerbated by elevated biomechanical strain. An earlier report demonstrated that hypertension exacerbated the progression of Alport glomerular disease (Meehan et al., 2009, *Kidney Int;* 76:968-976). Hypertension accelerated several aspects of glomerular disease progression including proteinuria and induction of matrix metalloproteinases. The accumulation of GBM laminin 211 was also accelerated. As shown in FIG. 4 (A-F), salt-induced hypertension clearly accelerates the inundation of the glomerular capillary loops by mesangial processes as evidenced by the presence of integrin α8 immunopositivity in the GBM (FIG. 4(D-F)).

Figure 5:
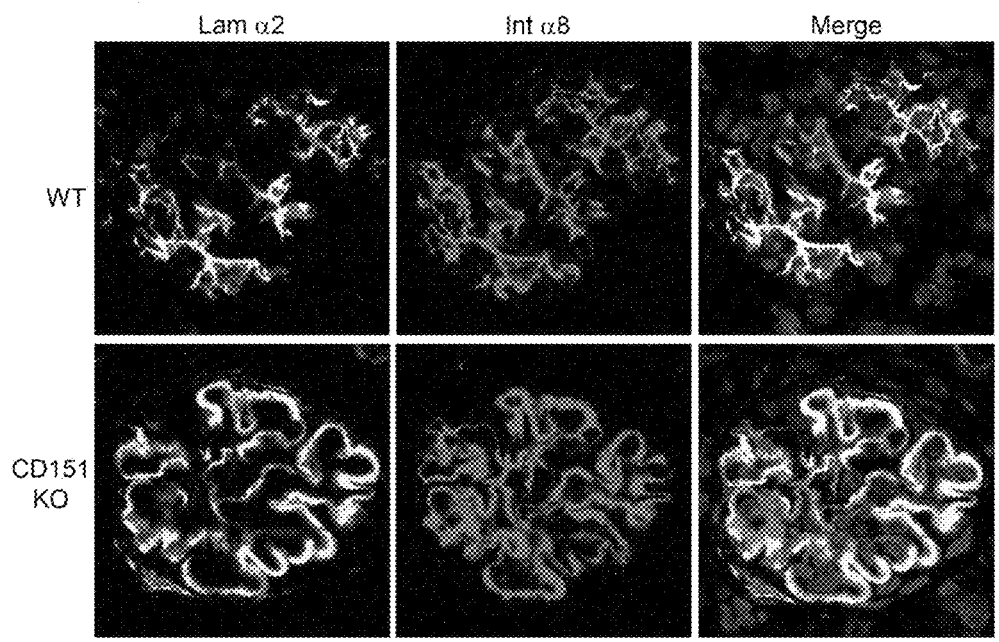
FIG. 5. Extensive mesangial process invasion of the glomerular capillary tufts is observed in CD151 knockout mice. Kidney cryosections from 8 week old wild type and CDC151 KO mice (on the FVB background) were analyzed by dual immunofluorescence immunostaining using antibodies against either laminin $\alpha 2$ or integrin $\alpha 8$. Extensive mesangial process invasion of the capillary tuft is observed in the glomeruli from CD151 knockout mice relative to wild type mice. Note that the extent of mesangial process invasion in CD151 knockout mice is much greater than that observed in Alport mice.

It is likely the increased biomechanical stress on the glomerular capillary tuft in Alport glomeruli is due to the change in GBM type IV composition from dual networks of α1(IV)/α2(IV) and α3(IV)/α4(IV)/α5(IV) collagen to one comprised only of α1(IV)/α2(IV) collagen. The latter is thinner and known to contain fewer interchain disulfide crosslinks (Gunwar et al., 1998, *J Biol Chem;* 273(15):8767-75) which would intuitively be expected to result in increasing the elasticity of the glomerular filtration barrier. In order to provide independent validation, a completely different model was examined that would also be expected to affect the elastic integrity of the glomerular filtration barrier, the CD151 knockout mouse. CD151 is a tetraspanin co-receptor for integrin α3β1 which functions to increase the affinity of integrin α3β1 for its GBM ligand, laminin α5 (Nishiuchi et al., 2005, *Proc Natl Acad Sci USA;* 102(6):1939-44). Deletion of CD151 results in glomerular disease with morphological changes in the GBM strikingly similar to Alport syndrome (Baleato et al., 2008, *Am J Pathol;* 173(4):927-37). Recently it was shown that hypertension accelerates the progression of glomerular disease in the CD151 knockout mouse, similar to our observations for the Alport mouse (Sachs et al., 2012, *J Clin Invest;* 122(1):348-58). Considering all of this, glomeruli from the CD151 knockout mouse were examined for mesangial process invasion and laminin 211 deposition in the GBM. The results in FIG. 5 are impressive, in that this mouse shows a near complete inundation of the glomerular capillary tufts with integrin α8 and laminin α2 immunopositivity, demonstrating mesangial process invasion and deposition of mesangial laminins in the GBM in this genetically unrelated model.

Figure 6:
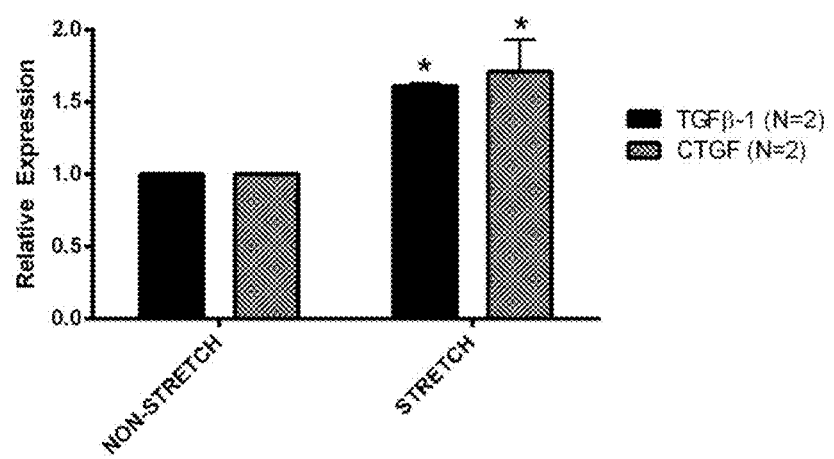
FIG. 6. Biomechanical stretching of cultured primary mesangial cells induces expression of pro-migratory cytokines, CTGF and TGF-$\beta 1$ mRNA. Primary mesangial cell cultures from wild type mice were subjected to cyclic biomechanical stretching for 24 hours. RNA from multiple replicates was analyzed by quantitative real time RT-PCR for CTGF and TGF-$\beta 1$ mRNA. Statistically significant increases in expression for both cytokines was observed ($p<0.05$).

If biomechanical strain can induce the activation of mesangial process invasion of the capillary tuft, pro-migratory responses will be activated in vitro by mechanically stretching cultured primary mesangial cells. Primary cultured mesangial cells, derived from 129 Sv/J mice, were subjected to cyclic cell stretching using the Flexcell system for 24 hours. Expression of several pro-migratory cytokines was quantified by real time RT-PCR. The results in FIG. 6 demonstrate that expression of both TGF-β1 and CTGF are significantly elevated in cells subjected to biomechanical stretching relative to cells cultured under identical conditions, but not subjected to stretch.

Figure 7:
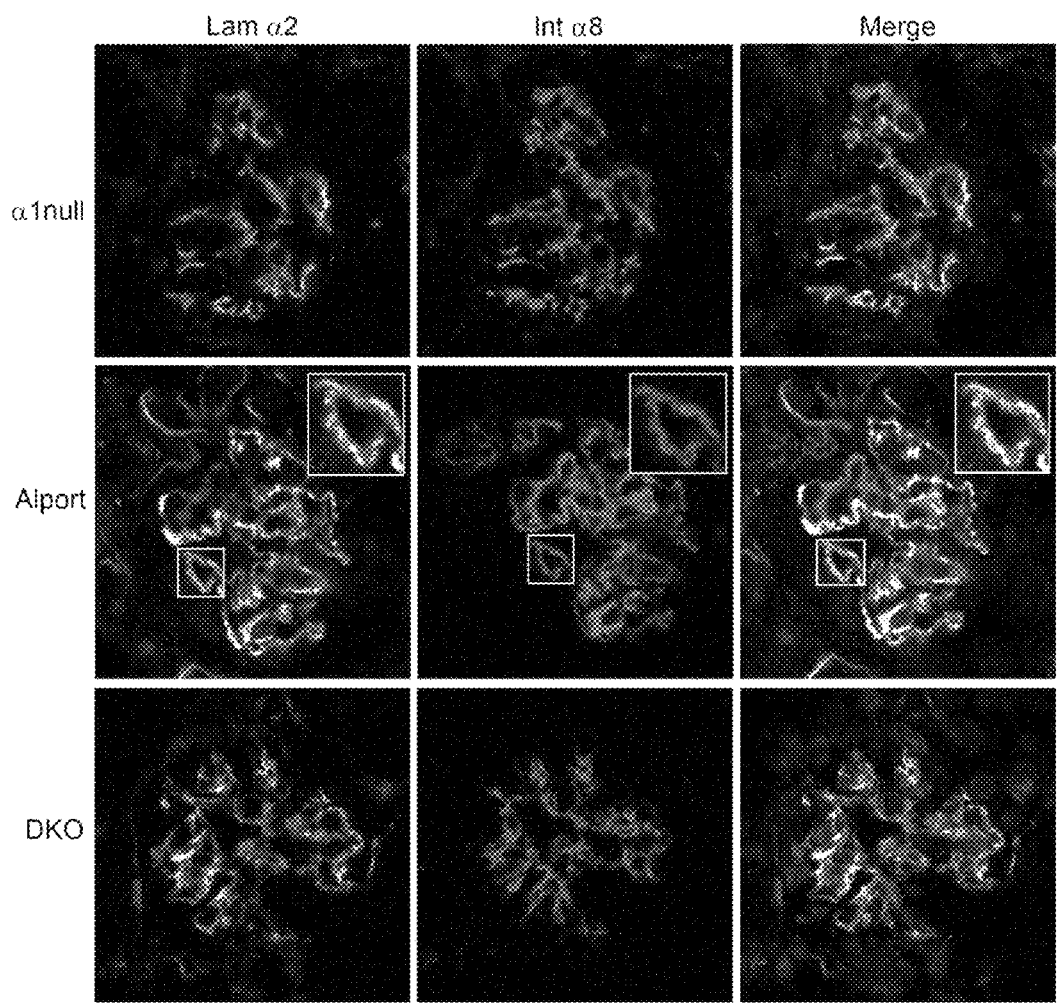
FIG. 7. $\alpha 1$ integrin deletion in Alport mice results in markedly reduced mesangial process invasion of the glomerular capillary tufts. Glomeruli from 7 week old integrin $\alpha 1$-null mice, Alport mice, and integrin $\alpha 1$-null Alport mice were analyzed by dual immunofluorescence immunostaining using antibodies against either laminin $\alpha 2$ or integrin $\alpha 8$. The degree of mesangial process invasion of the glomerular capillary tufts was greatly reduced in the integrin $\alpha 1$-null Alport mice relative to age/strain-matched Alport mice.

Mesangial cell migration (in vitro) and mesangial process invasion of the glomerular capillary loops (in vivo) are regulated by integrin α1β1 mediated Rac1/CDC42 crosstalk. Earlier work demonstrated that deletion of α1 integrin markedly attenuated the progression of glomerular disease in Alport mice (Cosgrove et al., 2000, *Am J Pathol;* 157(5): 1649-59). Although is highly likely that disease attenuation in integrin α1-null Alport mice emanates from the mesangial compartment where integrin α1β1 is highly expressed, the molecular mechanism underlying this effect has remained unclear. FIG. 7 shows that deletion of α1 integrin markedly reduces the dynamics of mesangial process invasion of the capillary tufts in Alport mice, consistent with the reduction in GBM laminin 211 deposition shown here and previously (Cosgrove et al., 2000, *Am J Pathol;* 157(5):1649-59).

Since it is well established that the formation of filopodia and lamellipodia require the concerted action of the small GTPases Rac1 and CDC42 (Vicente-Manzanares et al., 2009, *J Cell Sci;* 122(2):199-206), cell migration assays were performed using the Boyden chamber approach to determine whether such a functional connection was evident in cultured wild type and integrin α1-null mesangial cells. The results in FIG. 8 (A) show that integrin α1-null mesangial cells show a significant reduction in migratory potential relative to wild type mesangial cells. Migration of wild type cells was significantly reduced when cells were treated with either the integrin linked kinase inhibitor QLT-0267, the Rac1 inhibitor NSC 23766, or the CDC42 inhibitor ML141. Cell migration of wild type cells were not affected by treatment with the pan AKT inhibitor GSK 690693. Integrin α1-null mesangial cell migration was significantly reduced when cells were treated with ILK inhibitors, but unaffected when treated with Rac1 inhibitors, demonstrating that deletion of α1 integrin abrogates Rac1-dependent cell migration.

Figure 8:
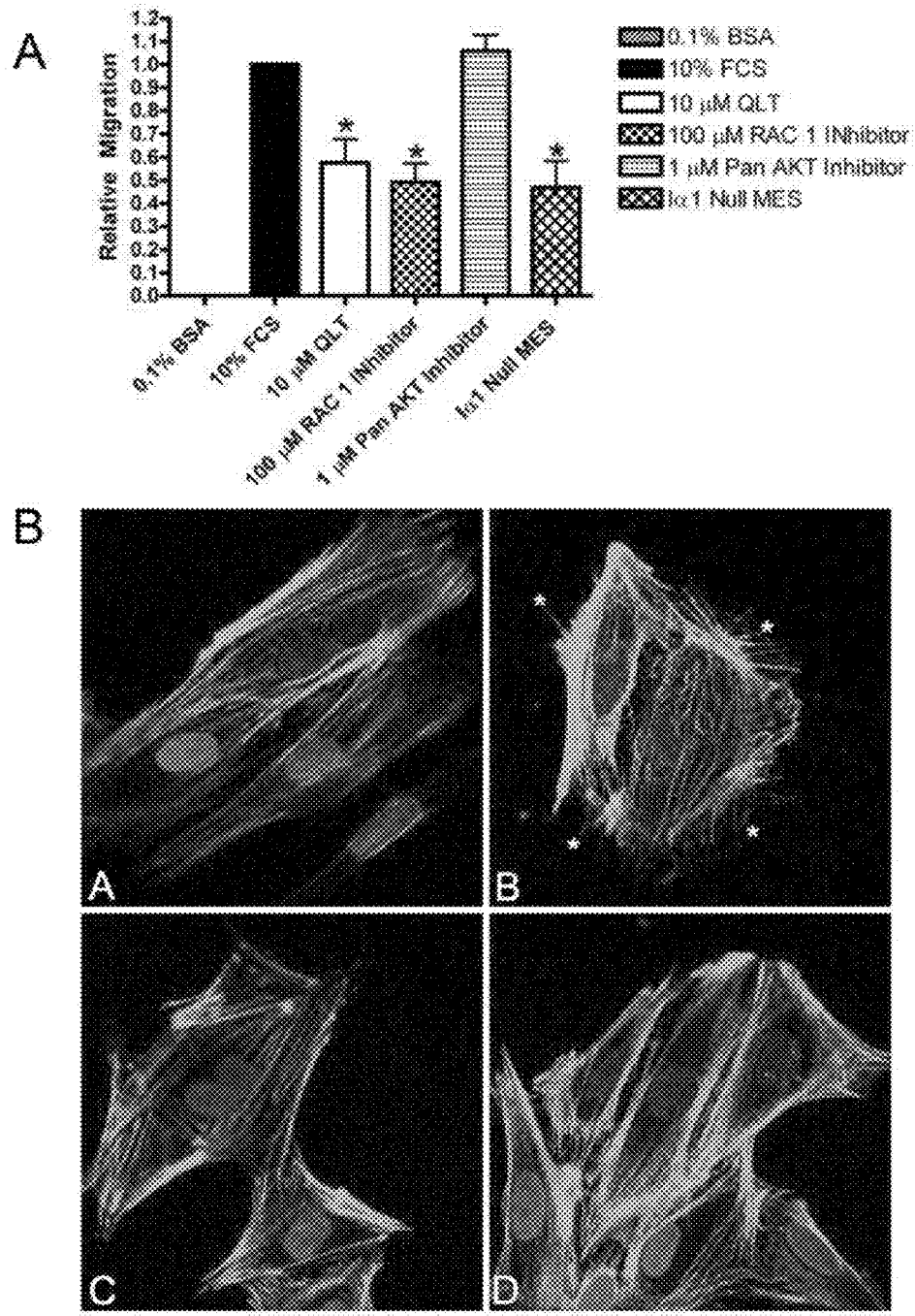
FIG. 8. Integrin $\alpha 1\beta 1$-dependent Rac1/CDC42 activation mediates dynamic remodeling of the actin cytoskeleton and mesangial process invasion of the glomerular capillary tufts. A) Migration of primary cultured mesangial cells is significantly reduced under conditions of integrin $\alpha 1$ deletion, Integrin linked kinase inhibition, Rac1 inhibition, and CDC42 inhibition, but not AKT inhibition. In contrast, the migratory potential of cultured integrin α1-null mesangial cells is unaffected by inhibition of either Rac1 or CDC42. Migration was measured by Boyden chamber assay in the presence or absence of ILK inhibitor, QLT-0267; Rac1 inhibitor, NSC 23766; CDC42 inhibitor, ML141; or the pan-AKT inhibitor GSK 690693. Multiple replicate experiments were performed on multiple independent derivations of mesangial cells and the data analyzed by Students-t-test. Asterisks denote statistically significant differences relative to 10% FCS ($p<0.05$). B) Treatment of cultured mesangial cells with LPS induced cytoskeletal rearrangement with numerous actin spikes (untreated cells, A; LPS treated cells, B), and these morphological changes are blocked by treatment of cells with either Rac1 inhibitors (C), or CDC42 inhibitors (D). Untreated integrin α1-null cells did not respond to LPS treatment. C) Treatment of cultured mesangial cells with LPS results in polarized localization of CDC42 and associated with filopodia (B, insert, compared to Golgi and cytosolic localization of CCD42 in wild type cells (A). Pre-treatment of cells with the Rac1 inhibitor, NSC 23766, abolished LPS-activated polarized localization of CDC42 (C), indicating cross-talk between Rac1 and CDC42. D shows a GTP-Rac1 pull down assay which confirms LPS-mediated activation of Rac1 in cultured mesangial cells, which was blocked by pre-treatment with Rac1 inhibitors, but not CDC42 inhibitor.
Figure 8:
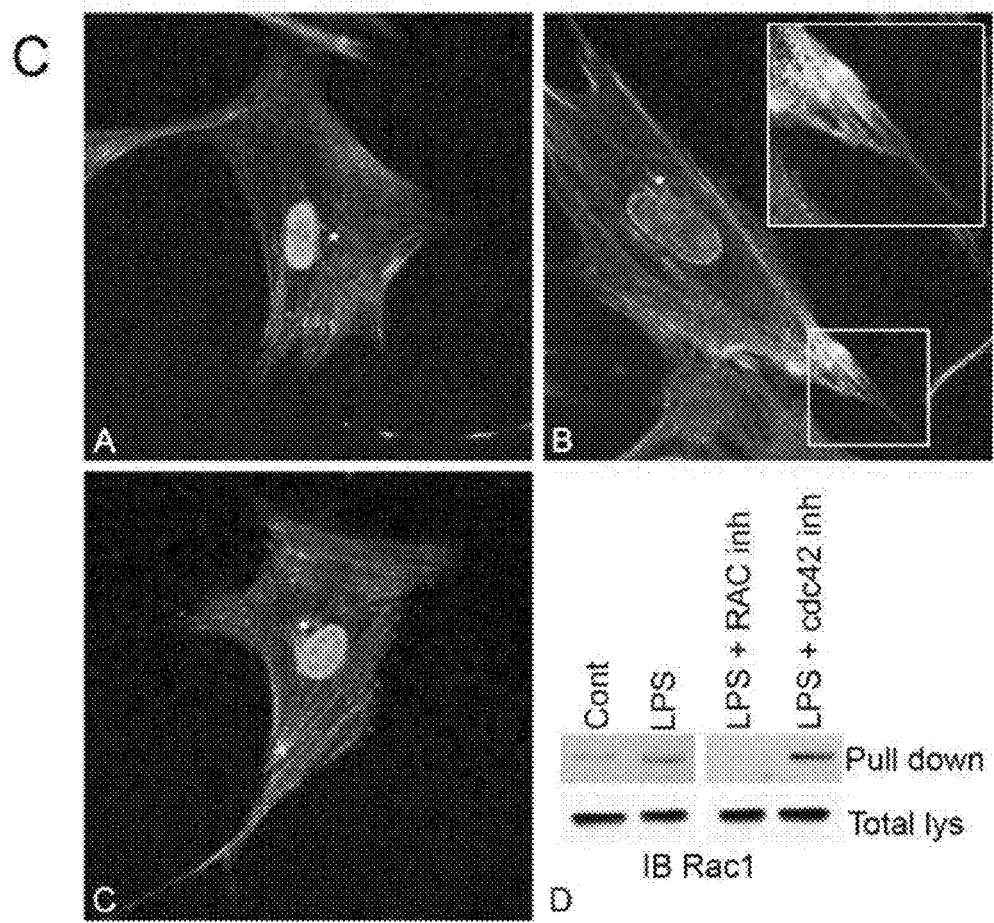

Treatment of cells with the bacterial endotoxin lipopolysaccharide (LPS) activates both Rac1 and CDC42 GTPases (Sanlioglu et al., 2001, *J Biol Chem;* 276(32):30188-98; and Fessler et al., 2004, *J Biol Chem;* 279(38):39989-98), and is known to induce the formation of both lamellipodia and filopodia in cultured mesangial cells (Bursten et al., 1991, *Am J Pathol;* 139(2):371-82). Cultured wild type mesangial cells were treated with LPS, the actin filaments stained with phalloidin, and the cultures examined for morphological changes. As shown in FIG. 8 (B), after 30 minutes, treated cells undergo a stark morphological change about half of the cells sprouting numerous filopodia (denoted by asterisks), that are easily discernable, blinded, in numerous replicate experiments. Cells treated with LPS in combination with either the Rac1 inhibitor NSC 23766 or the CDC42 inhibitor ML 141 could not be distinguished in blinded experiments form untreated wild type mesangial cells (FIG. 8 (B) panels C and D, respectively).

Interestingly, treatment of integrin α1-null mesangial cells with LPS had no discernable effect on cell morphology. To further validate these findings, either wild type or α1-null mesangial cell cultures were stimulated with LPS in the presence or absence of either Rac1 or CDC42 inhibitors and performed immunofluorescence analysis for CDC42 localization and pull down assays for activated Rac1. As shown in FIG. 8 (C), treatment of cells with LPS resulted in polarized localization of CDC42 associated with staining in adjacent filopodia (panel B insert), an established characteristic of CDC42 activation (Etienne-Manneville and Hall, 2001, *Cell;* 106:489-498; and Huang et al., 2011, *J Cell Biochem;* 112(6):1572-1584). Treatment of these cells with Rac1 inhibitor abolished this polarized activation, indicating cross-talk between Rac1 and CDC42. Integrin α1-null mesangial cells did not respond to LPS activation with polarized CDC42 localization. Pull down assays demonstrate that LPS treatment does indeed activate Rac1, and that pre-treatment of cells with the Rac1 inhibitor abolishes its activation (FIG. 8C(d)). Interestingly, pre-treatment of cells with CDC42 inhibitors did not block LPS mediated Rac1 activation, suggesting that, while Rac1 inhibitors block LPS-CDC42 activation (FIG. 8 (C), panel C), CDC42 inhibitors do not block Rac1 activation (FIG. 8 (C), panel D).

Figure 9:
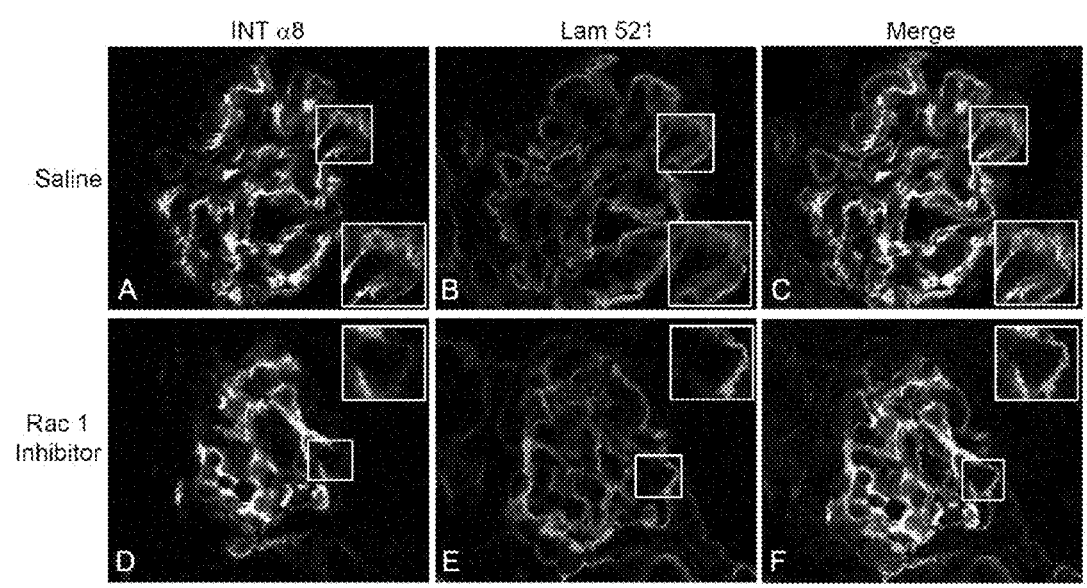
FIG. 9. Treatment of Alport mice with Rac1 inhibitors partially ameliorates mesangial cell process invasion of the glomerular capillary tufts. Alport mice on the 129 Sv background were injected once daily with either saline or the Rac1 inhibitor NSC 23766 from 2 weeks to 6 weeks of age. Kidney cryosections were analyzed by dual immunofluorescence immunostaining using antibodies against either laminin α2 (B and E) or integrin α8 (A and D). C and D represent a merging of results from staining with laminin α2 and integrin α8. The degree of mesangial process invasion of the glomerular capillary tufts was ameliorated in the Rac1 inhibitor-treated mice relative to mice injected with saline.

To examine the effect of Rac1 inhibitors on Alport glomerular disease progression, either wild type or Alport mice were treated with inhibitors by IP injection from 2 weeks to 6 weeks of age. Glomeruli were examined for mesangial process invasion of the capillary tufts by dual immunofluorescence microscopy using antibodies specific for either integrin α8 or the GBM marker laminin α5. The results in FIG. 9 (A-F) demonstrate that saline-injected mice show significant co-localization of integrin α8 and laminin α5 throughout many of the glomerular capillary tufts, while mice injected with the Rac1 inhibitor showed very little mesangial process invasion. Combined, the data in FIG. 7, FIG. 8, and FIG. 9 confirm that mesangial process invasion of the glomerular capillaries is a Rac1-dependent process, and that Rac1 activation is attenuated by integrin α1 deletion both in vitro and in vivo. Furthermore, LPS activation of filopodia in wild type mesangial cells (but not in α1-null mesangial cells) involves both Rac1 and CDC42 activation, suggesting α1β1 integrin-dependent cross talk between the two small GTPases in the signaling complex.

Figure 10:
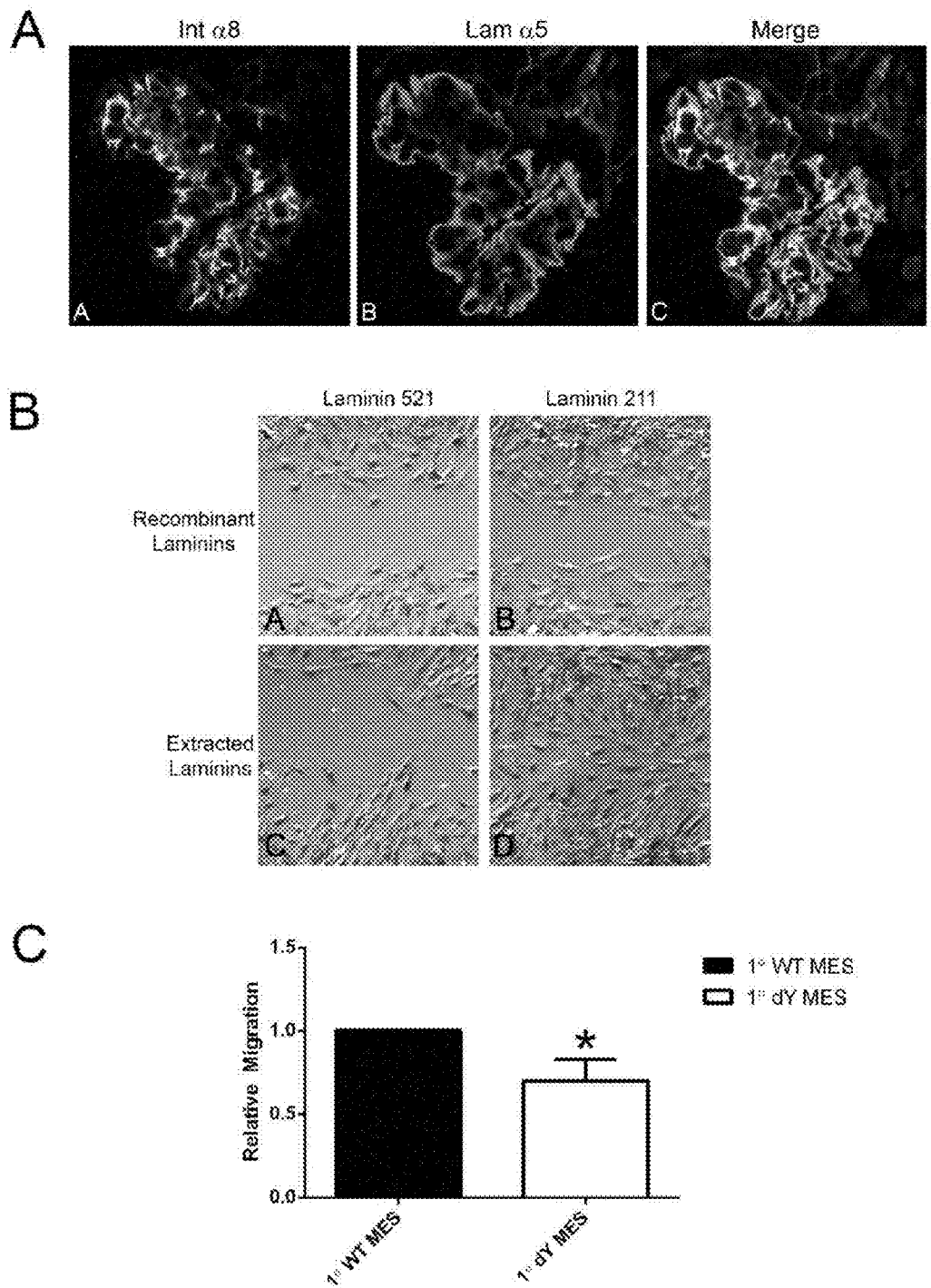
FIG. 10. Laminin 211 potentiates mesangial process invasion of the glomerular capillary loops in Alport mice, and promotes mesangial cell migration in vitro. A) Laminin laminin α2-deficient Alport mice show reduced mesangial process invasion of the glomerular capillary tufts. Cryosections of kidney tissue from 8 week old laminin α2-deficient Alport mice were analyzed by dual immunofluorescence immunostaining using antibodies against either laminin α5 or integrin α8. The degree of mesangial process invasion of the glomerular capillary tufts was greatly reduced in the laminin α2-null Alport mice relative to Alport mice (compare with FIG. 2, panels J-L). B) Wild type mesangial cells migrate more robustly on laminin 211 compared to laminin 521 (GBM laminin). Wound scratch assays were performed using wild type mesangial cells cultured on wither recombinant purified laminins or commercially available laminins extracted from either placenta (primarily laminin 511) or muscle (primarily laminin 211). Images shown are representative of multiple replicates. C) Primary mesangial cells from laminin α2-deficient mice show impaired migratory potential relative to wild type mesangial cells. Boyden chamber assays were performed. Blinded cell counts from multiple replicates were analyzed. Asterisk denotes statistically significant differences ($p<0.05$).

Laminin 211 enhances mesangial cell migration and mesangial process invasion of the capillary loops. In a related study to determine whether GBM laminin 211 contributed mechanistically to the progression of Alport glomerular disease, a laminin α2-deficient mouse was crossed with the Alport mouse to produce a double knockout. One effect of laminin α2 deficiency was a marked reduction of mesangial process invasion of the capillary loops (FIG. 10 (A)). This indicates that laminin 211 might facilitate mesangial process invasion of the capillary loops. Thus, cell migration assays were performed on either laminin 211 or laminin 521 (GBM laminin) Two different laminin preparations were used. One was extracted laminin from either placenta (primarily laminin 511) or muscle (primarily laminin 211); the other commercially available purified recombinant laminin heterotrimers. A scratch wound assay was used as opposed to the Boyden chamber, to determine the role of specific extracellular matrix in potentiating mesangial cell migration. As shown in FIG. 10 (B), wild type mesangial cells migrate much more efficiently on laminin 211 compared to laminin 521. While the effect was more pronounced on the muscle laminin preparation relative to the placental laminin preparation, it is also clear on the pure recombinant laminin substrates. To more directly confirm the role of laminin α2 in migratory potential, the relative migration of wild type mesangial cells to mesangial cells derived from laminin α2-deficient mice was measured, this time using the Boyden chamber approach. The results in FIG. 10 (C) represent multiple derivations of both cell types, and demonstrate a statistically significant reduction in the migratory potential of laminin α2-deficient mesangial cells relative to wild type mesangial cells. Collectively the data in FIG. 10 indicate that laminin 211 deposition by the mesangial processes functionally contributes to the process invasion of the capillary tuft in Alport and CD151-knockout glomeruli.

Discussion

Earlier studies of Alport mouse, dog, and humans reported the presence of "abnormal" laminins in the GBM, including laminin 211 and laminin 111 (Cosgrove et al., 2000, *Am J Pathol;* 157(5):1649-59; Kashtan et al., 2001, *J Am Soc Nephrol;* 12:252-60; and Abrahamson et al., 2003, *Kidney Int;* 63:826-34). These laminins tend to accumulate in areas of irregular thickening of the GBM, and these thickened areas have been shown to be more permeable to ferritin, suggesting that they are comprised of loosely assembled or partially degraded extracellular matrix (Abrahamson et al., 2007, *J Am Soc Nephrol;* 18:2465-72). In addition to the "abnormal" laminins, fibronectin and heparin sulfate proteoglycans have also been reported to accumulate in the GBM of Alport mice (Cosgrove et al., 1996, *Genes Dev;* 10(23): 2981-2992). What all of these ECM components have in common is that they are predominantly found in the mesangial matrix (Schlondorff and Banas, 2009, *J Am Soc Nephrol;* 20:1179-87).

This example determined that these abnormal GBM matrix molecules that progressively accumulate in the Alport GBM are of mesangial cell origin. Integrin α8 was used as a specific mesangial cell surface marker to demonstrate that mesangial processes invade the capillary tufts and co-localize with laminin 211, a mesangial laminin. Integrin α8 is expressed in mesangial cells, but not in other glomerular cell types (Hartner et al., 1999, *Kidney Int;* 56(4): 1468-80), and its expression is generally restricted to smooth muscle cells and neuronal cell types (Bossy et al., 1991, *EMBO J;* 10(9):2375-2385; and Schnapp et al., 1995, *J Cell Sci;* 108:537-544). Mesangial process invasion of the glomerular capillary tufts was exacerbated by hypertension, indicating that the mechanism triggering this event was mediated by biomechanical stress, likely at the interface between the mesangial processes and the sub-endothelial interface with the glomerular capillaries, an area known to provide important structural support for the capillary loops (Schlondorff and Banas, 2009, *J Am Soc Nephrol;* 20:1179-87). The Alport mutations, which can be either autosomal recessive (mutations in either COL4A3 or COL4A4 genes (Mochizuki et al., 1994, *Nat Genet;* 8(1):77-81)) or X-linked (mutations in COL4A5 (Barker et al., 1990, *Science;* 248 (4960):1224-7)) result in the absence of the collagen α3(IV)/α4(IV)/α5(IV) network from the GBM. The consequence is a thinner GBM comprised of only α1(IV) and α2(IV) collagens, which have been shown to contain fewer interchain disulfide crosslinks (Gunwar et al., 1998, *J Biol Chem;* 273(15):8767-75). This structural change alters the biomechanical properties of the capillary tuft, resulting in stresses on the cells comprising the tuft even under normal glomerular blood pressures.

A second model was examined, the CD151 knockout mouse, which would also show enhanced strain on the capillary tufts. In this model, enhanced strain arises as a result of reduced adhesion of the podocyte pedicles to the GBM due to reduced affinity for the podocyte integrin α3β1 for its GBM ligand laminin 521 (Nishiuchi et al., 2005, *Proc Natl Acad Sci USA;* 102(6):1939-44). Mesangial process invasion of the glomerular capillary tufts in the CD151 mouse was even more robust than that for the Alport model. Like the Alport model (Meehan et al., 2009, *Kidney Int;* 76:968-976), glomerular pathology in the CD151mouse model, which shows ultrastructural lesions in the GBM strikingly similar to Alport syndrome (Baleato et al., 2008, *Am J Pathol;* 173(4):927-37; and Sachs et al., 2006, *J Cell Biol;* 175(1):33-9) is significantly exacerbated under hypertensive conditions (Sachs et al., 2012, *J Clin Invest;* 122(1): 348-58). Collectively this evidence supports the notion that mutations affecting structural integrity of the glomerular capillary tuft result in unnatural stresses on the cells comprising the tuft. In the mesangial cell compartment this results in mesangial cell invasion of the tuft and deposition of matrix proteins in the GBM that are of mesangial cell origin.

Earlier work showed that deletion of the mesangial integrin α1β1 in Alport mice resulted in a marked attenuation in the progression of the glomerular pathology, with reduced proteinuria and a near doubling of lifespan (Cosgrove et al., 2000, *Am J Pathol;* 157(5):1649-59). The mechanism underlying the influence of mesangial α1β1 integrin on Alport renal disease progression has, until the present example, remained unclear. This example shows that mesangial process invasion is markedly attenuated in integrin α1-null Alport mice relative to strain/age matched Alport mice. This indicates that the signaling pathway that activates actin cytoskeletal rearrangements is perturbed in the absence of α1β1 integrin. Further, decreased migratory potential was observed for primary cultures of α1-null mesangial cells relative to wild type mesangial cells from strain/age matched mice (FIG. 8 (A)).

Lipopolysaccharide, which activates both Rac1 and CDC42 in wild type mesangial cells, failed to activate Rac1 or CDC42 (FIG. 8 (B)), and failed to activate actin cytoskeletal rearrangements in cultured α1-null mesangial cells. Collectively these data explain why deletion of α1-integrin results in attenuation of Alport glomerular pathogenesis and indicate that α1β1 integrin is a key sensor of biomechanical strain at the glomerular capillary tuft and participates in the adhesive signaling mechanism that links to the Rho GTPases Rac1 and CDC42 which activate actin polymerization dynamics required to process invasion of the glomerular capillary tufts.

Classically, Rac1 activation is associated with lamellipodia formation and CDC42 activation is associated with filopodia formation (Nobes and Hall, 1995, *Cell;* 81(1):53-62). Recently, evidence for crosstalk between the two Rho GTPases has emerged (Zamudio-Meza et al., 2009, *J Gen Virol;* 90(Pt 12):2902-11). This phenomenon is likely regulated through the guanine nucleotide exchange factor β1pix, which contains binding sites for both CDC42 and Rac1 (Chandi et al., 2004, *Biochem Biophys Res Commun;* 317 (2):384-9; and Chandi et al., 2005, *J Biol Chem;* 280(1): 578-84). This example provides evidence for cross-talk between Rac1 and CDC42 in cultured mesangial cells regulating actin cytoskeletal rearrangement including:

showing that treatment of mesangial cells with LPS, known to activate rapid actin cytoskeletal rearrangement (Bursten et al., 1991, *Am J Pathol;* 139(2):371-82), activates Rac1 in wild type mesangial cells (FIG. 8 (C), panel D); showing that membrane localization of CDC42, a known prerequisite for its activation, is blocked by addition of RAC1 inhibitors coincident with LPS stimulation (FIG. 8 (C), panels A-C); and showing that inclusion of either Rac1 inhibitors or CDC42 inhibitors upon stimulation of mesangial cell cultures with LPS blocks actin cytoskeletal rearrangements (FIG. 8 (B)).

Mesangial cell cultures subjected to cyclic biomechanical strain expressed elevated levels of the pro-migratory cytokines CTGF and TGF-β1, providing further evidence that biomechanical strain activates actin cytoskeletal dynamics required for mesangial process invasion. Both CTGF and TGF-β1 signaling have been shown to activate CDC42 (Edlund S et al., 2002, *Mol Bio Cell;* 13:902-14; and Crean et al., 2004, *FASEB J;* 18(13):1541-3), and both cytokines have been shown to be induced in Alport glomeruli (Sayers et al., 1999, *Kidney Int;* 56(5):1662-1673; and Kashtan et al., 2001, *J Am Soc Nephrol;* 12:252-60) indicating that activation of these signaling pathways might be an important underlying mechanism for the activation of mesangial process invasion of glomerular capillary tufts in Alport syndrome. Indeed, earlier work showed that inhibition of TGF-β1 in the Alport mouse resulted in abrogation of GBM thickening, in support of this notion (Cosgrove et al., 2000, *Am J Pathol;* 157(5):1649-59). And, when TGF-β1 was inhibited in α1 integrin-null Alport mice, a synergistic improvement in glomerular disease was observed suggesting that TGF-β1 and integrin α1 are working through distinct pathways (Cosgrove et al., 2000, *Am J Pathol;* 157(5):1649-59). Based on the current study, these pathways may converge on strain-mediated activation of Rac1/CDC42 in the mesangial cell compartment.

While the deposition of laminin 211 in the GBM of Alport mice was described more than 10 years ago (Cosgrove et al., 2000, *Am J Pathol;* 157(5):1649-59; and Kashtan et al., 2001, *J Am Soc Nephrol;* 12:252-60), a functional role for this laminin in Alport glomerular pathology has not been described. This example shows reduced mesangial process invasion of the glomerular capillary loops in Alport mice that are also lacking laminin α2, indicating that laminin 211 itself promotes the migration of processes into the glomerular capillary loops (FIG. 9 (A)). Consistent with this, the example shows that wild type mesangial cells migrate more robustly when cultured on laminin 211 compared to laminin 521, and that primary mesangial cells from laminin α2-deficient mice show impaired migration relative primary wild type mesangial cells from age/strain matched mice (FIG. 9 (B-C)). While modulation of mesangial cell migration by ECM has been described previously (Person et al., 1988, *Am J Pathol;* 133(3):609-14), this example shows that the strain-mediated mesangial process invasion of the capillary loops is enhanced by mesangial cell secreted laminin 211, which may explain why laminin 211 accumulates in the patchy irregularly thickened regions of the Alport GBM (see FIG. 1).

This example shows that the changes in the biophysical properties of the Alport glomerular capillary tuft results in biomechanical stresses that result in the induction of pathologic processes. Parallel observations in Alport and CD151 mouse models, including mesangial process invasion of the glomerular capillary tufts and deposition of laminin 211 provide additional support, since the two mouse models arise from mutations that would be expected to relax the structural integrity of the glomerular capillary tufts, but are otherwise mechanistically unrelated to each other. Recent studies of the biophysical properties of Alport glomeruli from pre-proteinuric mice reported increased deformability and suggested the glomeruli were "squishy" (Wyss et al., 2011, *Am J Physiol Cell Physiol;* 300:C397-C405). Collectively, this example supports a model where biomechanical stresses on the glomerular capillary tufts activate a promigratory signaling cascade in mesangial cells involving integrin α1β1-mediated activation of Rac1/CDC42 crosstalk. This activation culminates in the invasion of the capillary loops by mesangial processes. These processes clearly deposit laminin 211, which further exacerbates the mesangial process invasion. In addition to laminin 211, other mesangial matrix molecules are likely deposited in the GBM, and local action of mesangial cytokines (TGF-β1 and CTGF, for example) and MMPs might also contribute to the structural and functional properties of the Alport GBM (irregular thickening, splitting, permeability, etc.). In addition, all of these events are very likely to influence podocyte cell health. Thus, mesangial process invasion of the GBM is an important early event that precipitates glomerulosclerosis in Alport syndrome. The observation of mesangial process invasion of glomerular capillary loops in human Alport glomeruli provides relevance for these observations to the human disease. A better understanding of the activation process might reveal novel targets capable of preventing this event and arresting the Alport glomerular pathogenesis in its pre-initiated state.

Methods

Mice. All mice used in these studies were on pure genetic backgrounds. Autosomal recessive Alport mice were on the 129 Sv background. X-linked Alport mice were on the C57 Bl/6 background, laminin α2-deficient mice were on the 129 Sv background, integrin α1-null mice were on the 129 Sv background (Gardner et al., 1996, *Dev Biol;* 175(2):301-13), and CD151 knockout mice were on the FVB background (Takeda et al., 2007, *Blood;* 109(4):1524-32). All experiments were performed using strain/age-matched control mice. All animal studies were conducted in accordance to USDA approved standards and under the approval of the institutional IACUC. Every effort was made to minimize pain and discomfort.

Immunofluorescence microscopy. Fresh frozen kidneys were sectioned at 8 μm and acetone fixed. Sections were incubated overnight at 4° C. with 0.3% PBST (Triton X-100), 5% Fetal Bovine Serum, and with two of the following antibodies: rat anti-mouse Laminin-2 antibody (Sigma) at 1:200, goat anti-mouse Integrin α8 antibody (R & D Systems) at 1:100, rabbit anti-mouse Laminin-5 antibody at 1:200, rabbit anti-human Laminin-5 antibody (GeneTex) at 1:500, rabbit anti-mouse CDC42 antibody (ProteinTech) at 1:50, and goat anti-mouse α-actinin-4 antibody (Santa Cruz) at 1:50. Affinity purified rabbit anti-collagen α3(IV) antibodies were as previously described. Slides were rinsed with 1×PBS and incubated with the appropriate Alexa Fluor donkey secondary antibodies at 1:300 for 1 hour at room temperature. They were then rinsed again with 1×PBS and mounted with Vectashield Mounting Medium with Dapi (Vector).

MES Migration (insert). Transwell cell migration assays were performed as described by Daniel et al. (Daniel et al., 2012, *Lab Invest;* 92(6): 812-26) with some modifications. 8 micron, 24-well plate control inserts (BD Bioscience, Bedford, Mass.) were coated overnight at 4° C. with 100 μl of 0.1% gelatin/PBS then washed 1× with PBS. MES cultures were incubated in 1% FCS overnight, then 0.05%

BSA-containing media for at least 8 hours, washed 1× with PBS and carefully tryspinized to ensure a single cell suspension and limited "clumping" of cells. After serum-neutralization and subsequent centrifugation, ~100,000 cells were resuspended in 1.5 mls of 0.05% BSA media containing activators/inhibitors. The wells of a 24-well plate were filled with 0.75 mls of 10% FCS-containing media plus activators/inhibitors (excluding 0.05% BSA control well). 0.5 ml of cell-suspension was loaded into the gelatin-coated insert and the insert placed in a well. Wells were visually inspected for bubbles beneath insert and equal distribution of cell-suspension. Cells were allowed to migrate overnight (~18 hrs). Using a moistened cotton swab, non-migrated cells were liberated from the apical-side of the insert by gentle but firm rubbing. A second swab repeated the removal and was followed by a single wash with PBS. Inserts were fixed, stained and washed (2×) in companion 24 well plate(s) containing 0.5 mls MEOH, 0.5 mls 1% Toluidine Blue in 1% Borax and 0.5 mls distilled H2O, respectively. Inserts were air dried and counted at 100× magnification. Five fields were counted on each insert including one center and four periphery areas. Data was expressed as relative to 10% FCS control well (set equal to one).

Scratch wound migration assay. For Basal Lamina studies SUPERFROST™ Plus (VWR) microscope slides were coated with the following: 100 ng/ml MEROSIN™ (Millipore), 100 ng/ml human placental laminin (Sigma-Aldrich), 20 ng/ml human rlaminin-211 (BioLamina), or 20 ng/ml human rlaminin-521 (BioLamina) per manufacturer's suggestion. Slide(s) were placed in a tissue culture dish and an 8×8 mm cloning ring (Bellco Glass) placed on the coated area. A 100 µl of cell suspension (~30,000 cells) in 1% FBS-containing media was added to the cloning ring and the cells were allowed to attach for ~8 hours, PBS was placed in the dish and the ring removed. A ~0.3-0.5 mm swath of cells was removed was by running a serological pipette at a ~45° angle through the monolayer. After capturing images of removed cells, slides were incubated for 24 hours in 1% FBS containing media, washed with PBS, fixed in methanol for 5 minutes, air dried and stained for 30 minutes with modified Giemsa Stain (Sigma-Aldrich). Images of previously photographed fields were captured using a Leica MZ10F Microscope fitted with a DFC310FX camera.

Biomechanical stretching of cultured mesangial cells. Low passage, sub confluent, primary mesangial cells were trypsinized and seeded onto BIOFLEX™ 6-well plates (Flexcell International Corp) coated with Rat tail type I collagen (BD Biosciences). Cells were plated in 5% FCS containing media at densities that resulted in 20-40% confluence. 0.5% FCS media was placed on the cells the next day. 48 hours later the media was changed and the cultures exposed to a regimen of 60 cycles of stretch and relaxation per minute with amplitude of 10% radial surface elongation. The Flexercell Strain Unit FX4000 (Flexcell International Corp., Hillsborough, N.C.) was used to induce stretch/relaxation for 18 hours according to manufacturer's directions. Cells grown identically, but not exposed to stretch, served as controls.

Real time qRT-PCR. Total RNA was reverse transcribed using SUPERSCRIPT® III (Invitrogen) with Oligo(dT)$_{20}$ Primer (Invitrogen). The real time PCR was carried out using TAQMAN® Gene Expression Master Mix (Applied Biosystems), and quantified using ABI PRISM® 7000 sequence detection system (Applied Biosystems). Samples were normalized to Mouse GAPDH Endogenous Control VIC® Probe (Applied Biosystems catalogue #4352339E) which was run alongside the CTGF and TGFβ-1 TAQ-MAN® Gene Expression Assay Probes (Applied Biosystems catalogue #4331182). Each of the samples were run in triplicate with a final reaction volume of 50 µl with the following cycling parameters: 50° C. for 2 min, 95° C. for 10 min, followed by 40 cycles of a two-step PCR consisting of 95° C. for 15 s and 60° C. for 1 min. Relative changes in gene expression were determined by calculating the fold change using the comparative $C_T$ method of $2^{-\Delta\Delta CT}$.

Activation of mesangial cell cultures by treatment with LPS. Sub-confluent mesangial cells were tryspinized; plated at low density on Rat tail type 1 collagen (BD Biosciences) coated cytology slides (VWR) and incubated overnight in 1% FCS-containing media. One hour after the addition of serum-free media, 1 µM CDC42 Inhibitor (KSC-23-233) and 10 µM Rac-1 Inhibitor, NSC-23766 (Tocris) were added to individual slides and allowed to incubate for an additional hour. 10 ng/ml Lipopolysaccharides (Sigma-Aldrich) was added to cells, incubated 1 hour, fixed in ice cold acetone for 5 minutes and allowed to air dry ~2 hours. Cells were stained with a 1:100 dilution of antibodies specific for CDC42 (10155-1-AP, PROTEINTECH™), and phalloidin (Molecular Probes) imaged. Untreated, LPS alone and LPS plus inhibitors treatments were repeated on two different derivations of primary mesangial cells with qualitatively consistent results.

Pull down assay. Pull down experiments for Rac1 in mesangial cells were done using the Rac1 Activation Assay Biochem Kit (BK035, Cytoskeleton Inc., CO) and according to manufacturer instructions with minor modifications. Briefly, 500-800 µg of protein lysates were incubated with 20 µl of PAK-PBD beads for 1 hour at 4° C. Pull down samples and total protein lysates (30-50 µg of protein) were run in a 12% SDS-PAGE gel, transferred to PVDF membranes and blocked in 5% milk for 30 minutes at room temperature. Rac-1 antibody incubation was done overnight at 4° C. with rocking. After secondary antibody incubation and several washes membranes were developed using the ECL Plus kit (32134, Pierce, Ill.) pull-down experiments or the SuperSignal West Femto kit (34094, Pierce, Ill.) for total lysates. Films were exposed for 40 min and 5 min respectively and developed using a film processor (Biomedical Imaging Systems, Model SRX-101A).

Confocal microscopy. Slides were cover slipped using Vectashield mounting medium containing DAPI to counterstain the nuclei (Vector Lab, CA) and confocal images captured using a Zeiss AxioPlan 2IF MOT microscope interfaced with a LSM510 META confocal imaging system, using a 63×NA:1.4 oil objective. Final figures were assembled using Adobe Photoshop and Illustrator software (Adobe Systems, CA).

This example has now published as "α1β1 integrin/Rac1-dependent mesangial invasion of glomerular capillaries in Alport syndrome," Zallocchi M, Johnson B M, Meehan D T, Delimont D, Cosgrove D, *Am J Pathol.* 2013 October; 183(4):1269-80. doi: 10.1016/j.ajpath.2013.06.015. Epub 2013 Aug. 2, which is hereby incorporated by reference in its entirety.

Example 2

Endothelin Blockade with Bosentan Ameliorates Renal Pathology

This example describes a new etiology for Bosentan action in Alport glomerular disease through its capacity to block endothelin receptors on mesangial cells, blocking Rac1/CDC42 which prevents mesangial invasion of the glomerular capillaries and thereby ameliorates renal disease progression. This example substantiates, for the first time, a new use for the known drug Bosentan.

One potential activator of cytoskeletal rearrangement in mesangial cells is endothelin receptor mediated activation of Rac1/CDC42. A significant amount of work has been done using cultured mesangial cells that suggests a functional link between endothelin receptor activation and activation of the rho GTPases, Rac1 and CDC42 (reviewed in Sorokin, 2011, *Contrib Nephrol;* 172:50-62). As shown in Example 1 and herein, when Rac1 activation was blocked, mesangial process invasion of glomerular capillaries was ameliorated (see also Zallocchi et al., 2013, *Am J Pathol;* 183(4):1269-80).

Figure 11:
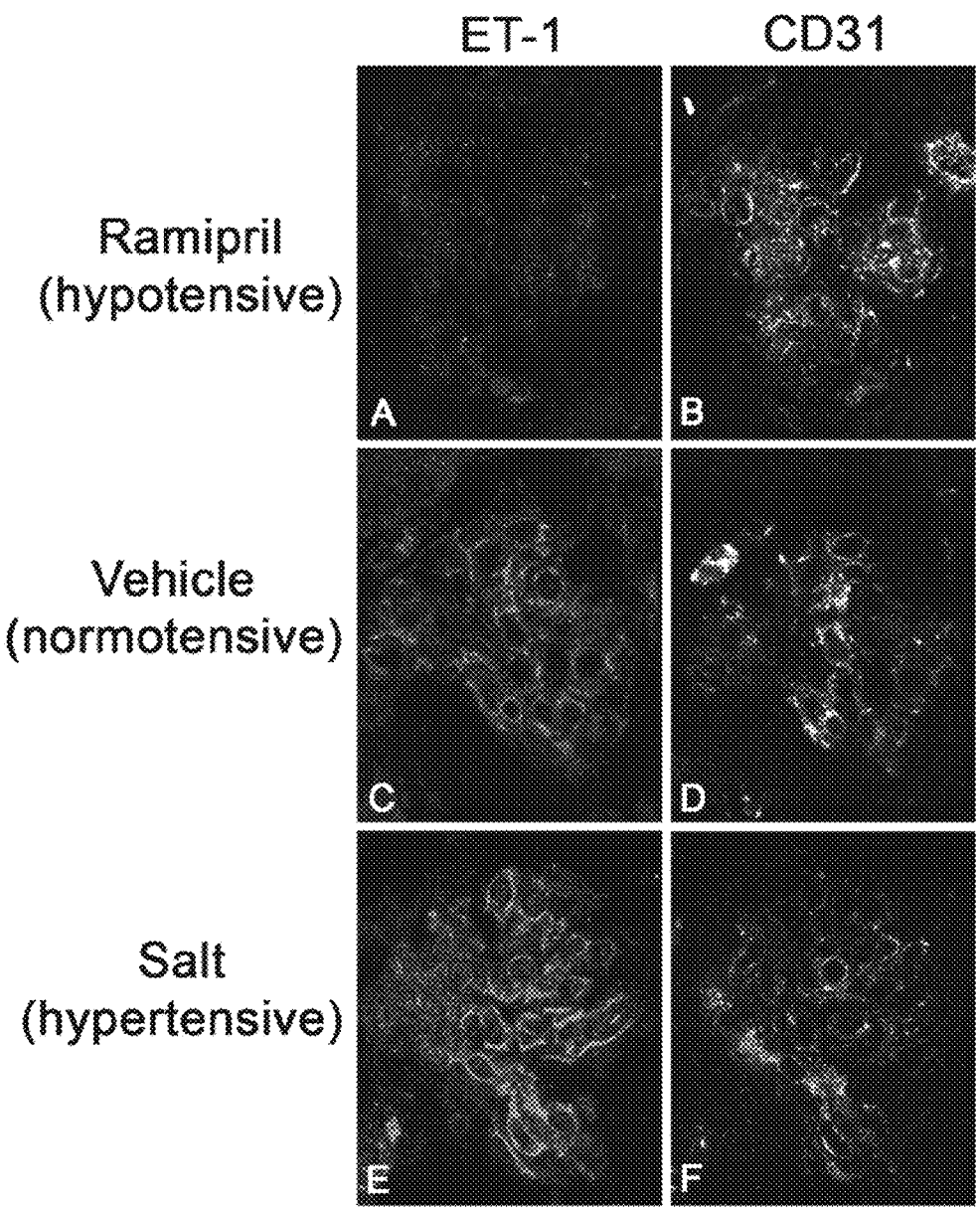
FIG. 11. Hypertension induces endothelin-1 in Alport glomerular endothelial cells. Wild type and C57Bl/6 X-linked Alport mice were made hypotensive by giving them the ACE inhibitor Ramipril in drinking water from 4 to 7 weeks of age, normotensive by giving plain drinking water, or hypertensive by giving them L-NAME salts in the drinking water. Cryosections were dual immunostained with antibodies specific for either endothelin-1 (A, C, and E) or CD31 (B, D, and F) (a marker for endothelial cells). ET-1, endothelin-1. Note very little ET-1 immunostaining in the glomeruli of hypotensive mice (A) versus robust endothelial cell-specific immunostaining for ET-1 in the glomeruli of hypertensive mice (E).
Figure 12:
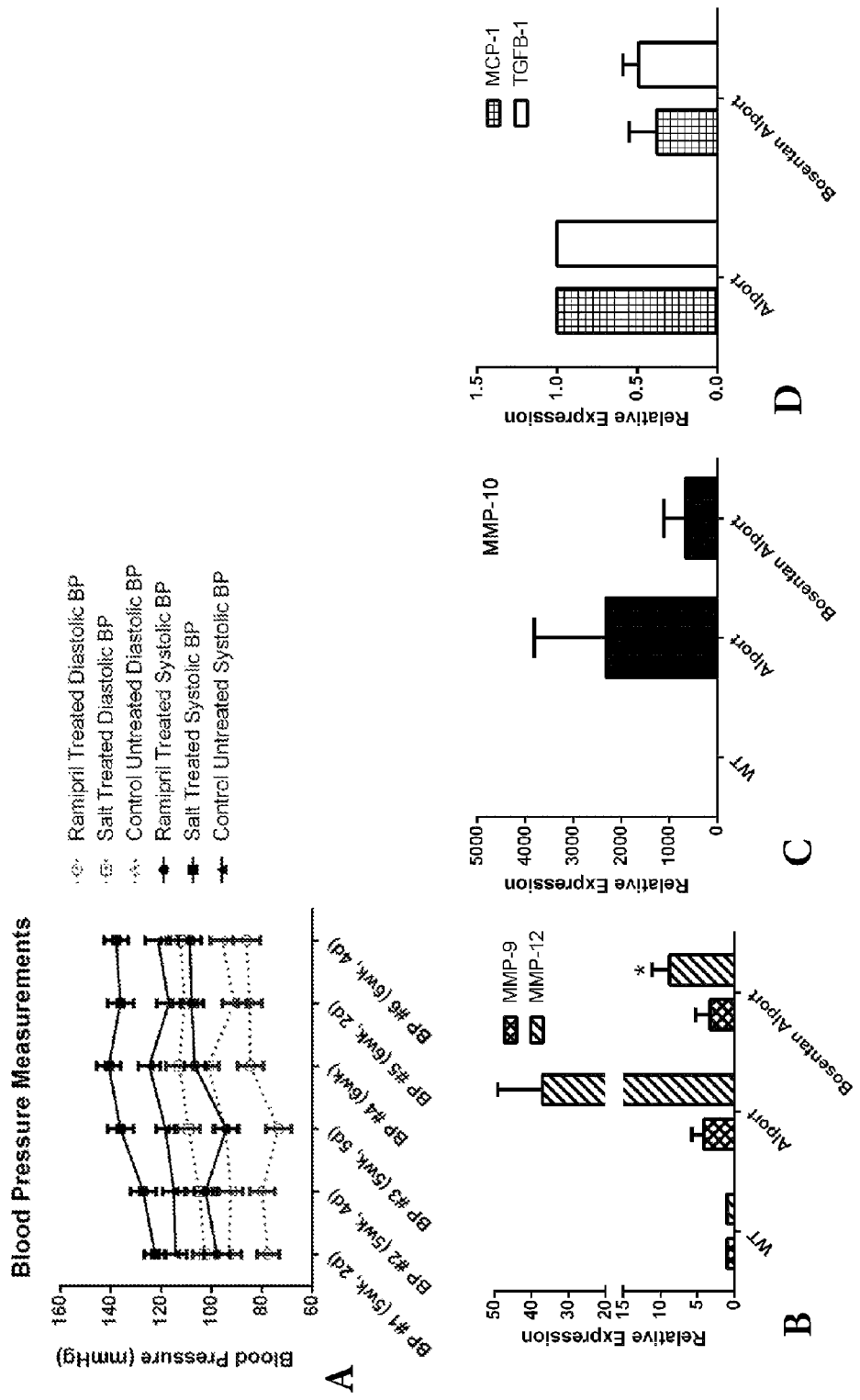
FIG. 12. Inducement of hypertension and hypotension in Alport mice. X-linked Alport mice on the C57 BL/6 background were given either Ramipril (angiotensin converting enzyme inhibitor) or L-NAME salts from the ages of 4 to 7 weeks of age to induce a state of hypotension or hypertension, respectively. The top graph represents independent serial blood pressure measurements on 5 animals per group at the indicated ages (A). Blood pressure measurements were done using the non-invasive CODA2 tail cuff system. At 7 weeks this strain of Alport mouse is pre-proteinuric indicating a state prior to the onset of basement membrane destruction. The bottom graphs show Bosentan treatment reduces mRNA expression of MMP-10 (C), MMP-12 (B), MCP-1 (D), and TGFβ1 (D) in glomeruli from Alport mice. Glomerular RNA from Bosentan-treated and vehicle-treated 129 Sv wild type and Alport mice (once daily from 2 to 7 weeks of age, 100 mg/kg by oral gavage) was analyzed by real time RT-PCR for the indicated transcripts. MMP, matrix metalloproteinase; MCP-1, monocyte chemoattractant protein-1; TGFβ1, transforming growth factor beta-1.

To determine whether endothelin-1 expression is linked to biomechanical strain on the glomerular capillary walls pre-proteinuric X-linked Alport mice on the C57 Bl/6 background mice were treated with Ramipril, a commercially available angiotensin converting enzyme (ACE) inhibitor to make the animals hypotensive. A second cohort of animals was given L-NAME salts to make them hypertensive, and a third cohort was given drinking water with no additives. The effect of these treatments on blood pressure was confirmed directly using a CODA-2 tail cuff blood pressure monitoring device specifically designed for mice. The effect of these treatments was a significant elevation in blood pressures (both systolic and diastolic) when comparing ramipril-treated mice with salt-treated mice (FIG. 12). Kidney sections were dual stained with antibodies specific for endothelin-1 and CD31 (a marker for endothelial cells). Images of representative glomeruli are shown in FIG. 11. Note the fact that endothelin-1 expression is barely visible in glomeruli from Ramipril-treated mice (FIG. 11 (A)), while readily visible in untreated mice (FIG. 11 (C)). Immunostaining intensity is markedly increased in the L-NAME salt-treated animals relative to both other groups. Glomerular immunostaining intensity for CD31 did not vary between the treatment, but confirm that the endothelin-1 immunostaining is primarily in the endothelial cell compartment. Collectively, the data shows that endothelin expression is elevated with blood pressure in Alport glomerular endothelial cells. This was not observed in wild type glomeruli.

It is known that matrix metalloproteinases (MMPs), transforming growth factor beta 1 (TGF-β1), and monocyte chemoattractant protein-1 (MCP-1) contribute to the progression of Alport glomerular pathology (Cosgrove et al., 2000, *Am J Pathol;* 157(5):1649-59; Rao et al., 2006, *Am J Pathol;* 169(1):32-46; Eisberg et al., 2006, *PLoS Med;* 3(4):e100). 129 Sv autosomal Alport mice and wild type littermates were treated with 100 mg/kg Bosentan or with carboxymethlycellulose vehicle by oral gavage from 2 to 7 weeks of age. One kidney was prepared for immunohistochemistry, and the other used for glomerular RNA isolation. Real time RT-PCR analysis of glomerular RNA (FIG. 12) showed a significant reduction in the mRNA expression of MMP-10, MMP-12, TGF-β1, and IL-6 in glomeruli from Bosentan-treated Alport mice compared to Alport mice given vehicle. MMP-9 expression was not affected; however this MMP has been shown not to contribute to progression of Alport glomerular disease (Andrews et al., 2000, *Am J Pathol;* 157(1):303-11).

Figure 13:
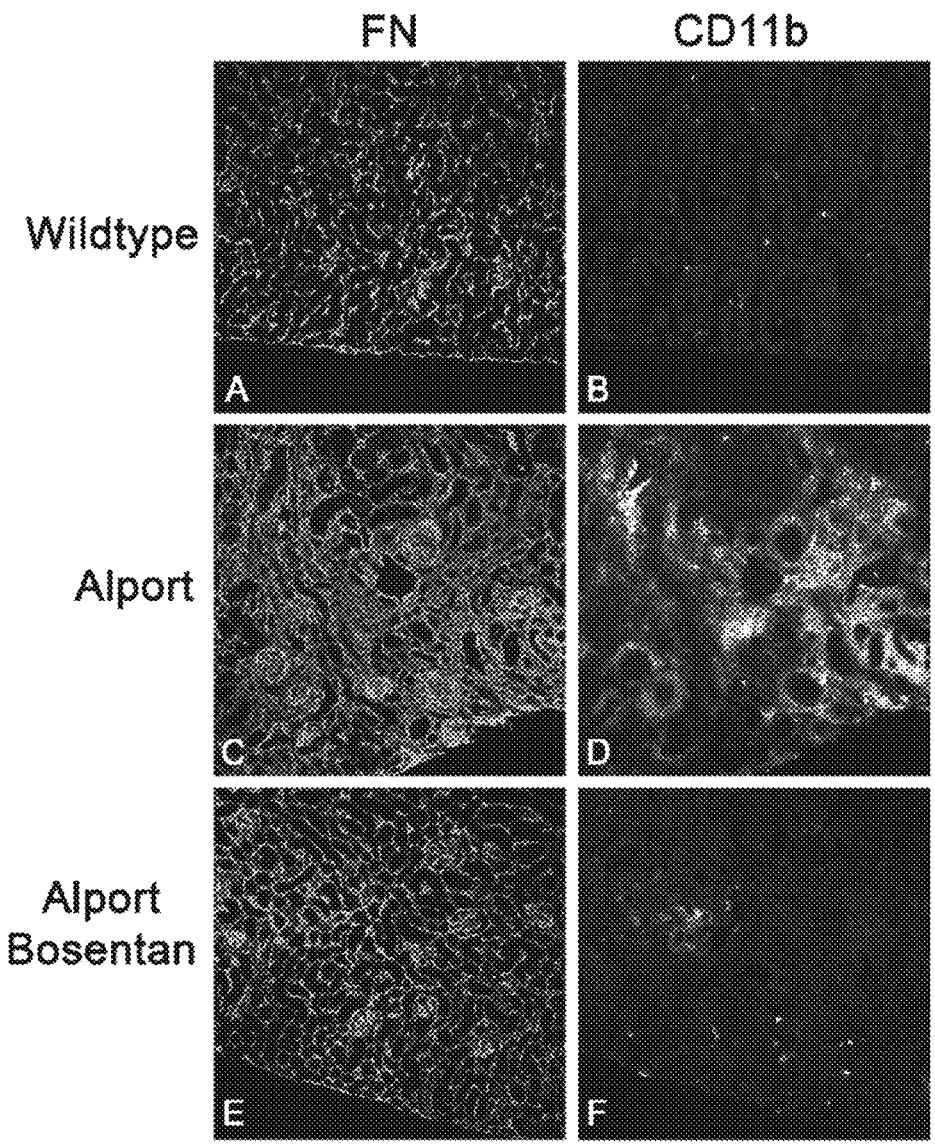
FIG. 13. Bosentan treatment ameliorates interstitial fibrosis and monocytic infiltration in Alport kidneys. Cryosections from Bosentan treated and vehicle treated wild type and Alport mice were immunostained with antibodies specific for fibronectin (A, C, and E) and CD11b (a monocyte marker) (B, D, and F).

Kidney cryosections from these same mice were immunostained using antibodies against fibronectin, to assess interstitial fibrosis, and CD11b, to assess the degree of monocytic interstitial infiltration. FIG. 13 shows that kidneys from vehicle-treated Alport mice showed significant renal scarring and massive monocytic infiltration, consistent with what is normally observed in this mouse model at 7 weeks of age. Bosentan treated mice showed near complete blockade of both interstitial fibrosis and monocytic infiltration, indicating a profound effect of endothelin receptor blockade on Alport renal disease.

Figure 14:
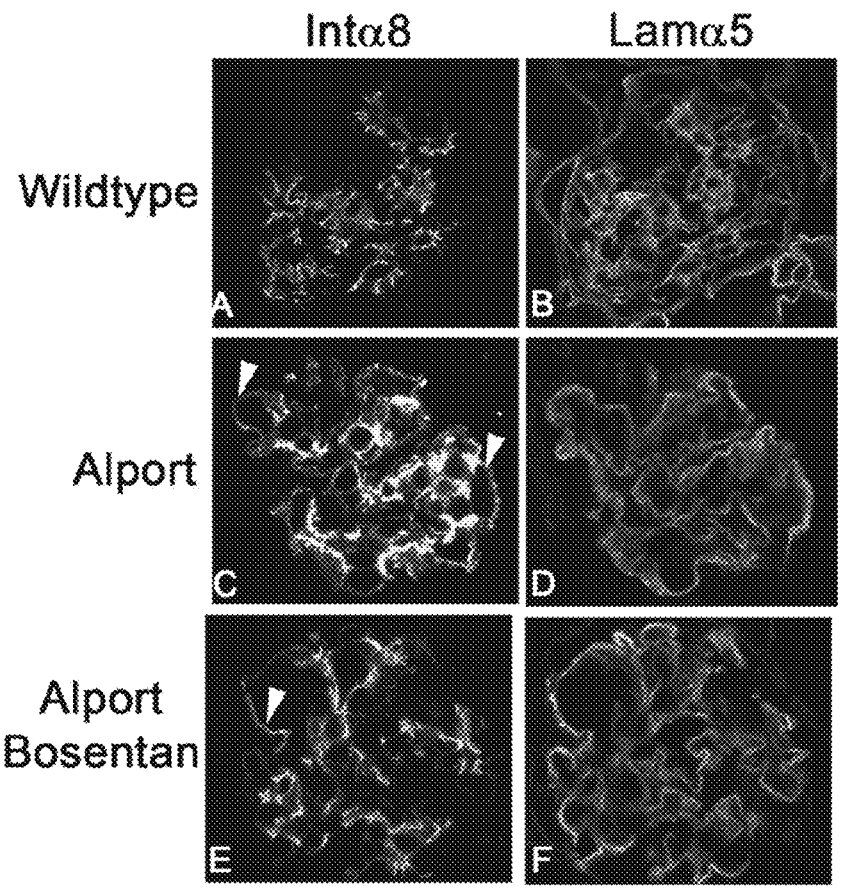
FIG. 14. Bosentan treatment blocks mesangial process invasion of Alport glomerular capillaries. Cryosections from wild type mice and Alport mice given either vehicle or Bosentan were immunostained using antibodies specific for integrin α8 (a mesangial cell surface marker) (A, C, and E) or laminin α5 (a marker for the glomerular basement membrane. (B, D, and E). Co-localization of the two markers (examples of which are denoted by arrowheads) indicate regions of the GBM infiltrated by mesangial processes.

Given the effect of endothelin activation on Rac1 and CDC42 activation, and given the showings of Example 1, showing mesangial process invasion of the glomerular capillaries in Alport mice (see also Zallocchi et al., 2013, *Am J Pathol;* 183(4):1269-80), one would expect that blockade would prevent or reduce mesangial process invasion of the glomerular capillaries in treated mice. FIG. 14 shows that for Alport mice given vehicle only, there is extensive mesangial invasion of the glomerular capillaries, as evidenced by the presence of integrin α8 immunostaining (a mesangial cell surface marker) in regions immunopositive for laminin α5 (a marker for the GBM). In Bosentan-treated Alport mice, integrin α8 immunostaining is largely localized to the mesangial matrix, with occasional interposition into the capillary loops observed (denoted by arrowhead).

Collectively, FIGS. 11-14 demonstrate that endothelin-1 is induced in Alport glomeruli by hypertension, and that endothelin receptor blockade with Bosentan reduces glomerular expression of MMPs and cytokines known to drive the progression of the disease, ameliorates fibrosis and interstitial monocytic infiltration, and blocks mesangial process invasion into the glomerular capillary loops. This pathway (endothelin blockade on Alport glomerular mesangial cells) represents a new etiology and thus a new use for the drug as a treatment for Alport glomerular disease.

Example 3

Endothelin Receptor A and Integrin α8 Co-Localization

Figure 15:
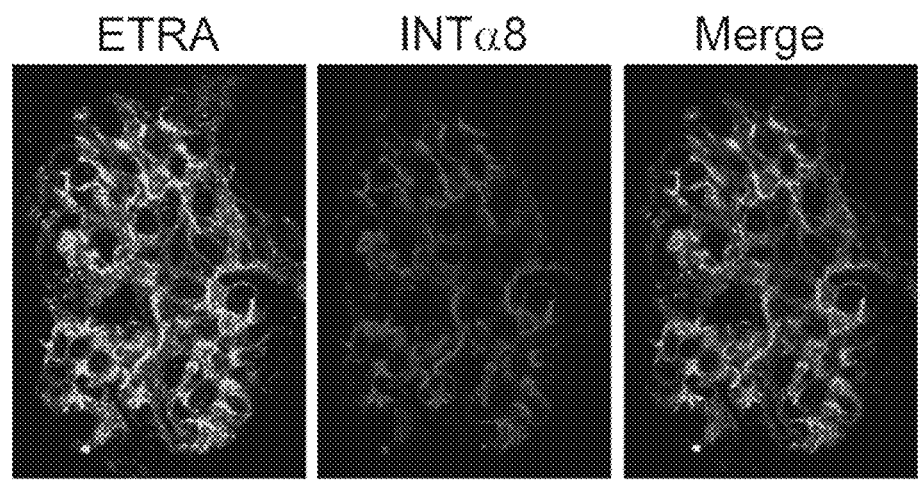
FIG. 15. The endothelin receptor A co-localizes with integrin α8, which shows it is abundantly expressed on mesangial cells in mice.

Using methods described in the examples included herewith, FIG. 15 shows that the endothelin receptor A co-localizes with integrin α8, which shows it is abundantly expressed on mesangial cells in mice. While this has been previously shown for rats, this example verifies the observation in mice, since our model is for paracrine activation of mesangial ETRA by endothelin-1 which is of endothelial cell origin.

Example 4

Laminin 211-Mediated Focal Adhesion Kinase Activation Triggers Alport Glomerular Pathogenesis It has been known for some time that laminin 211 and 111, normally restricted to the mesangial matrix, accumulate in the glomerular basement membranes (GBM) of Alport mice, dogs, and humans. This example shows that Laminin 211, but not laminin 111, activates focal adhesion kinase (FAK) on glomerular podocytes in vitro and in vivo. CD151-null mice also show progressive accumulation of laminin 211 in the GBM, and podocyte FAK activation. Analysis of glomerular mRNA from both models demonstrates significant induction of MMP-9, MMP-10, MMP-12, MMPs linked to GBM destruction in Alport disease models, as well as the pro-inflammatory cytokine IL-6. SiRNA knockdown of FAK in cultured podocytes significantly reduced expression of MMP-9, MMP-10 and IL-6, but not MMP-12. Treatment of Alport mice with TAE226, a small molecule inhibitor of FAK activation, ameliorated fibrosis and glomerulosclerosis, significantly reduced proteinuria and blood urea nitrogen levels, and partially restored GBM ultrastructure. Glomerular expression of MMP-9, MMP-10 and MMP-12 mRNAs was significantly reduced in TAE226 treated animals. Collectively, this work identifies laminin 211-mediated FAK activation in podocytes as an important early event in Alport glomerular pathogenesis and suggests that FAK inhibitors might be employed as a novel therapeutic approach for treating Alport renal disease in its early stages.

The pathologic glomerular basement membrane in Alport syndrome is irregularly thickened and thinned, with a multilaminar or "basketweave" appearance that is unique to the disease and a definitive diagnostic test for Alport syndrome (Kruegel et al., 2013, *Nat Rev Nephrol:* 9: 170-178). It has been shown that the thickened regions are more permeable to injected ferritin than the non-thickened regions of the GBM (Abrahamson et al., 2007, *J Am Soc Nephrol:* 18: 2465-2472). This property is consistent with a partially degraded matrix network, suggesting proteolytic damage may contribute to focal thickening of the Alport GBM. The type IV collagen network in Alport GBM is comprised entirely of $\alpha1(IV)/\alpha2(IV)$ chains, which contains fewer interchain crosslinks than the subepithelial $\alpha3(IV)/\alpha4(IV)/\alpha5(IV)$ network found in wild type GBM (Gunwar et al., 1998, *J Biol Chem;* 273: 8767-8775), and is more susceptible to proteolytic degradation by endogenously expressed matrix metalloproteinases (Rao et al., 2006, *Am J Pathol;* 169: 32-46; Zeisberg, et al., 2006, *PLoS Med;* 3: e1004.

Work on Alport renal disease thus far has focused on events that occur after glomerular disease is well established. The work includes roles for pro-inflammatory cytokines, such as TGF-β1 (Zeisberg, et al., 2006, *PLoS Med;* 3: e100), CTGF (Koepke et al., 2007, *Nephrol Dial Transplant;* 22: 1062-1069), and the mesangial adhesion molecule $\alpha1\beta1$ integrin (Cosgrove et al., 2000, *Am J Pathol;* 157: 1649-1659; Cosgrove et al., 2008, *Am J Pathol;* 172: 761-773), all of which contribute to the glomerular pathology in Alport syndrome. MMPs are also induced as a function of disease progression, and several MMPs, including MMP-2, MMP-9, and MMP-12 have been functionally linked to progressive destruction of the GBM (Rao et al., 2006, *Am J Pathol;* 169: 32-46; Zeisberg, et al., 2006, *PLoS Med;* 3: e100).

An unusual characteristic of Alport glomerular disease progression is the early and progressive deposition of abnormal laminins (laminin 211 and 111) in the GBM. While this phenomenon was first described many years ago (Cosgrove et al., 2000, *Am J Pathol;* 157: 1649-1659; Kashtan et al., 2001, *JAm Soc Nephrol;* 12: 252-260), the functional significance of this observation as it relates to molecular pathology in the glomerulus has remained unclear. As shown in Example, 1 laminin 211 in the GBM is deposited by invading mesangial cell processes, a process that may be triggered by biomechanical strain on the capillary tuft owing to the altered type IV collagen composition of the GBM. In this example work we identify FAK activation in podocyte foot processes specifically in regions of the GBM where abnormal laminin deposition is occurring. This is observed as early as P10, long before detectable proteinuria for Alport mice on the 129 Sv/J background, which is detectable at about 3 weeks of age (Cosgrove et al., 2000, *Am J Pathol;* 157: 1649-1659). We link FAK activation to elevated expression of MMP-9, MMP-10, MMP-12, and IL-6, all of which are implicated in the progressive GBM destruction associated with Alport glomerular disease. We demonstrate all of these phenomena are also observed in the CD151 knockout mouse, which has a specific defect in $\alpha3\beta1$ integrin binding affinity, a characteristic likely to impact the structural integrity of the capillary tuft as well (Zeng et al., 2006, *Cancer Res;* 66: 8091-8099). Importantly, the CD151 knockout mouse has a normal type IV collagen network in the GBM, which suggests that these events are not due to altered signaling resulting from the altered type IV collagen basement membrane composition in Alport GBM.

Materials and Methods

Animals. Alport mice were either autosomal recessive (COL4A3 mutant on the 129 Sv/J background (Cosgrove et al., 1996, *Genes Dev;* 10: 2981-2992). CD151 knockout mice were on the FVB background and were a gift from Martin Hemler, Harvard Medical School (Takeda et al., 2007, *Blood;* 109: 1524-1532). Laminin dy/dy mice were obtained from the Jackson Laboratories (strain #129P1/ReJ-Lama2dy/J, stock #000641). Age/strain matched wild type mice were used as controls. All animal work was done under an IACUC protocol approved by the BTNRH IACUC committee and in accordance with the USDA and NIH guidelines for the care and use of animals for research. Every effort was made to minimize stress and discomfort.

Antibodies and inhibitors. Anti-α-actinin-4 was from Santa Cruz Biotechnology, Inc (Dallas, Tex., USA, Cat #: SC-49333); anti-CD11b was from CedarLane Laboratories Limited (Honrby, Ontario, Canada, Cat #: CL8941AP); anti-Fibronectin was from Sigma (St. Louis, Mo., USA, Cat #: F3648); anti-Integrin α8 was from R&D Systems (Minneapolis, Minn., USA, Cat #: AF4076); anti-Laminin α1 was a gift from Dr. Dale Abrahamson (KU Medical Center, Kansas City, Kans., rat monoclonal 8B3); anti-Laminin α2 and anti-β actin were from Sigma (St. Louis, Mo., USA, Cat #: L0663); anti-Laminin α5 was a gift from Dr. Jeff Miner (Washington University, St. Louis, Mo.); anti-p-FAK$^{397}$ was from Assay Biotechnology (Sunnyvale, Calif., USA, Cat #: A0925) and from Invitrogen (Carlslab, Calif.); anti-Total FAK was from Cell Signaling Technology (Danvers, Mass., USA, Cat #: 3285). All Alexa-fluor conjugated secondary antibodies were from Invitrogen (Carlsbad, Calif.), including donkey anti-rat 488, donkey anti-rabbit 555, goat anti-rat 488, goat anti-rabbit 555, donkey anti-rabbit 488, and donkey anti-goat 568. The small molecular inhibitor for FAK activation, TAE226 was from Chem Scene (Monmouth Junction, N.J., Cat #CS-0594); the peptide inhibitor for NF-kappaB (SN-50) was from Calbiochem (now EMD Millipore, Billerica, Mass., Cat #481480).

Immunofluorescence microscopy. Fresh frozen kidneys were sectioned at 8-μm and acetone fixed. Sections were incubated overnight at 4° C. in primary antibody solution. The dual stain consisting of rat anti-mouse Laminin-α2 antibody (Sigma-Aldrich, St. Louis, Mo.) at 1:200 and rabbit anti-mouse phospho-FAK 397 antibody at 1:25 as well as the dual stain of goat anti-mouse Integrin α8 antibody (R & D Systems, Minneapolis, Minn.) at 1:1000 and rabbit anti-mouse Laminin-5 antibody, at 1:1000 were diluted in 0.3% PBST+5% FBS. Rabbit anti-mouse Fibronectin antibody at 1:300 and rat anti-mouse CD11b antibody at 1:100 were diluted in 7% Milk. Slides were rinsed with 1×PBS and incubated with the appropriate Alexa Fluor donkey secondary antibodies at 1:300 for 1 hour at room temperature. They were then rinsed again with 1×PBS and mounted with Vectashield Mounting Medium with DAPI (Vector, Burlingame, Calif.). The dual stain of mouse-anti rat Laminin α1 antibody at 1:300 and rabbit anti-mouse phospho-FAK 397 antibody at 1:25 were diluted in 0.3% PBST+5% NGS and incubated overnight at 4° C. Slides were rinsed with 1×PBS and incubated with the appropriate Alexa Fluor goat secondary antibodies at 1:300 for 1 hour at room temperature. They were then rinsed again with 1×PBS and mounted with Vectashield Mounting Medium with DAPI.

Primary Mesangial Cells were derived and characterized as previously described (Cosgrove et al., 2008, *Am J Pathol;* 172: 761-773). Three independent Transwell Migration Assays were performed using 0.5 µM TAE226 as previously described. For pFAK Western Blot[397], cells were maintained on 1% FCS-containing media for two days, overnight in 0.1% BSA (Fraction V, Roche Diagnostics, Mannheim, Germany) and TAE226 added to 0.5 and 1.0 µM. After five hours protein was collected in M-PER™ (Thermo Scientific, Rockford, Ill.) containing Protease Inhibitor Cocktail P8340 at 1:100 (Sigma, St. Louis, Mo.), 5 mM Sodium Fluoride (Sigma), and 2 mM Sodium Orthovanadate (Sigma) and Western Blots run as described below.

Conditional Immortalized Glomerular Epithelial Cells (GEC's), previously derived and characterized (Rao et al., 2006, *Am J Pathol;* 169: 32-46), were grown under permissive conditions (10% FCS, 10 U/ml γ-interferon at 33° C.). Stable FAK and Scrambled Knock-Down GEC's were established as follows: 8.5 million cells were electroporated in 0.5 mls Gene PULSER™ Electroporation buffer (Bio-Rad Laboratories, Hercules, Calif.) containing 20 µg SILENCER™ 4.1 CMV neo (Ambion, Austin, Tex.) plasmid expressing Ptk2 or scrambled siRNA, at 0.220 kV, 1.00 (µF×1000) in a 4 mm gap cuvette and incubated for 10 minutes on ice. Cells were plated under permissive conditions and 2 mg/ml G418 (Invitrogen, Carlsbad, Calif.) was added three days later. G418 selection was maintained for two weeks and clonal populations of selected cells generated by "limiting-dilution." RNA and protein was collected from expanded clonal populations placed under "non-permissive" conditions (5% FCS, no γ-interferon at 37° C.) for two weeks, using TRIZOL™ (Invitrogen) and M-PER™ (Thermo Scientific), respectively. Plasmid(s) Expressing siRNA's were constructed using Ambion Silencer™4.1-CMV neo, AMBION SILENCER™ Select siRNA Ptk2 (ID s65838) and Negative Control #1 (cat# AM4611) sequence(s) as per manufacturer's direction.

NF-κB Staining and −/+ Stretch pFAK397 Western Blot. GEC's were differentiated under "non-permissive" conditions for ten days, plated onto Bioflex 6-well plates (Flexcell International, Hillsborough, N.C.) coated with Collagen Type 1 (rat tail, BD Biosciences, Bedford, Mass.)/Placental Laminin (Sigma), cultured for two days in 0.5% FCS and exposed to mechanical strain for 4 hours, as previously described (Meehan et al., 2009, *Kidney Int;* 76: 968-976). For NF-κB Staining, cells were fixed with 2% PFA, 4% Sucrose in PBS for 10 minutes, permeabilized with 0.3% Triton, as previously described (Rao et al., 2006, *Am J Pathol;* 169: 32-46) incubated with αNF-κB P65 antibody at 1:50 overnight at 4° C., incubated with anti-rabbit secondary antibody at 1:750 for two hours at room temperature, gaskets were cut out, mounted on slides with VECTASHIELD™ (Vector Laboratories, Burlingame, Calif.) and cover slipped. For −/+ Stretch pFAK Western, protein was collected in M-PER (Thermo Scientific) as above and Western Blot run as described below.

NF-κB SN50, Inhibitor Peptide Treatment, GEC's were cultured as described above, 10 µM NF-κB SN50 Inhibitor Peptide (EMD Millipore, Billerica, Mass.) was added (and after one additional hour) exposed to 20 hours of mechanical strain and RNA collected as previously described (Meehan et al., 2009, *Kidney Int;* 76: 968-976).

Basal Lamina and −/+ TAE226 pFAK[397] Western Blots. 10 day differentiated GEC's were cultured in 0.5% FCS for 2 days and plated onto tissue culture dishes previously coated with 50 µg/ml Collagen Type 1 Rat Tail (BD Biosciences) and 2 µg/cm² Placental Laminin (Sigma) in 0.1% BSA containing media. For Basal Lamina experiment, additional dishes were coated with Collagen Type 1 and 1.25 µg/cm² EHS Laminin (BD Biosciences) or 1.25 m/cm² Merosin (Chemicon, Temecula Calif.). For −/+ TAE266 experiment, 20 µM TAE226 was included in the media. Protein was collected 15 hours later in M-PER (Thermo Scientific) as above and Western Blot run as described below.

Confocal microscopy. Slides were cover slipped using Vectashield mounting medium containing DAPI to counterstain the nuclei (Vector, Burlingame, Calif.) and confocal images captured using a Zeiss AxioPlan 2IF MOT microscope interfaced with a LSM510 META confocal imaging system, using a 63×NA:1.4 oil objective. Final figures were assembled using Adobe Photoshop and Illustrator software (Adobe Systems, CA).

Glomerular isolation. Glomeruli were isolated by perfusing animals with magnetic beads and isolating the glomeruli using a magnet as described previously (Rao et al., 2006, *Am J Pathol;* 169: 32-46).

Real time qRT-PCR. Total RNA was reverse transcribed using SUPERSCRIPT® III (Invitrogen, Life Technologies, Grand Island, N.Y.) with Oligo(dT)$_{20}$ Primer (Invitrogen). The real time PCR was carried out using TAQMAN® Gene Expression Master Mix (Applied Biosystems, Life Technologies, Grand Island, N.Y.), and quantified using STEPONEPLUS™ Real-Time PCR System (Applied Biosystems). Samples were normalized to Mouse GAPDH Endogenous Control VIC® Probe (Applied Biosystems catalogue #4352339E) which was run alongside MMP-9 (Catalog #4331182, ID# Mm00442991_m1), MMP-10 (Catalog #4331182, ID# Mm00444630_m1), MMP-12 (Catalog #4331182, ID# Mm00500554_m1), IL-6 (Catalog #4331182, ID# Mm00446190_m1), NFKbia (Catalog #4331182, ID# Mm00477798_m1), and FAK (Catalog #4331182, ID# Mm00433209_m1) TAQMAN® Gene Expression Assay Probes (Applied Biosystems). Samples were run in triplicate with a final reaction volume of 20 ul with the following cycling parameters: 50° C. for 2 min, 95° C. for 10 min, followed by 40 cycles of a two-step PCR consisting of 95° C. for 15 s and 60° C. for 1 min. Relative changes in gene expression were determined by calculating the fold change using the comparative $C_T$ method of $2^{-\Delta\Delta C_T}$. Data are expressed as the mean with standard deviation for at least four independent RNA samples per data point.

Immunoblotting. Ten to fifteen micrograms, of cellular protein, was resolved in a 10% SDS-PAGE and then electrotransfered to PVDF membrane. The membranes were cut in half and the upper half (250 kDa to 75 kDa) used for pFAK/tFAK immunoblotting while the bottom half used for β-actin immunoblotting (loading control). Conditions for pFAK detection: the membrane was blocked in milk blocking solution (5% milk containing 0.2% Tween-20 in PBS) for 1 hour at room temperature with constant shaking and incubated overnight at 4° C. with anti-pFAK 1:1,000 in BSA blocking solution (1% BSA containing 0.2% Tween-20 in PBS). After several washes the membrane was incubated with a goat anti-rabbit HRP conjugated secondary antibody in BSA blocking solution, dilution 1:20,000 for 1 hour at room temperature. Conditions for tFAK detection: the same membrane used for pFAK immunoblot was stripped and re-probed for tFAK. The blocking was done in 5% milk blocking solution for 1 hour at room temperature, followed by an overnight incubation with the tFAK primary antibody, dilution 1:500 in milk blocking solution. After several washes the membrane was incubated with a goat anti-rabbit HRP conjugated secondary antibody in 5% milk, dilution 1:3,000 for 1 hour at room temperature. Conditions for β-actin detection: the membrane was blocked for 1 hour with 10% milk blocking solution and then incubated overnight with the mouse anti-β-actin dilution 1:2,000 in the same blocking solution. After several washes the membrane was incubate with a goat anti-mouse HRP-conjugated secondary antibody, dilution 1:3,000 in 10% milk for 1 hour at room temperature. After several washes the membrane was developed using PIERCE® ECL Western Blotting Substrate (Thermo Scientific, Rockford, Ill.) as per manufacturer's direction.

Treatment of mice with TAE226. Four Col 4A3 knockout mice from 129 Sv/J background were given 50 mg/Kg TAE226 (ChemScene, LLC Monmouth Junction, N.J.) 1× daily by gavage needle starting at two weeks of age until seven weeks old. The TAE226 was diluted in a 0.5% carboxy methyl cellulose suspension. Three control Col 4a3 knockout mice of the same age were given 0.5% CMC suspension alone and served as controls.

Albumin and creatinine assays. Urine was collected weekly and albumin concentrations were analyzed as instructed using a mouse albumin ELISA kit #MSAKT from Molecular Innovations (Novi, Mich.). Albumin levels were normalized to creatinine using QuantiChrom Creatinine Assay Kit (DICT-500) (BioAssay Systems, Hayward, Calif.) as instructed.

Transmission electron microscopy. Transmission electron microscopy was performed as described previously (Cosgrove et al., 2000, *Am J Pathol;* 157: 1649-1659).

Statistical analysis. Data were analyzed using the one sample Students t-test with Bonferroni correction.

Results

Figure 16:
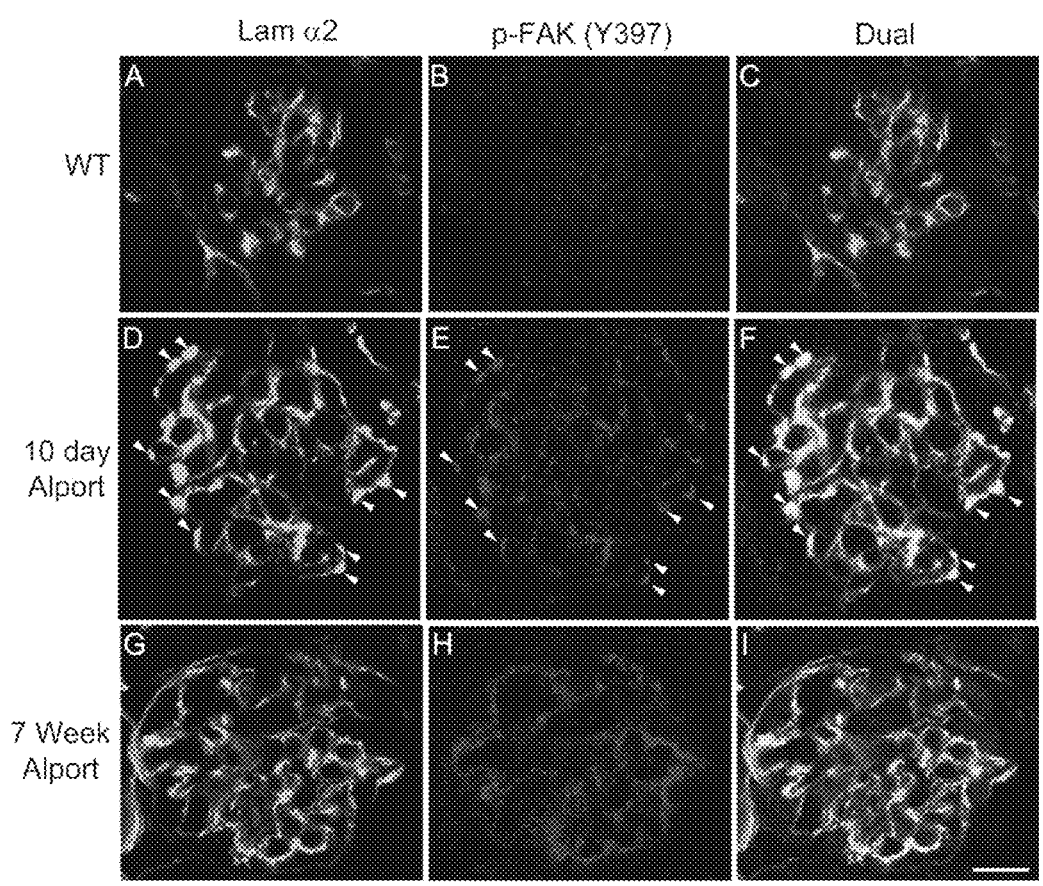
FIG. 16. Activation of focal adhesion kinase occurs specifically in regions of the GBM where laminin α2 is present, and is a very early event in Alport glomerular pathogenesis. Cryosections from 10 day old Alport mice (D-F), 7 week old Alport mice (G-I), and wild type littermates (A-C) were immunostained with antibodies specific for the α2 chain of laminin or pFAK$^{397}$. Arrowheads denote areas of dual immunostaining in the glomerular capillary loops. Scale bar=15 μm.

In earlier work we and others showed that laminin 211 accumulates in the GBM of Alport mice, dogs and humans (Cosgrove et al., 2000, *Am J Pathol;* 157: 1649-1659; Kashtan et al., 2001, *J Am Soc Nephrol;* 12: 252-260). FIG. 16 shows that the appearance of laminin 211 in the GBM correlates with the activation of FAK in glomerular podocytes. FIG. 16 (A-C) shows that in wild type mice laminin 211 is restricted to the mesangium and no appreciable level of FAK activation (as determined by immunostaining for pFAK$^{397}$) is observed. As early as 10 days of age in 129 Sv/J autosomal Alport mice we begin to observe punctate immunostaining for laminin 211 in the GBM of some (30-50%) glomeruli (FIG. 16 (D), arrowheads). Wherever we observe GBM laminin staining we also see immunopositivity for pFAK$^{397}$ (FIG. 16 (E-F)), indicating activation of FAK specifically in regions of the GBM where laminin 211 has been deposited. By 7 weeks of age in Alport glomeruli, laminin 211 is more extensively observed in the GBM (FIG. 16 (G)), and continues to co-localize with pFAK$^{397}$ immunostaining (FIG. 16 (G-I)).

In addition to laminin 211, laminin 111 has also been shown to accumulate in the GBM of Alport mice (Abrahamson et al., 2003, *Kidney Int;* 63: 826-34). To determine whether laminin 211 and/or laminin 111 is responsible for activation of FAK in glomerular podocytes we crossed the 129 Sv/J autosomal Alport mouse with a laminin α2-deficient mouse (a model for muscular dystrophy), also on the 129 Sv/J background. As evidenced in FIG. 17, while the 7 week old Alport mouse shows FAK activation in podocytes bound to laminin 111-immunopositive GBM (FIG. 17 (A-C)), the age matched laminin α2-deficient Alport mouse (DY Alport), while immune-positive for laminin 111 (FIG. 17 (D)), does not show appreciable FAK activation anywhere in the glomerulus (FIG. 17 (E)). To assess in a more direct manner whether laminin 211 activates FAK in podocytes, we cultured differentiated conditionally immortalized podocytes on placental laminin (primarily laminin 521), EHS laminin (laminin 111), and merosin (laminin 211) for 15 hours and analyzed cell lysates for total FAK and pFAK$^{397}$. The results in FIG. 17 (G) show higher levels of pFAK$^{397}$ in podocytes cultured on merosin compared to either placental laminin or EHS laminin, indicating that laminin 211 can activate FAK directly in these cells.

Figure 18:
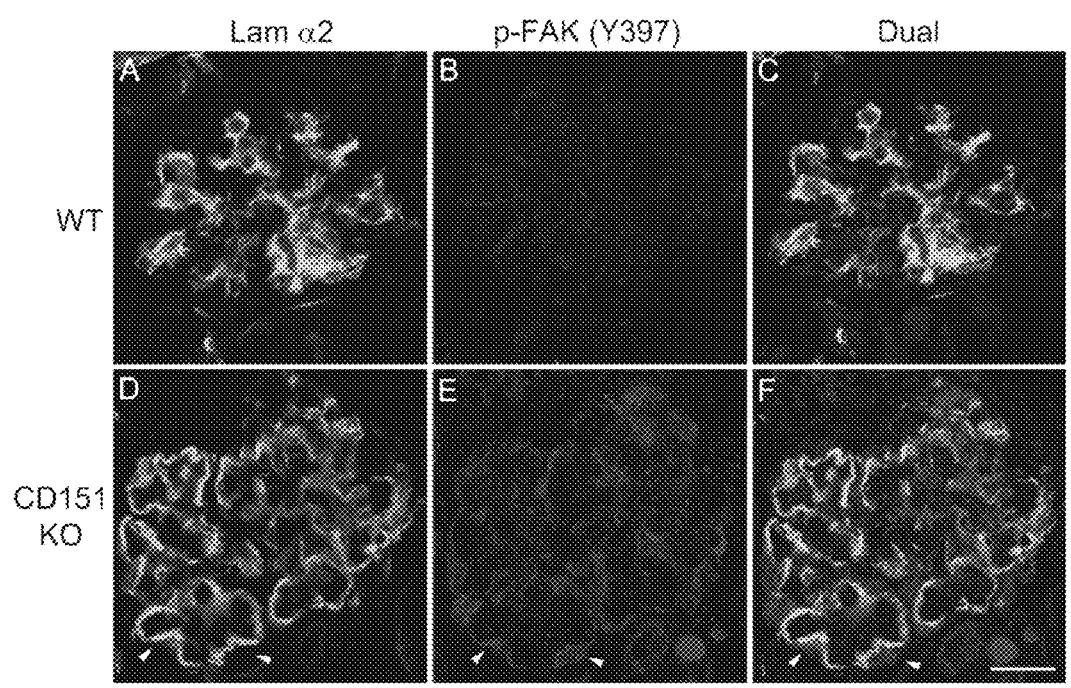
FIG. 18. Activation of focal adhesion kinase occurs specifically in regions of the GBM where laminin α2 is present in CD151 knockout mice. Cryosections from 10 week old CD151 knockout mice (D-F) and wild type littermates (A-C) were immunostained with antibodies specific for the α2 chain of laminin or pFAK$^{397}$. Arrowheads denote areas of dual immunostaining along the capillary loops. Scale bar=15 µm.

As shown in Example 1, laminin 211 also accumulates in the GBM of CD151 knockout mice (see also Zallocchi et al., 2013, *Am J Pathol;* 183: 1269-80). If laminin 211 is responsible for FAK activation on glomerular podocytes in vivo we would expect to observe pFAK$^{397}$ immunostaining at the interface of podocyte binding to the GBM in these mice as well. FIG. 18 shows that this is indeed the case. FIG. 18 (D-F) clearly demonstrates laminin 211 immunostaining in the GBM with clear presence of pFAK$^{397}$ in podocytes adjacent to laminin 211-immunopositive GBM, consistent with laminin 211 mediated FAK activation in the podocytes of CD151 knockout mice.

Figure 19:
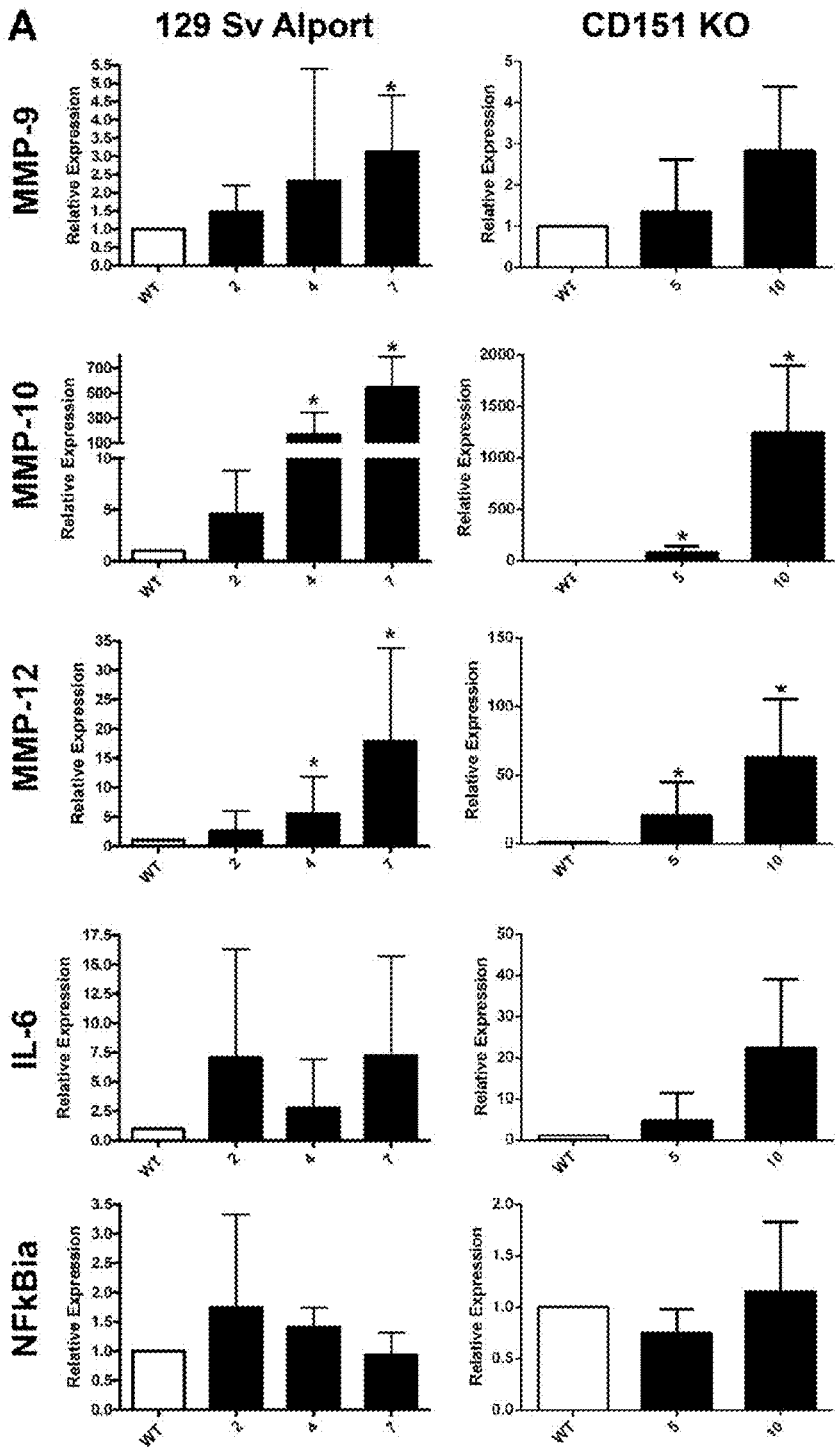
FIG. 19. Induction kinetics for MMP-9, MMP-10, MMP-12, IL-6, and NF-kappaB in glomeruli from Alport mice and CD151 knockout mice. A) Glomeruli were isolated from CD151 knockout mice and Alport mice along with strain/age matched wild type littermates at the indicated ages using magnetic bead isolation. Total glomerular RNA was analyzed by real time RT-PCR using primers specific for the indicated transcripts. Each data point represents at least five independent samples. Significant differences when comparing the data from mutants with wild type littermates are denoted with asterisks (p<0.05). Note that IL-6 and NF-kappaB did not reach significance likely due to a large variance in the data, but trended towards significance. B) MMP-10 protein is induced in Alport glomeruli at both 4 and 7 weeks of age as determined by immunofluorescence analysis. Scale bar=15 µm.
Figure 19:
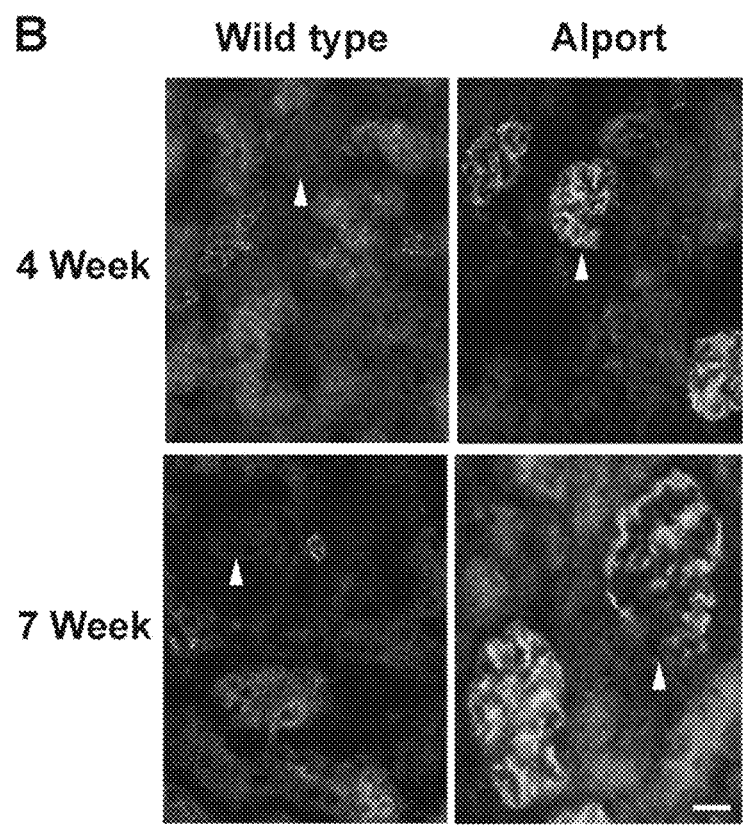

A clear link between the induction of matrix metalloproteinases and glomerular basement membrane damage has been demonstrated in Alport mice (Rao et al., 2006, *Am J Pathol* 169: 32-46; Zeisberg et al., 2006, *PLoS Med* 3: e100; 9; and Cosgrove et al., 2008, *Am J Pathol* 172: 761-773). Based on Affymetrix analysis of wild type and Alport glomerular RNA from 129 Sv/J mice, it was determined that MMP-9, MMP-10, and MMP-12 were significantly induced in the Alport glomeruli. MMP-10 and 12 are massively induced (700- and 40-fold, respectively), suggesting that these MMPs might be principally responsible for the GBM damage observed in Alport mice. Given that previous studies in other systems have linked FAK activation to the induction of MMPs (Zeng et al., 2006, *Cancer Res;* 66: 8091-8099; Van Slambrouch et al., 2007, *Int J Oncol;* 31:1501-1508), it was determined if a parallel dysregulation in glomerular RNA from Alport mice and CD151 knockout mice could be observed. Glomerular mRNA expression was profiled for a time course in both models using real time qRT-PCR. The results in FIG. 19 (A) demonstrate significant and progressive induction of all three MMPs in both models. The strikingly robust induction of MMP-10 and MMP-12 observed in Alport glomeruli is also observed in the CD151 knockout mouse, suggesting that these transcripts are induced via the laminin 211-mediated FAK activation pathway. Since earlier work demonstrates FAK-mediated induction of MMPs via activation of NF-kappaB (Chen et al., 2009, *J Cell Physiol;* 221: 98-108; Oh et al., 2009, *Gynecol Oncol;* 114: 509-515), NF-kappaBia transcript, which serves as an indicator for the state of NF-kappaB activation (Bottero et al., 2003, *Mol Diagn;* 7: 187-194), was also observed. As shown in FIG. 19 (A), this transcript trends higher in glomerular RNA for both models, as does the message encoding the NFkappaB-responsive pro-inflammatory cytokine IL-6 (Tseng et al., 2010, *J Cell Physiol;* 223: 389-396). Neither transcript shows significant induction due to a high degree of variability in abundance, likely owing to multiple pathways (in addition to FAK) converging on the activation of NF-kappaB.

MMP-10 expression in the glomerulus has not been previously documented. To further qualify the validity of the qPCR results, we analyzed cryosections of 4 and 7 week old wild type and Alport mice for MMP-10 expression by immunofluorescence. The results in FIG. 19 (B) show that MMP-10 is not detected in wild type glomeruli, but is robustly expressed in Alport glomeruli at both early and advanced disease states.

Figure 20:
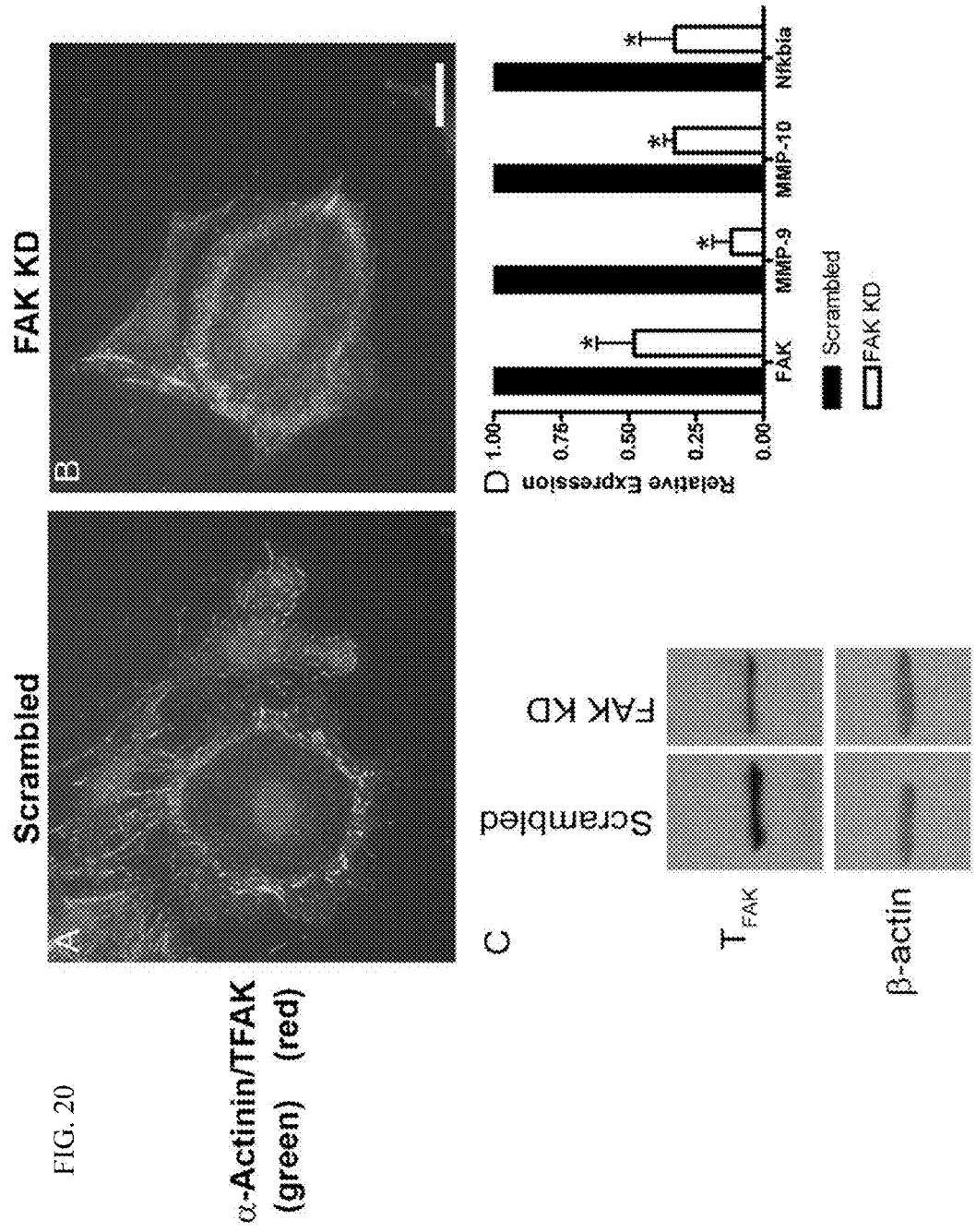
FIG. 20. Stable siRNA knock-down of FAK in cultured podocytes results in significantly reduced expression of MMP-9, MMP-10, and NF-kappaB. Conditionally immortalized podocyte cell cultures were transfected with vector encoding a siRNA expression cassette for FAK. A vector encoding a scrambled siRNA was used as a control. Stable clones were selected and propagated. The data presented is representative of several independently selected clones. A-B) While while cells expressing the scrambled vector still have robust focal adhesions (A), they are significantly reduced or absent in the cells expressing the FAK siRNA (B). C) Western blot for total FAK confirms a reduction of FAK protein in the FAK siRNA transfected cultures. D) Real time qRT-PCR analysis of RNA from these clones shows a significant reduction in the expression of mRNAs encoding FAK, MMP-9, MMP-10, and NF-kappaBia in FAK siRNA expressing cells versus those expressing the scrambled siRNA. Scale bar=15 µm.

To more directly establish the link between FAK activation and MMP gene expression in glomerular podocytes we performed siRNA knockdown of FAK in conditionally immortalized podocyte cell cultures. Stable clonal populations of siRNA knockdown podocyte cell lines were established. FIG. 20 shows results typical for several clones examined. In FIG. 20 (B), note the relative absence of focal adhesions in podocytes cultured on rat tail collagen relative to the parent podocyte cell line shown in FIG. 20 (A). FIG. 20 (C) shows that total FAK protein is reduced in extracts from the siRNA knockdown cells relative to cells transfected with a scrambled siRNA construct. FIG. 20 (D) shows that FAK knockdown cells show significantly reduced expression of MMP-9, MMP-10, and NF-kappaBia, confirming the link between FAK activation and induction of these MMPs in glomerular podocytes. Interestingly MMP-12 was not significantly reduced in the knockdown cells.

Figure 21:
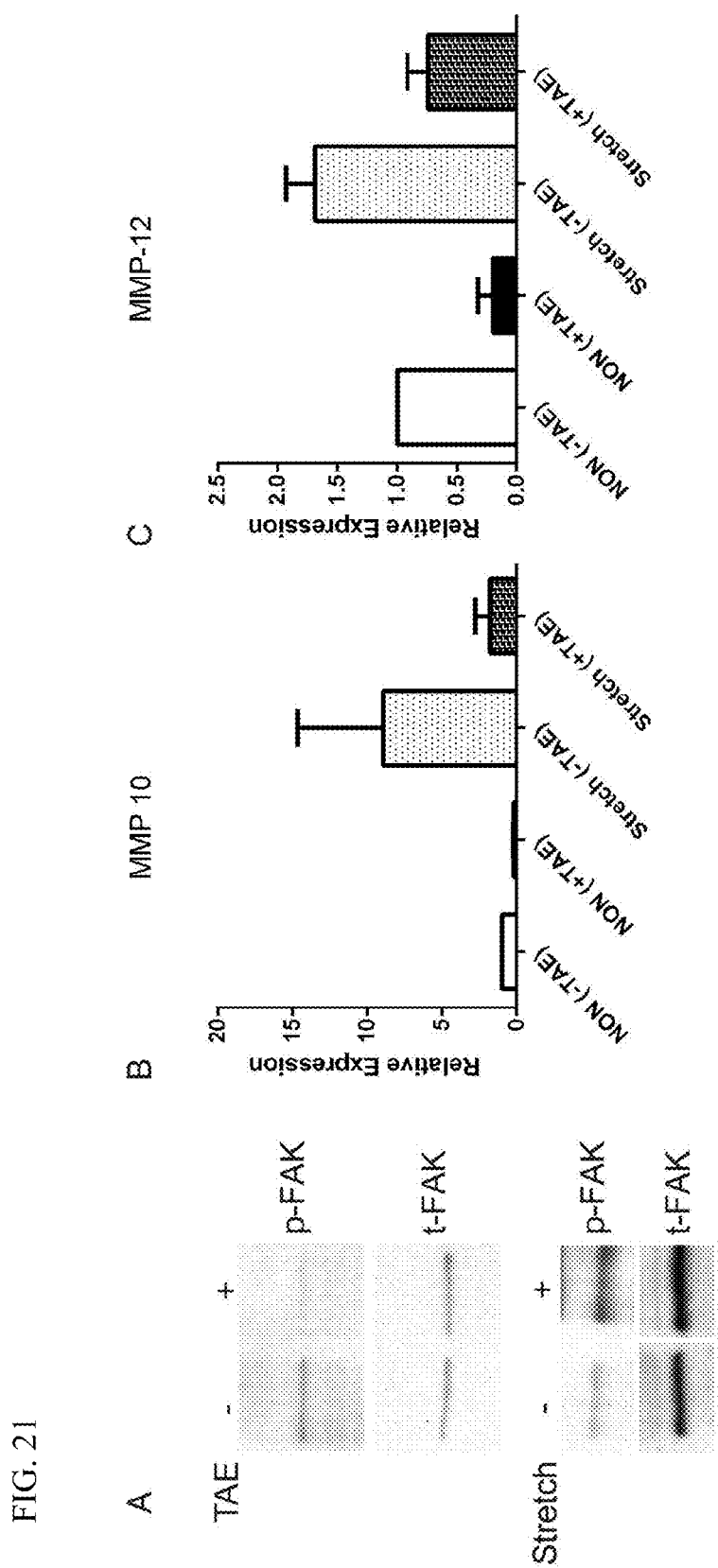
FIG. 21. The small molecule inhibitor for FAK, TAE226, reduces FAK activation and stretch-induced MMP-10 and MMP-12 expression in cultured podocytes. A) Podocytes were cultured on placental laminin in the presence or absence of TAE226 overnight. Extracts were prepared and analyzed by western blot for expression of pFAK397 and total FAK. FAK activation was also analyzed by western blot of podocyte extracts from stretched and non-stretched cells, demonstrating that biomechanical stretching directly activates FAK. B-C) Cells were treated or not with TAE226 under static and stretched conditions and mRNA analyzed by real time qRT-PCR for the indicated transcripts.

An alternative means of reducing FAK activation is by way of small molecule inhibitors. One such inhibitor, TAE226 has been shown to protect against glomerular injury by either lipopolysaccharide or anti-GBM antibody administration. Podocytes were cultured in the presence or absence of TAE226 to assess the effect on MMP expression. As shown in FIG. 21 (A) shows that treatment of cultured podocytes with TAE226 reduced the activation state of FAK and that FAK is directly activated by biomechanical stretching of podocytes as determined by western blot for pFAK397 protein. FIG. 21 (B-C) shows that, in contrast to the siRNA knockdown studies, both MMP-10 and MMP-12 show reduced expression in podocytes cultured with TAE226 relative to untreated cells. Since we have previously documented a role for biomechanical strain in the induction of MMPs and the acceleration of glomerular disease in Alport mice (Zallocchi et al., 2013, *Am J Pathol;* 183: 1269-80; Meehan et al., 2009, *Kidney Int;* 76: 968-976) we also assessed the effect of FAK inhibition by TAE226 on biomechanical stretch-mediated induction of MMP-10 and MMP-12. FIG. 21 (B-C) shows, consistent with our earlier findings, that biomechanical stretch induced both MMP-10 and MMP-12, and that message levels for these two MMPs are reduced in cells stretched in the presence of TAE226 relative to untreated cells.

Figure 22:
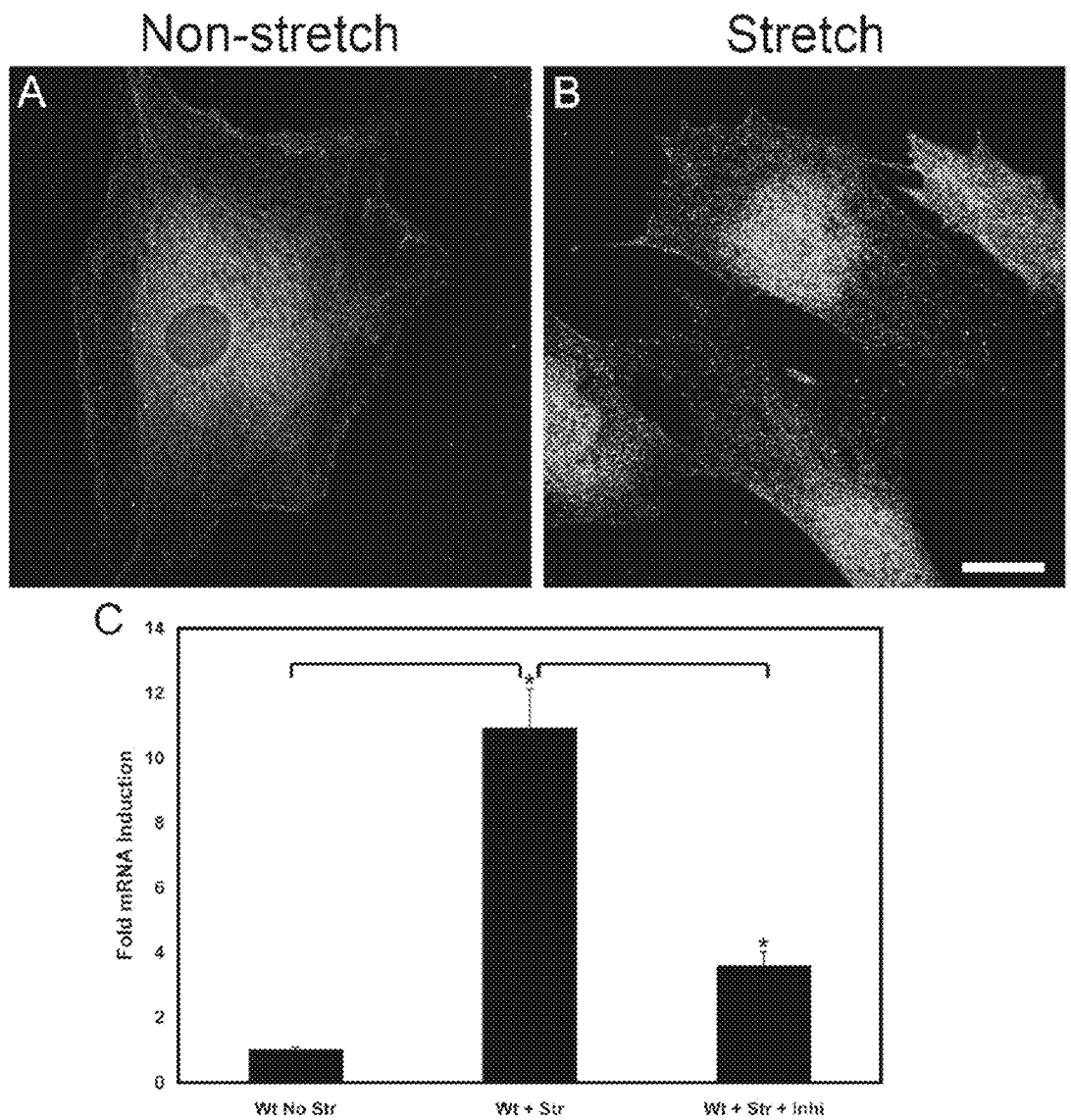
FIG. 22. Biomechanical stretching activates NF-kappaB which regulates MMP-10 expression in cultured podocytes. A) NF-kappaB localizes primarily to the cytosol in non-stretched cultured podocytes. B) Subjecting the cells to cyclic biomechanical stretching results in the nuclear localization of NF-kappaB, which is consistent with its activation. C) Stretch-mediated induction of MMP-10 is blocked by addition of a peptide inhibitor for NF-kappaB to the culture medium. Scale bar=20 µm.

FIG. 22 shows that biomechanical stretching activates NF-kappaB as evidenced by the nuclear localization of NF-kappaB in FIG. 22 (B) relative to non-stretched cells shown in FIG. 22 (A). Stretch-mediated induction of MMP-10 is attenuated by treating cells with a peptide inhibitor for NF-kappaB during the cyclic mechanical stretching (FIG. 22 (C)), demonstrating that MMP-10 induction is indeed mediated by NF-kappaB activation.

Figure 23:
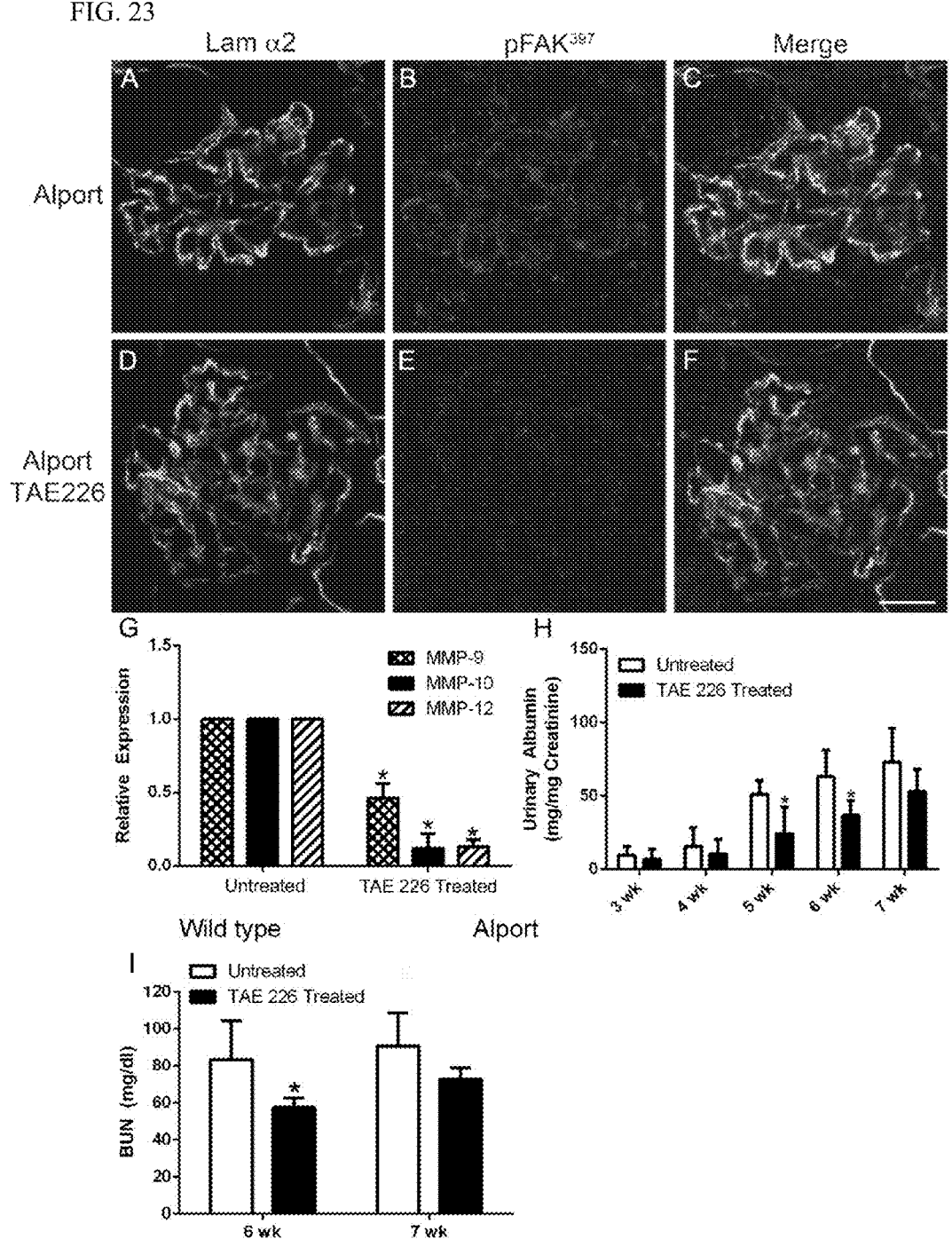
FIG. 23. Treatment of Alport mice with the small molecule inhibitor for FAK, TAE226, blocks FAK activation, significantly reduces glomerular expression of MMP-9, -10, and -12, and ameliorates proteinuria and blood urea nitrogen levels. 129 Sv/J autosomal Alport mice were treated with TAE226 from 2 to 7 weeks of age. A-F) While pFAK397 immunostaining is present in podocytes adjacent to laminin 211-immunopositive basement membranes in vehicle treated mice, it is absent in mice treated with TAE226, indicating effective blockade. G) Real time qRT-PCR analysis of glomerular RNA shows significant reduction in expression of MMP-9, MMP-10, and MMP-12 in TAE226 treated mice relative to those given vehicle. G-I) Significant amelioration of proteinuria and BUN in treated mice at 6 weeks of age, indicative of improved glomerular function, however the values loose significance at 7 week of age. Scale bar=15 µm.

To determine the role of laminin 211-mediated FAK activation on the progression of glomerular disease autosomal Alport mice were treated with TAE226 from 2 weeks of age (before the onset of proteinuria) to 7 weeks of age (near end stage). One kidney was used for glomerular RNA isolation by perfusion with magnetic beads, and the other prepared for histological and TEM analysis. FIG. 23 shows FAK activation in podocytes adjacent to laminin 211 in the Alport GBM (denoted with arrowheads). Treatment with TAE226 abolished pFAK immunostaining (D and F) demonstrating effective in vivo blockade of FAK activation achieved through drug treatment. FIG. 23 (G) shows that FAK inhibition significantly reduced the mRNA expression levels for MMP-9, MMP-10, and MMP-12 relative Alport mice given vehicle. FIG. 23 (H-I) show a significant reduction in proteinuria and blood urea nitrogen levels in treated Alport mice relative to Alport mice given vehicle at 6 weeks of age, but the numbers, while trending lower, loose significance by 7 weeks of age. Lifespan studies were not conducted because TAE226 treatment resulted in growth stunting indicating a toxic side effect.

Figure 24:
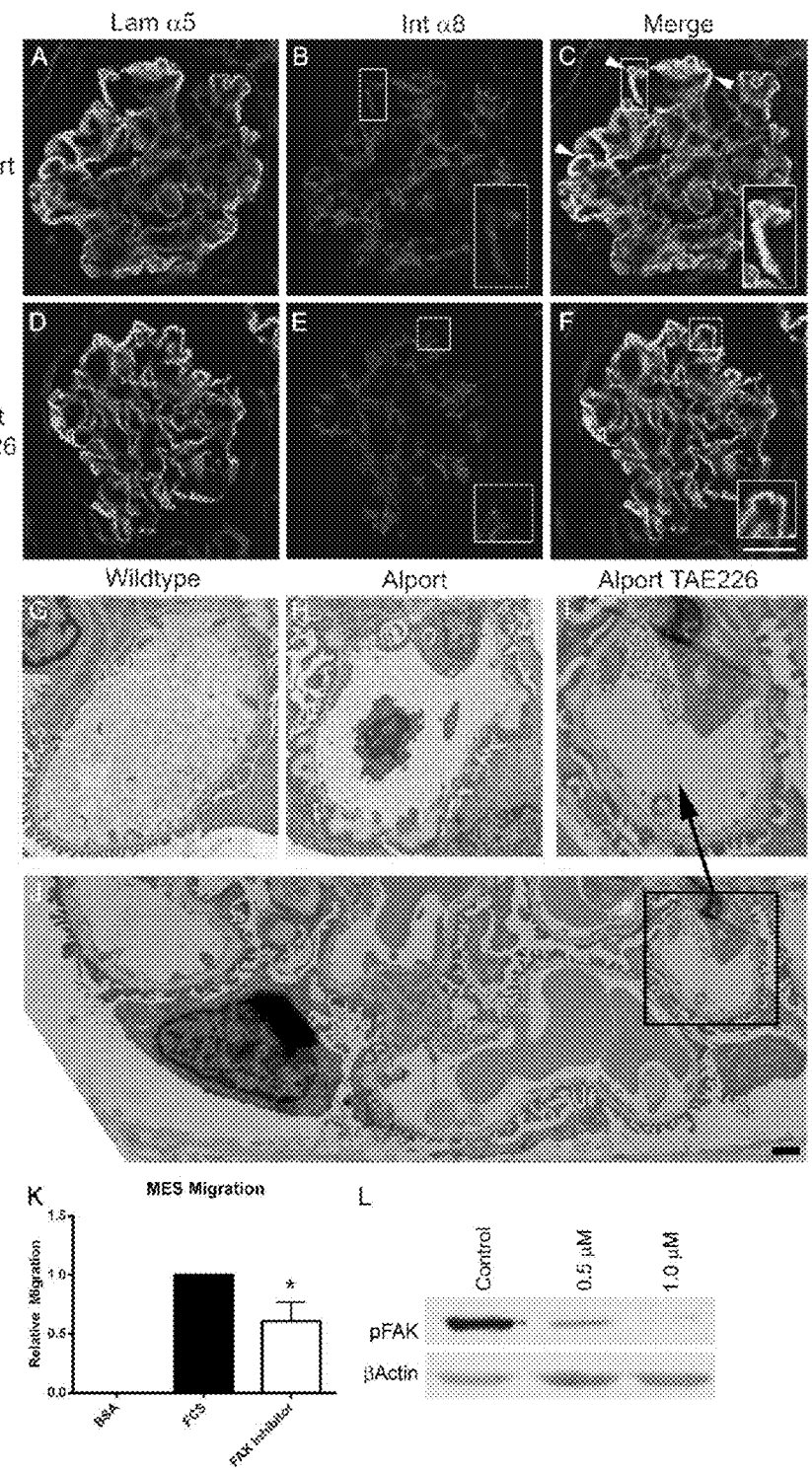
FIG. 24. Treatment of Alport mice with TAE226 reduces mesangial process invasion of the glomerular capillary loops, ameliorates GBM ultrastructural dysmorphology, and significantly reduces pFAK activation and migratory potential of primary cultured mesangial cells. A-F) The same mice as in FIG. 23 were dual immunostained with the GBM marker laminin α5 (A and D), and the mesangial cell marker integrin α8 (B and E). (C) and (F) represent a merging of results obtained from staining with laminin α5 and integrin α8. Arrowheads in C denote regions where invasion of the capillary loops by mesangial processes is evident (inserts in B and C). This characteristic is markedly reduced in the TAE226-treated glomeruli where integrin α8 immunostaining is restricted to the mesangial angles (inserts in E and F). G-J) Transmission electron microscopic analysis (G-I) shows that TAE226 treatment (I) reduces the ultrastructural damage to the GBM normally present by 7 weeks of age in this model (H). Amelioration of GBM dysmorphology is generally observed (J). Treatment of primary cultured mesangial cells with TAE226 significantly reduces their migratory potential relative to untreated cells (I). K) Dose response for FAK inhibition by TAE226 in cultured mesangial cells. L) Northern blot for pFAk and βactin. F, scale bar=15 µm; J, scale bar=2 µm.

As shown in Example 1, progressive mesangial invasion of the glomerular capillary loops has been shown in Alport mice (see also Zallocchi et al., 2013, *Am J Pathol;* 183: 1269-80). FIG. 24 (A-F) shows dual immunofluorescence staining for the GBM marker laminin α5 and the mesangial cell surface marker integrin α8. Mesangial processes in the capillary loops are clearly observed in the vehicle treated Alport glomeruli (FIG. 24 (C), arrowheads, inset panel). TAE226 treatment resulted in amelioration of mesangial process invasion (FIG. 24 (E-F), inset panels; showing integrin α8 immunostaining only at the mesangial angles), suggesting that FAK activation on mesangial cells may contribute to this process mechanistically. Consistent with this notion, treatment of mesangial cells with TAE226 significantly reduced their cell migratory potential (FIG. 24 (K)) and blocked pFAK activation in a dose-dependent manner (FIG. 24 (L)). Transmission electron microscopic analysis of the GBM in TAE226-treated animals showed markedly improved GBM architecture relative to mice given vehicle (FIG. 24 (G-J)).

Figure 25:
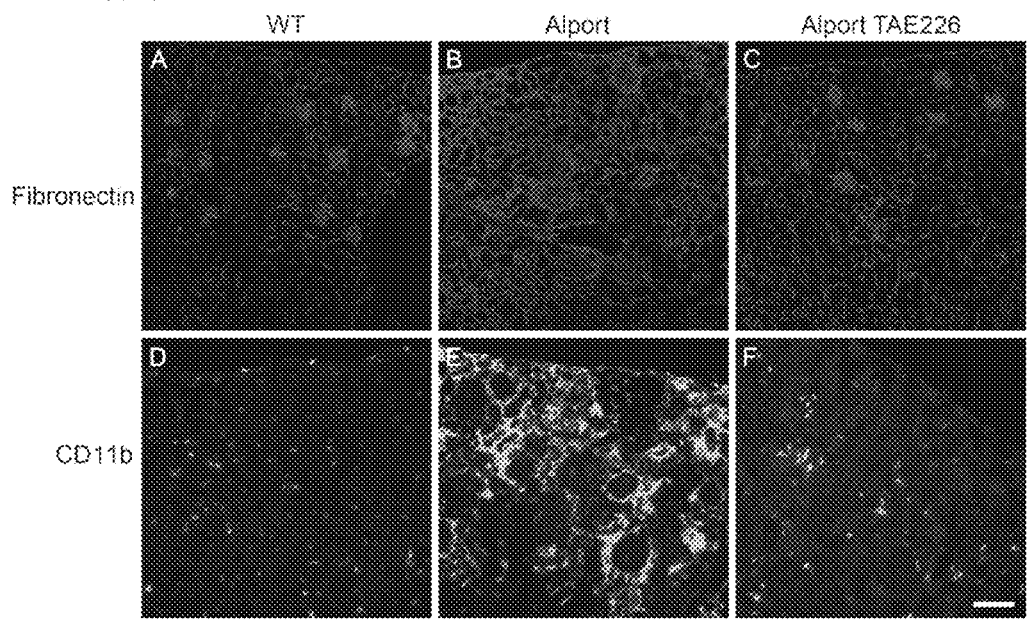
FIG. 25. Treatment of Alport mice with TAE226 ameliorates interstitial fibrosis and monocyte infiltration. Kidney cryosections from wild type and Alport mice that were either treated with vehicle or TAE226 were immunostained with antibodies specific for fibronectin (A-C) or the monocyte marker, CD11b (D-F). The accumulation of fibronectin in the interstitium, indicative of fibrosis, while abundant in Alport mice (B) is not apparent in Alport mice treated with TAE226 (C), which appear similar to wild type mice (A). Similarly, monocyte infiltration, as indicated by CD11b immunopositive cells, is readily apparent in Alport mice (E). In TAE226-treated Alport mice (F), however, the abundance of monocytes is similar to that in wild type mice (D), which are resident cells rather than infiltrating cells. Scale bar=50 µm.
Figure 26:
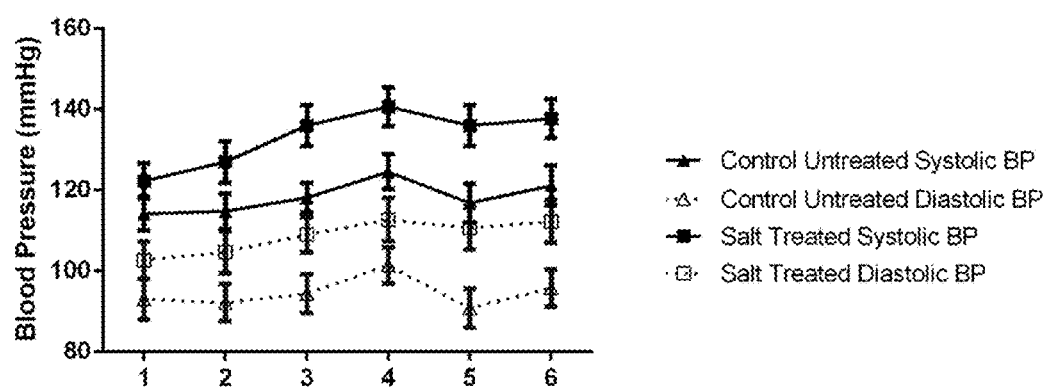
FIG. 26. Induction of hypertension and hypotension in Alport mice. C57Bl/6 X-linked Alport mice were made hypertensive by giving them the L-NAME salts in their drinking water from 4 to 7 weeks of age. Normotensive mice were given plain drinking water. Blood pressures were measured longitudinally using the CODA-2 tail cuff system.

To evaluate the effect of TAE226 treatment on renal fibrosis, kidney sections were stained with antibodies specific for either fibronectin (to assess renal scarring) or CD11b (to assess for monocytic infiltration). The results in FIG. 25 show that TAE226 treatment results in remarkably robust reduction in both renal scarring (A-C) and monocytic infiltration (D-F). In all four treated mice it was difficult to distinguish immunostaining of wild type kidneys from TAE226 treated Alport kidneys using these two antibodies.

Discussion

The initially punctate and then progressive deposition of laminin 211 and laminin 111 in the GBM of Alport mice is a phenomenon that would be expected to have some consequence contributing to the progressive deterioration of the glomerular structure/function, although until now no definitive functional consequence has been described. This example provides evidence that laminin 211 activates FAK on glomerular podocytes resulting in downstream activation of MMPs and pro-inflammatory cytokines that contribute to the progressive glomerular pathogenesis. At least some of these genes are induced by NF-kappaB activation, suggesting that the laminin 211/FAK/NF-kappaB circuit might be a central player driving the progression of Alport glomerular disease. In support of this notion, treatment of Alport mice with a small molecule inhibitor for FAK, TAE226, resulted in a significant reduction in glomerular expression of MMP-9, MMP-10, and MMP-12, improved glomerular function, ameliorated ultrastructural damage to the GBM, and blocked interstitial monocyte infiltration and interstitial fibrosis. In spite of what appears to be significantly improved ultrastructure, proteinuria in the TAE226 treated Alport mice, while lower than vehicle-treated mice, was still relatively high. This may be due to proteolytically induced microlesions in the GBM caused by troughs in the inhibitory activity of TAE226 (pharmacokinetics), or more likely due to pathways other than FAK that contribute to the glomerular pathogenesis.

While the effects of TAE226 on FAK activation in glomerular podocytes is likely the principal contributing factor underlying the observed improvement of the GBM ultrastructure and function, it is also likely that the systemic administration of this compound might have multiple influences on improved renal health in these animals. For example, as shown in Example 1, laminin 211 is deposited in the GBM by mesangial processes that invade the glomerular capillaries (see also Zallocchi et al., 2013, *Am J Pathol;* 183: 1269-80). This example shows that TAE226 treatment reduced the degree of mesangial process invasion (FIG. 24 (D-F)) and reduces the migratory potential of cultured mesangial cells (FIG. 24 (J)), suggesting that mesangial processes invasion of glomerular capillaries in Alport syndrome might be partially FAK-dependent. This makes some sense considering that deletion of integrin α1β1, a major mesangial cell surface integrin, also ameliorates mesangial process invasion of the glomerular capillaries in Alport mice, and significantly improves renal health in this model (Cosgrove et al., 2000, *Am J Pathol;* 157: 1649-1659; Zallocchi et al., 2013, *Am J Pathol;* 183: 1269-80). The remarkable reduction in interstitial monocytes might reflect a third distinct activity for FAK in Alport renal disease. In earlier work we showed that interstitial monocytes in a mouse model are primarily α1β1 integrin-positive (Sampson et al., 2001, *J Biol Chem;* 276: 34182-34188). It was later shown that α1β1 integrin-positive monocytes are selectively trafficked to the interstitium n Alport kidneys (Dennis et al., 2010, *Am J Pathol;* 177: 2527-2540). In other systems it has been shown that leukocyte activation following tight binding to the vascular endothelium can be mediated through FAK signaling (Li et al., 1998, *J Biol Chem;* 273: 9361-9364). Thus inhibiting monocyte activation to reduce interstitial monocyte efflux might represent a third target of FAK inhibitors that improves renal health in Alport mice.

Figure 17:
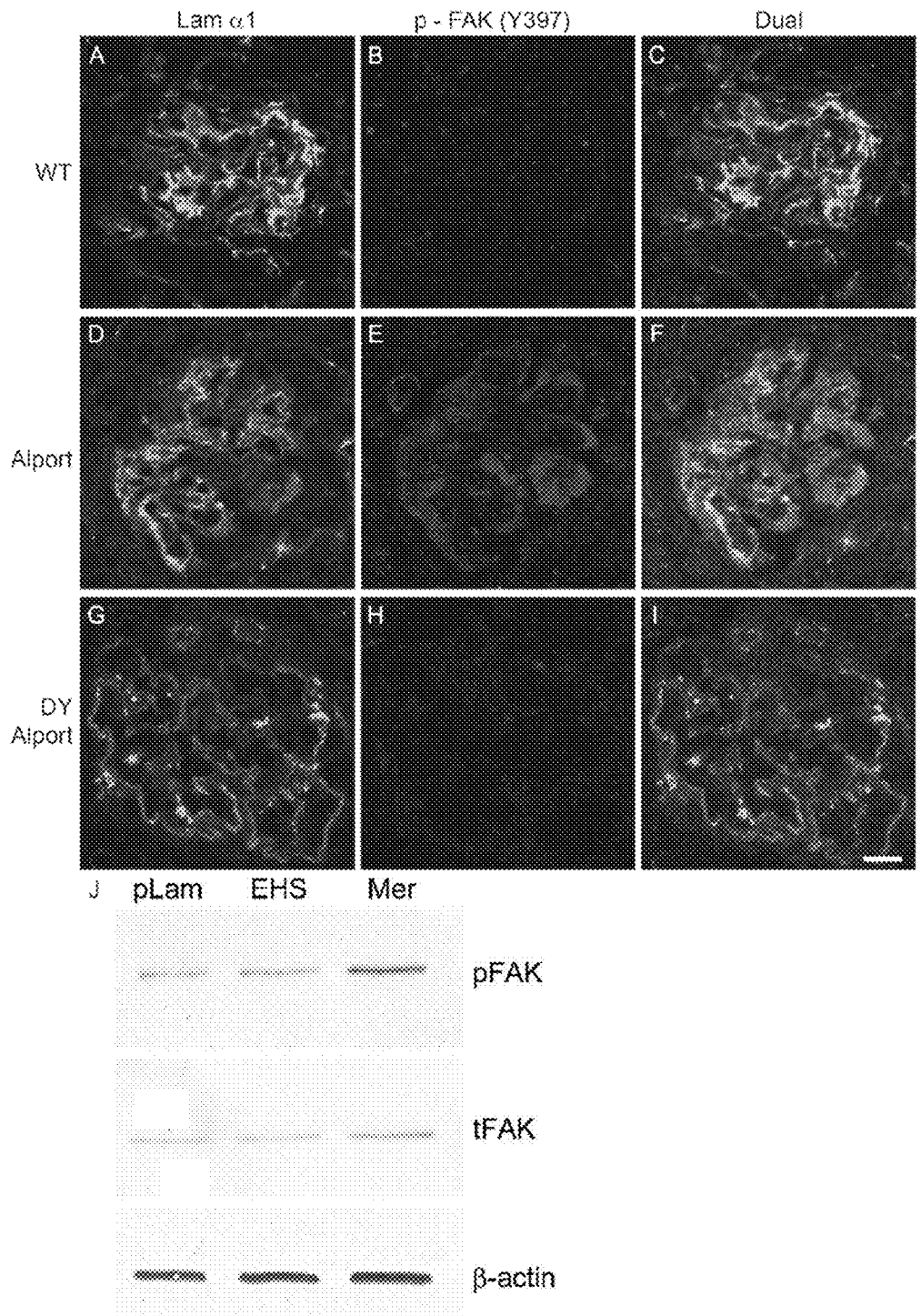
FIG. 17. Laminin 211, but not laminin 111 activates FAK on podocytes in vivo and in vitro. 7 week old wild type glomerulus stained with antibodies specific for laminin 111 and pFAK$^{397}$ show absence of pFAK immunostaining (A-C). 7 week Alport glomerulus stained with antibodies specific for laminin 111 and pFAK$^{397}$ pFAK immunostaining in podocytes adjacent to laminin 111-immunopositive GBM (D-F). G-I show the same immunostaining as for D-F using Alport mice that do not express laminin 211 (the dy/dy muscular dystrophy mutation). Note the absence of pFAK$^{397}$ immunostaining even though GBM is immunopositive for laminin 111. J) Wild type podocytes cultured on merosin (laminin 211) show activated pFAK$^{397}$ relative to cells cultured on placental laminin (laminin 521), or EHS laminin (laminin 111). Wild type podocytes were differentiated for 2 weeks and then plated on placental laminin, EHS laminin, or merosin for 15 hours, extracts were prepared and analyzed by western blot for expression of pFAK$^{397}$ and total FAK. β-actin was used as a loading control). Scale bar=10 µm.

This example demonstrates using both in vitro (FIG. 17 (G)) and in vivo (FIG. 17 (A-F)) approaches that laminin 211, but not laminin 111, activates FAK on glomerular podocytes. This is an important distinction when one considers that abnormal laminins have been shown to accumulate in the GBM in patients with membranous glomerulonephritis (Horikoshi et al., 1999, *Nephron;* 81: 284-288; and Fischer et al., 2000, *Nephrol Dial Transplant;* 15: 1959-1994) where much like the Alport model, the laminins are first observed in the irregularly thickened regions of the GBM. In the Alport mouse model, irregularly thickened abnormal laminin-rich regions of the GBM were shown to be more permeable to injected ferritin, suggesting that these regions are comprised of loosely assembled matrix that might contribute to progressive leakiness and proteinuria (Abrahamson et al., 2007, *J Am Soc Nephrol* 18: 2465-2472.). Based on our observation of FAK mediated induction of MMP-9, MMP-10, and MMP-12 in the Alport podocyte, it appears that the increased GBM permeability in these thickened regions might reflect partially degraded GBM. Earlier studies found that deletion of MMP-9 in Alport mice did not influence renal disease progression, suggesting that MMP-9 may not contribute significantly to the pathology (Andrews et al., 2000, *Am J Pathol;* 157: 303-311).

The accumulation of abnormal laminins in the GBM may be more generally applicable to glomerulonephritis. It will be important to determine specifically which abnormal laminin heterotrimers accumulate in the GBM in membranous glomerulonephritis where GBM deposition of laminin β1 has been described, whether FAK is activated, and whether elevated glomerular expression of MMPs is observed. Such data would implicate the use of FAK blockade as a potential therapeutic approach for this glomerular disease as well as for Alport syndrome. A recent study using both lipopolysaccharide (LPS) and anti-GBM antibody-induced glomerular disease models showed that podocyte injury could be limited by blocking FAK activation (Ma et al., 2010, *J Am Soc Nephrol;* 21: 1145-1156), providing further evidence of the general utility of FAK inhibitors for the treatment of glomerular diseases.

Laminin 211-mediated FAK activation is also observed in the CD151 knockout mouse model (FIG. 18). Like the Alport mouse, the CD151 knockout mouse shows massive up-regulation of both MMP-10 and MMP-12 (FIG. 19), providing further evidence that induction of these genes is regulated by FAK activation. MMP-10 expression in the glomerulus has not been previously documented, likely owing to its low abundance in healthy glomeruli. Immunostaining for MMP-10 (FIG. 19 (B)) showed that MMP-10 is undetectable in the wild type glomeruli and abundant in the Alport glomeruli. MMP-10, like its related stromelysin MMP-3, has a broad substrate specificity, which includes type IV collagen (Sanchez-Lopez et al., 1993, *J Biol Chem;* 268: 7238-7247; and Nagase H., 2001, Substrate Specificity of MMPs. Cancer Drug Discovery and Development: Matrix Metalloproteinase Inhibitors in Cancer Therapy, edited by Clendeninn J J and Krzysztof A. Totowa, N.J., Humana Press Inc., 39-66). The high levels of induction observed (700- to 1200-fold) suggest that MMP-10 might play an important role in the pathogenic mechanism of Alport glomerular disease, warranting further study.

As shown in Example 1, biomechanical strain, most likely owing to the change in basement membrane composition, has pro-pathogenic consequences in Alport glomeruli. These include exacerbating GBM destruction by way of MMP induction and accelerating the invasion of glomerular capillaries by mesangial processes (see also Zallocchi et al., 2013, *Am J Pathol;* 183: 1269-80; Meehan et al., 2009, *Kidney Int;* 76: 968-976). This example shows that biomechanical stretching of podocytes directly activates FAK and induces the expression of MMP-10 and MMP-12 (FIG. 21). Treatment of stretched cells with the FAK inhibitor TAE226 blocked MMP induction in this same set of experiments. This example also showed that stretching podocytes caused nuclear localization of NF-kappaB (FIG. 22), consistent with its activation (Beg et al., 1992, *Genes Dev;* 6: 1899-1913), and that adding a peptide inhibitor for NF-kappaB to stretched cells blocked the induction of MMP-10. Collectively, these data suggest that biomechanical strain exacerbates laminin 211-mediated activation of FAK in podocytes leading to NF-kappaB-dependent induction of MMP-10.

This example defines a role for GBM laminin 211 in Alport glomerular pathogenesis by way of activation of FAK on glomerular podocytes leading to the downstream activation of MMP-9, MMP-10, and MMP-12 gene expression. This mechanism of MMP induction involves NF-kappaB activation and is exacerbated by biomechanical strain on the glomerular capillary tuft. Further, this example shows that systemic inhibition of FAK by way of a small molecule inhibitor ameliorates both glomerular and tubulointerstitial pathologies, likely owing to its effects not only on glomerular podocytes, but also mesangial cells, and possibly firm adhesion-mediated monocyte activation. Since laminin 211 starts to be deposited in the Alport GBM as early as 10 days in the 129 Sv/J autosomal mouse model, where proteinuria is not detected until 3 weeks of age, we propose that this represents one of the earliest events underlying the development of Alport glomerular disease. This mechanism may be generally applicable to other forms of glomerulonephritis where the accumulation of "abnormal" laminins in the GBM has been documented.

This example has now published as "Laminin α2-mediated focal adhesion kinase activation triggers Alport glomerular pathogenesis," Delimont D, Dufek B M, Meehan D T, Zallocchi M, Gratton M A, Phillips G, Cosgrove D, *PLoS One*, 2014 Jun. 10; 9(6):e99083, doi: 10.1371/journal.pone.0099083, eCollection 2014, which is hereby incorporated by reference in its entirety.

Example 5

Endothelin A Receptor Blockade Prevents Mesangial Filopodial Invasion of Glomerular Capillaries and Delays Alport Glomerular and Interstitial Disease Onset The type IV collagen network in Alport glomerular basement membrane (GBM) is comprised of only α1(IV) and α2(IV) chains which contain fewer interchain crosslinks than the α3(IV)/α4(IV)/α5(IV) networks found in normal GBM. The presumed resulting increase in elasticity of the Alport GBM imparts biomechanical stresses on the cell contacts comprising the capillary tuft, which activates the Rho GTPases Rac1 and CDC42 in mesangial cells, inducing the invasion of the capillary tufts by mesangial filopodia. The filopodia deposit mesangial proteins in the GBM, which activate aberrant proinflammatory cell signaling in podocytes. Thus, CDC42 activation is the molecular trigger for Alport glomerular disease initiation.

With this example, 129 autosomal Alport mice were given either Bosentan (an endothelin A and B receptor antagonist) or Sitaxentan (an endothelin A receptor antagonist) from 2 to 7 weeks of age. Mice were analyzed longitudinally for proteinuria and BUN, glomerular RNA for gene expression of MMPs and pro-inflammatory cytokines by real time RT-PCR, and tissue was analyzed histochemistry and immunohistochemistry for pathologic changes.

Hypertension elevated expression of endothelin-1 in Alport endothelial cells, but not wild type endothelial cells. Endothelin blockade in Alport mice significantly reduced the mesangial filopodial invasion of glomerular capillaries. This was associated with delayed onset and slowed progression of proteinuria, and increase in lifespan. GBM dysmorphology was ameliorated, and glomerulosclerosis and interstitial fibrosis were not evident in treated Alport mice when age-matched vehicle-treated Alport mice showed >30% glomerulosclerosis and fibrosis scores between III and IV. Both Bosentan and Sitaxentan were equally effective at ameliorating Alport renal disease, likely because mesangial cells were found to express only the endothelin A receptor.

In conclusion, biomechanical strain-mediated activation of endothelin expression in Alport endothelial cells results in endothelin A receptor-mediated activation of CDC42 in mesangial cells, inducing the invasion of the subendothelial aspect of the GBM by mesangial filopodia and is an important factor contributing to the mechanism of Alport disease initiation, and presents a host of novel therapeutic targets with the potential to delay/inhibit the onset of Alport glomerular and tubulointerstitial pathogenesis.

Example 6

Early Mechanisms of Alport Glomerular Pathology

The cellular origin of glomerular basement membrane (GBM) laminin 211 has not been previously determined. As shown in Example 1, the source of GBM laminin 211 in Alport GBM is mesangial cell processes, which are invading the capillary tufts. Salt-mediated hypertension exacerbates this mesangial process invasion. Deposition of laminin 211 in the GBM activates focal adhesion kinase in podocytes, which leads to NF-kappaB activation and induction of pro-inflammatory cytokines as well as MMPs, driving the progression of Alport glomerular disease. A knockout mouse for the integrin α3β1 co-receptor CD151, which results in reduced adhesion of podocytes pedicles to GBM laminin 521, also develops mesangial process invasion of the capillary loops with GBM deposition of laminin 211, demonstrating the same phenotype for a completely unrelated molecular component of the glomerular capillary structural barrier. See also, Zallocchi et al., 2013, *Am J Pathol;* 183(4):1269-80.

The CD151 knockout mouse model also shows accelerated glomerular disease progression in response to hypertension ((Sachs et al., 2012, *J Clin Invest;* 122(1):348-58). As shown in the previous examples, biomechanical stretching of cultured mesangial cells induces pro-migratory cytokines TGF-β1 and CTGF, both known to be induced in Alport glomeruli (Sayers et al., 1999, *Kidney Int;* 56(5):1662-1673; and Koepke et al., 2007, *Nephrol Dial Transplant;* 22(4):1062-9). Using inhibitor studies in Example 1, it has been shown that mesangial cell migration is mediated by the Rho GTPase RAC1 and that treatment of Alport mice with a RAC1 inhibitor blocks mesangial process invasion of the glomerular capillary tufts, clearly implicating the activation of Rac1 in this process (see also Zallocchi et al., 2013, *Am J Pathol;* 183(4):1269-80). These data define a surprising role for biomechanical strain mediated-induction of mesangial cell process invasion as a key aspect of Alport glomerular disease initiation, and set the stage for defining novel therapeutic targets aimed at blocking this process.

Figure 30:
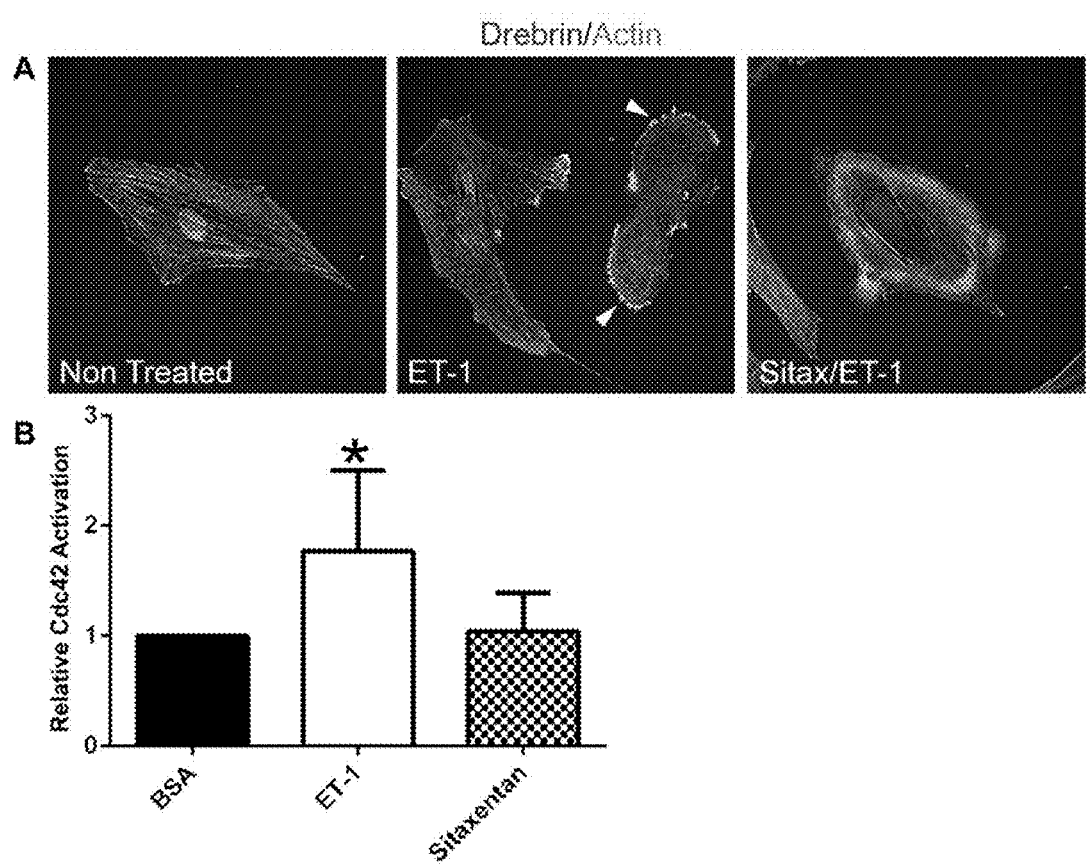
FIG. 30. Treatment of mesangial cells with endothelin-1 activates CDC42 and induces the formation of drebrin-positive actin microspikes; microspikes and CDC42 activation are inhibited by pre-treatment of cells with Sitaxentan. A) Cultured mesangial cells were serum starved, pretreated for 1 hour with or without Sitaxentan, treated for 30 minutes with endothelin-1, fixed with acetone, and dual stained with anti-drebrin antibodies (red) and phalloidin (green). Drebrin-positive microspikes (filopodia, denoted by arrowheads) are highly abundant on the endothelin-treated cells, but not detected when the cells are pre-treated with Sitaxentan. B) Cells were treated as in A, then lysates prepared and assayed by ELISA for GTP-CDC42. Endothelin treatment significantly activates CDC42 in the cultured mesangial cells, and its activation is inhibited by pre-treatment of cell with Sitaxentan.

Below, it is also shows that endothelin 1 is induced in the endothelial cells of Alport mice at an early age (before the onset of proteinuria), and that expression is further induced by hypertension. It has been previously shown that endothelin 1 activates CDC42/RAC1 in glomerular mesangial cells via activation of endothelin receptors (Chandi et al., 2005, *J Biol Chem;* 280(1):578-84; Chandi and Sorokin, 2006, *Exp Biol Med;* 231(6): 761-5), and it is well established that biomechanical stretching induces endothelin 1 expression and secretion by endothelial cells (Just et al., 2004; Babu et al., 2012). It is also shown that ET-1 treatment of primary cultured mesangial cells activates CDC42 and induces the formation of drebrin-positive actin microspikes (FIG. 30). Thus, it is likely that activation of RAC1/CDC42-mediated actin cytoskeletal dynamics associated with mesangial process invasion of the glomerular capillary tufts in Alport syndrome is caused by endothelin-1 expression/secretion induced in the glomerular endothelial cells by biomechanical strain.

While the presence of abnormal laminins in the Alport GBM was described 14 years ago (Cosgrove et al., 2000, *Am J Pathol;* 157(5):1649-59; Kashtan et al., 2001, *J Am Soc Nephrol;* 12:252-60), the functional significance of this observation as it relates to molecular pathology in the glomerulus has, until now, remained unknown. As shown in Example 4, FAK activation in podocyte foot processes is identified specifically in regions of the GBM where abnormal laminin deposition is occurring (see also Delimont et al., PLoS One, 2014 Jun. 10; 9(6)). This is observed as early as P10, long before detectable proteinuria for Alport mice on the 129 Sv background (about 3 weeks). We have determined the cellular source of GBM laminin 211 to be mesangial filopodia. If the formation of filopodia is blocked by way of a small molecule inhibitor for RAC1/CDC42 Rho GTPases, laminin 211 deposition is largely blocked in the Alport GBM (see Example 1 and Zallocchi et al., 2013, *Am*

*J Pathol.* 2013 October; 183(4):1269-80). As shown below, hypertension results in markedly elevated endothelin-1 expression in the glomerular endothelial cell compartment in pre-proteinuric Alport mice, but not in wild type mice. When endothelin receptors in Alport mice are blocked with small molecule inhibitors for both endothelin A and B receptors (Bosentan) or one specific for endothelin A receptors (Sitaxentan), mesangial process invasion of the glomerular capillaries was markedly reduced, delaying the onset and progression of proteinuria, ameliorating GBM structural abnormalities, and significantly reducing glomerular expression of MMPs and pro-inflammatory cytokines. Collectively, these studies define a paradigm shift in our understanding of glomerular pathology in Alport syndrome, and define a key mechanism of glomerular disease initiation where biomechanical strain mediated induction of endothelin-1 in glomerular endothelial cells activates RAC1/CDC42 GTPases in mesangial cells. RAC1/CDC42 activates actin cytoskeletal dynamics in mesangial cells, resulting in the invasion of glomerular capillaries by mesangial filopodia. The filopodia deposit laminin 211 in the GBM, which activates FAK in podocytes resulting in elevated expression of pathologic genes, and revealing a key molecular mechanism underlying podocyte dysfunction in Alport syndrome. The discovery of this pathway reveals novel opportunities for therapeutic intervention that were previously inconceivable, including endothelin blockade using drugs already FDA approved for the treatment of pulmonary hypertension. This example will rigorously test this pathway by way of in vivo genetic modeling and in vitro cell culture studies, aiming to define new endothelial cell-specific therapeutic targets that can dislocate the strain-dependent induction of endothelin-1.

The presence of abnormal laminins in the GBM, likely due to reduced ILK activity, results in activation of FAK, which is a critical step in disease initiation. The GBM laminin 211 is deposited by mesangial filopodial processes that invade the GBM as a result of biomechanical strain-mediated RAC1/CDC42 activation. This is a new direction from conventional thinking regarding the pathobiology of Alport glomerular disease. This is shown in Example 1 (see also Zallocchi et al., 2013, *Am J Pathol;* 183(4):1269-80), and the extension of this work forms the foundation of this example. The fact that endothelin A blockade blocks this process, and has such a profound effect on Alport glomerular pathology predicts that this mechanism is centrally important and provides an opportunity for developing effective therapeutic approaches that target this pathway.

FAK activation is directly linked to the induction of actin cytoskeletal rearrangement (and thus contributing to foot process effacement) and results in maladaptive gene regulation including massive up-regulation of MMP-10 and MMP-12 in podocytes. This turned out to be entirely true. FIGS. 26-31 are provided to show the evidence for this mechanism. It turns out that laminin 211, but not laminin 111, does activate FAK, and that FAK inhibition using small molecule inhibitors ameliorate MMP-10 and MMP-12 induction, GBM ultrastructural abnormalities, and renal fibrosis in Alport mice. This work is shown in Example 4 (see also Delimont et al., *PLoS One.* 2014 Jun. 10; 9(6): e99083).

Massive induction of MMP-10 and MMP-12 in glomerular podocytes causes proteolysis of the GBM resulting in proteinuria and progression towards glomerulosclerosis, playing a major role in the onset and the rate of progressive GBM pathogenesis in Alport syndrome. Surprisingly, these two MMPs, which are massively induced in Alport glomerular RNA, do indeed influence progression of glomerular pathology, the effect of deleting them was rather mild. Thus it is likely there are other proteases that play a dominant role in the irregular thickening of the GBM and in the evolution of proteinuria. The small molecules used in previous studies have broad inhibitory effects ((Rao et al., 2006, *Am J Pathol;* 169: 32-46; Zeisberg, et al., 2006, *PLoS Med;* 3: e100), and predict that these proteases are indeed important to glomerular pathology. The specific proteases that dominate this influence remain to be discovered. Nonetheless, work on MMP-10 and MMP-12 is important, because it rules out a dominant role for these metalloproteinases in Alport GBM destruction. The experiments of this example are upstream of proteolytic degradation of the GBM, given that endothelin A receptor blockade largely prevents irregular GBM dysmorphology.

Research Design and Methods

It has been previously shown that hypertension accelerated the progression of Alport glomerular disease, suggesting a key role for biomechanical strain in the disease mechanism (Meehan et al., 2009, *Kidney Int;* 76: 968-976). This the data demonstrating the induction of mesangial process invasion of the glomerular capillaries suggests that biomechanical stretching of the capillary tuft might activate actin cytoskeletal dynamics in Alport glomeruli. As shown in Example 1, this observation was extended with the discovery that mesangial processes invade the glomerular capillaries in a biomechanical strain-mediated Rac1/CDC42-activation mechanism (see also Zallocchi et al., 2013, *Am J Pathol;* 183: 1269-80). Importantly, the mesangial filopodia in the GBM are depositing mesangial matrix proteins, including laminin 211, which activates focal adhesion kinase in glomerular podocytes, resulting in the activation of genes encoding pro-inflammatory cytokines and metalloproteinases, which drive the progression of GBM damage. This is shown in Example 4 (see also Delimont et al., 2014, *PLoS One;* 9(6):e99083). Thus, the mechanism underlying the activation of mesangial filopodia will reveal novel targets of therapeutic intervention aiming to arrest the initiation of these events.

To explore this potential mechanism, C57Bl/6 X-linked Alport mice were treated with L-NAME salts from 4 weeks to 7 weeks of age to establish conditions of hypertension to compare with normotensive mice. At 7 weeks this model is still pre-proteinuric. Blood pressure was monitored thrice weekly using the CODA2 tail cuff system ((Meehan et al., 2009, *Kidney Int;* 76:968-976). The readings shown in FIG. 26 demonstrate that these treatments resulted in blood pressure that varied by 15 to 25 mm of mercury for both systolic and diastolic measurements.

Figure 27:
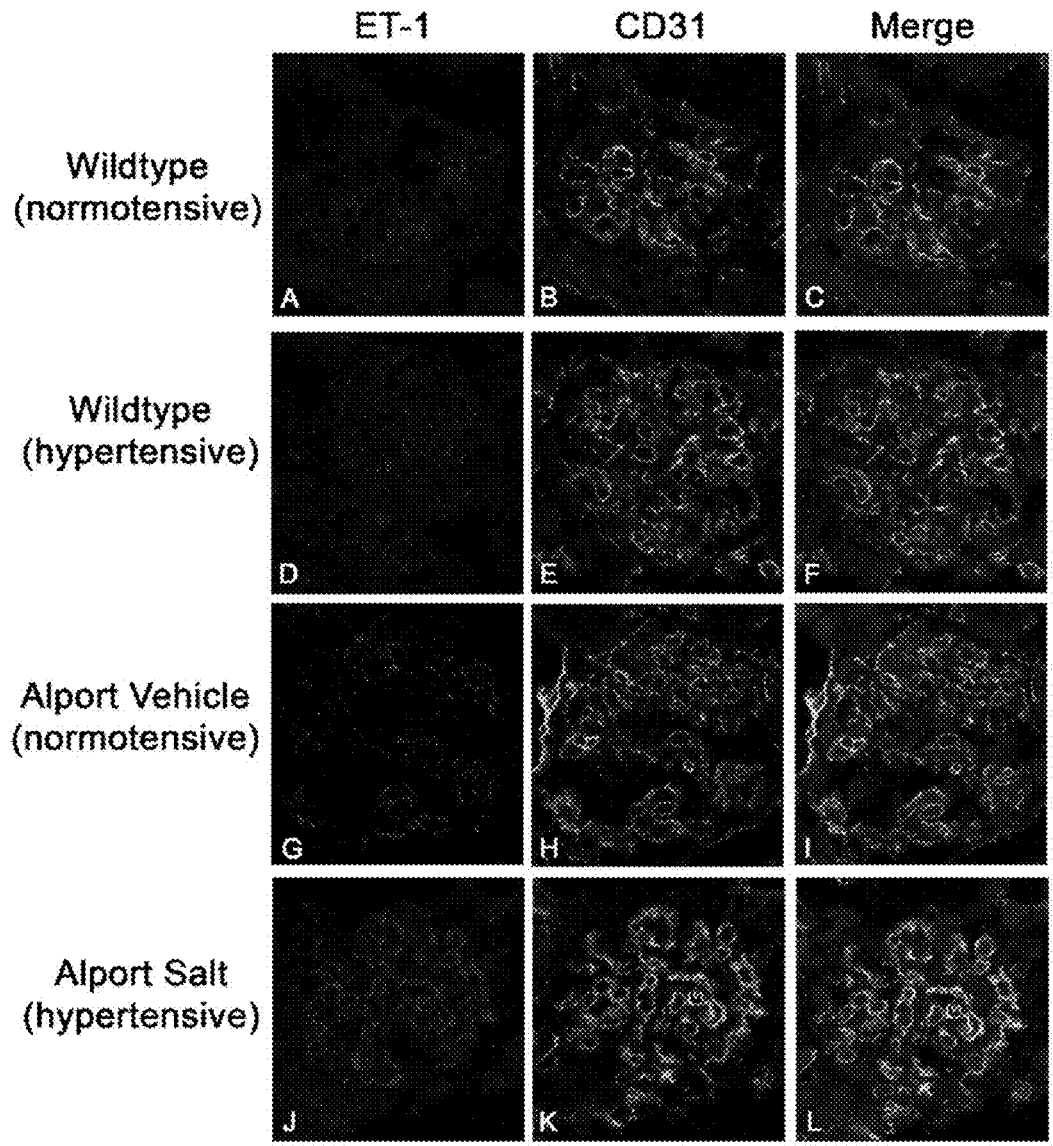
FIG. 27. Hypertension induces endothelin-1 in Alport glomerular endothelial cells. Cryosections were dual immunostained with antibodies specific for either endothelin-1 (ET-1) (A, D, G, and J) or CD31 (a marker for endothelial cells) (B, E, H, and K). Panels C, F, I, and L are a merging of results from staining with endothelin-1 and CD31. Elevated expression of endothelin-1 is clearly evident in glomeruli from hypertensive mice relative to normotensive mice (compare G and J). This was not observed in wild type mice (compare A and D). Co-localization of endothelin-1 with CD31 demonstrates this induction is coming from the endothelial cell compartment.
Figure 28:
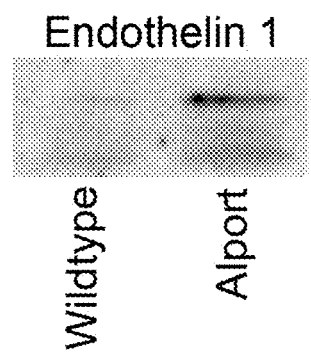
FIG. 28. ET-1 protein expression is elevated in glomeruli from Alport mice relative to age/strain-matched wild type mice. Glomeruli were isolated from 7 week old 129 Sv autosomal Alport mice and wild type mice. Lysates were analyzed by western blots and probed with anti-ET-1 antibodies.

It has been demonstrated that endothelin A receptor activation on mesangial cells leads to RAC1/CDC42 activation (Chandi et al., 2005, *J Biol Chem;* 280(1):578-84; and Chandi and Sorokin, 2006, *Exp Biol Med (Maywood);* 231(6):761-5). Endothelin-1 expression was examined in cryosections from 7 week old normotensive and hypertensive mice by immunofluorescence. FIG. 27 shows that under normotensive conditions, endothelin-1 immunolabeling in Alport glomeruli is weak, but more intense than in glomeruli from wild type mice (compare panels A-C with panels G-I). Under hypertensive conditions, immunostaining intensity in Alport glomeruli is much greater (FIG. 27 (J-L)). Co-localization with CD31 (an endothelial cell marker) demonstrates that the endothelin immunostaining is coming from the endothelial cell compartment. Similar differences in blood pressure in age/strain matched wild type mice did not affect endothelin-1 immunostaining intensity, which was of very low abundance (FIG. 27 (A-F)). Thus it is apparent that strain mediated induction of endothelin-1 might be responsible for inducing the formation of mesangial filopodia by way of endothelin receptor activation. FIG. 28 shows western blot analysis of glomerular lysates from wild type and Alport mice, confirming that Alport mice express higher levels of endothelin-1.

Figure 29:
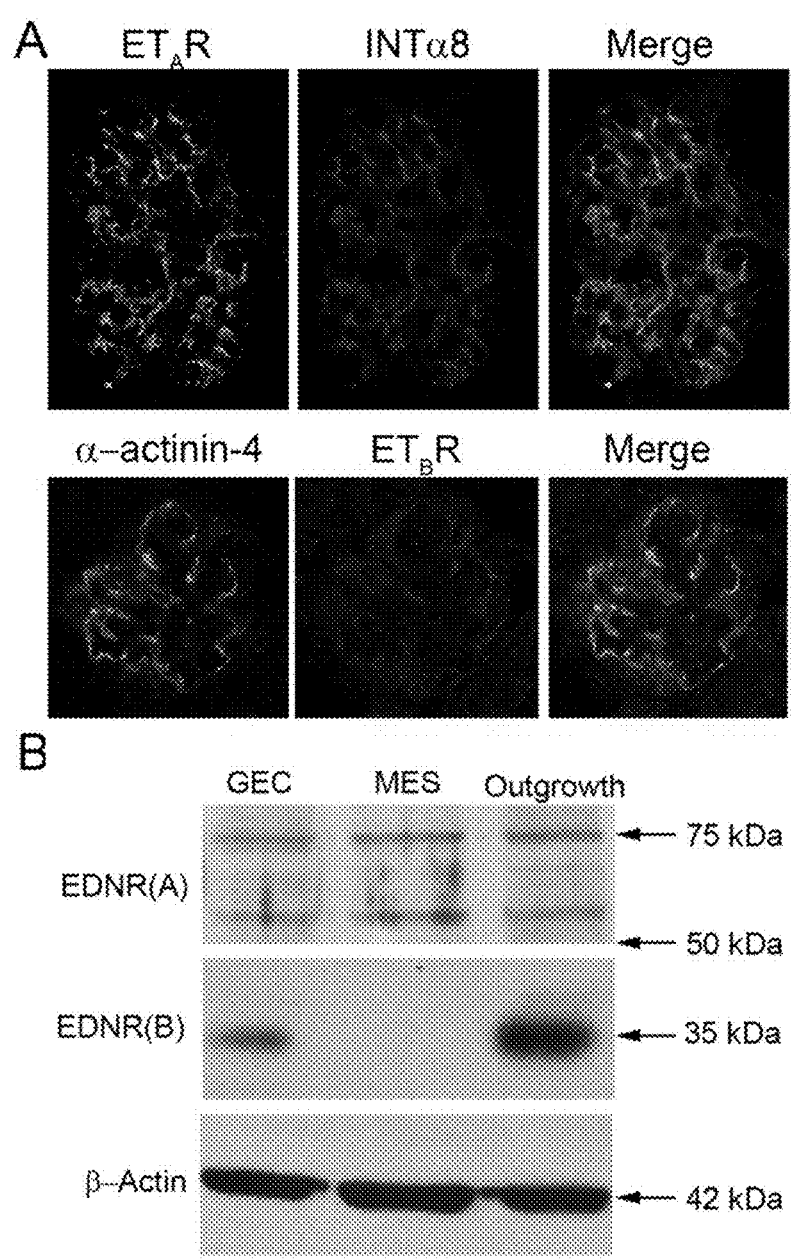
FIG. 29. Endothelin A receptor is the primary endothelin receptor on mouse mesangial cells. A) Kidney cryosections from wild type mice were dual stained with antibodies specific for the endothelin A receptor and the mesangial cell marker integrin $\alpha 8$. Staining in a single glomerulus is shown. The merged image shows that the endothelin A receptor staining is primarily in the mesangial cell compartment. The lower panels show that Endothelin B receptors are principally expressed on podocytes, consistent with earlier reports (Wendel et al., 2006). Alpha-actinin-4 is used as a podocyte marker. B) Western blots from cultured mesangial cells and podocytes confirm that ETAR is robustly expressed on mesangial cells, while ETBR is not detected. Cultured podocytes and glomerular outgrowths (cultured for 24 hours after glomerular isolation) express both ETAR and ETBR.

There are two classes of endothelin receptor; the endothelin A receptor ($ET_AR$) and the endothelin B receptor ($ET_BR$). Previous studies suggest that the primary endothelin receptor on glomerular mesangial cells is the endothelin A receptor (Wendel et al., 2006, *J Histochem Cytochem;* 54(11): 1193-203). This same study showed that endothelin B receptors are primarily found on glomerular endothelial cells and podocytes. To determine which receptors are expressed on mouse mesangial cells, immunofluorescence and western blot analysis were performed on both glomeruli and cultured primary mesangial cells and cultured podocytes. FIG. 29 (A) shows that the $ET_AR$ co-localizes with the mesangial cell marker integrin α8, while the $ET_BR$ localizes primarily to glomerular podocytes, which are identified by the podocyte marker α-actinin-4. Western blots (FIG. 29 (B)) confirm that glomeruli express both $ET_AR$ and $ET_BR$, and cultured mesangial cells express only $ET_AR$. Cultured podocytes express both $ET_AR$ and $ET_BR$, however $ET_BR$ are expressed at higher levels.

While the link between endothelin treatment of cultured mesangial cells and the activation of Rac1/CDC42 Rho GTPases has been demonstrated, the connection between $ET_AR$ activation and filopodia formation in mesangial cells has not. To address this, serum-starved cultured mesangial cells were pre-treated (or not) with the $ET_AR$ antagonist, Sitaxentan, and then stimulated the cells with endothelin-1. Cells were then dual labeled with anti-drebrin antibodies (drebrin stabilizes actin filaments in filopodia) and phalloidin. The results in FIG. 30 (A) demonstrate that treatment of cultured mesangial cells with endothelin-1 induces the formation of drebrin-positive filopodial microspikes on cultured mesangial cells, and pretreatment of cells with the ETAR antagonist Sitaxentan blocks the formation of microspikes. Lysates from cultured mesangial cells were further analysed using these same conditions for the activation of CDC42 using a commercial ELISA assay for GTP-CDC42.

The results in FIG. 30 (B) show that endothelin-1 treatment significantly activates CDC42 in these cells, and that pretreatment with Sitaxentan prevents this activation. Combined these data provide the scientific platform for in vitro studies proposed in Aim 2.

To determine whether ETR antagonism prevents mesangial filopodia formation in vivo, we treated 129 Sv Alport mice with either Bosentan ($ET_AR$ and $ET_BR$ antagonist) or Sitaxentan (an $ET_AR$ antagonist) from 2 weeks to 7 weeks of age. The data from both inhibitors was essentially identical, which is consistent with the biological effect (CDC42 activation and mesangial filopodia formation) being due to $ET_AR$ signal transduction. In the interest of space, we are providing the evidence generated using the $ET_AR$ inhibitor, Sitaxentan. Both of these compounds have been used clinically to treat pulmonary hypertension.

Figure 31:
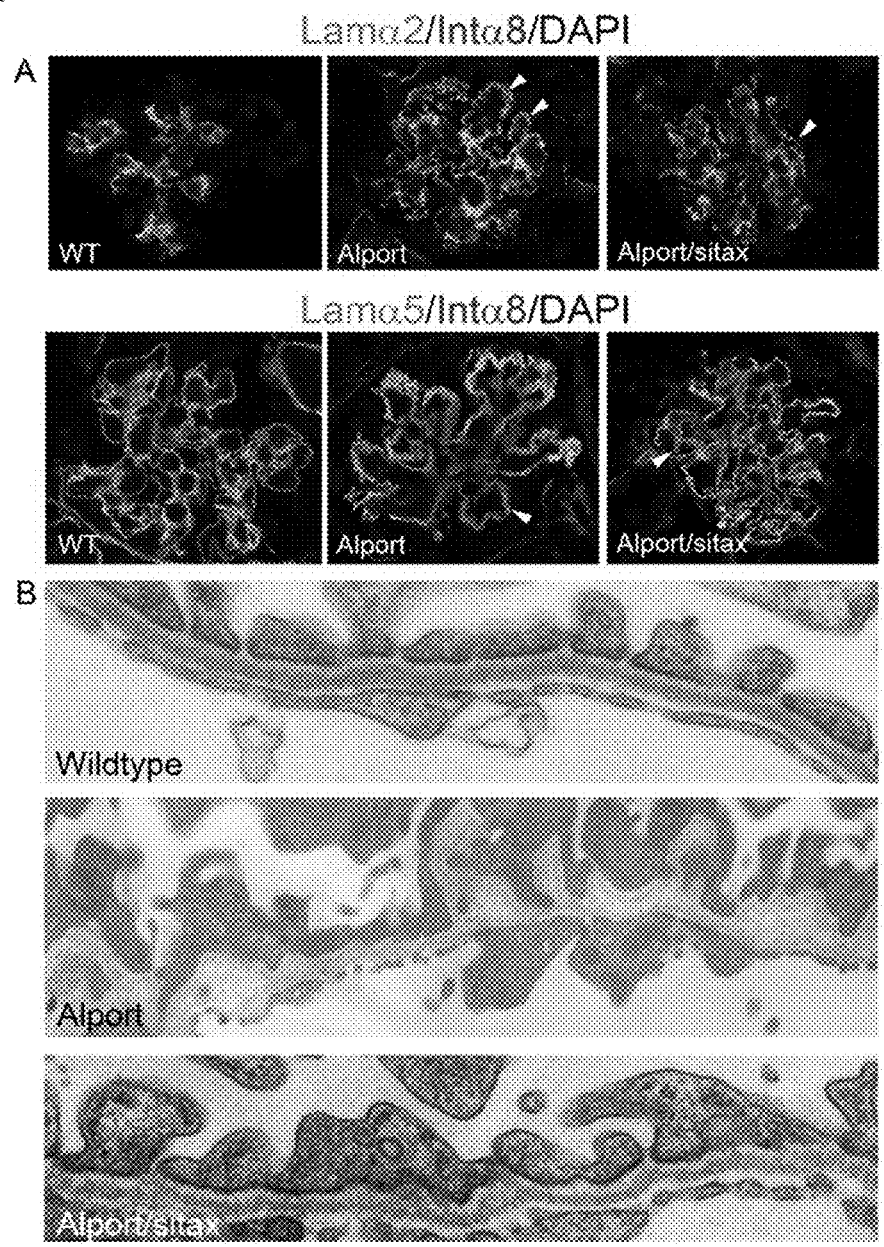
FIG. 31. Endothelin A receptor blockade prevents mesangial process invasion of glomerular capillaries and ameliorates GBM damage. 129 Alport animals were treated with the endothelin A receptor specific blocking agent Sitaxsentan from 2 weeks to 7 weeks of age. A) Dual staining demonstrates absence of integrin $\alpha 8$ immunostaining in the glomerular capillaries, which are dual stained with either anti-laminin $\alpha 2$ or anti-laminin $\alpha 5$ antibodies. Arrows denote integrin $\alpha 8$ immunopositivity in the capillary loops of the glomeruli from untreated Alport mice, and the relative absence of integrin $\alpha 8$ immunopositivity in the sitaxentan-treated mice. B) Sitaxsentan ameliorates GBM dysmorphology, largely normalizing the irregular thickening and thinning observed for the GBM of 7 week old Alport mice.
Figure 32:
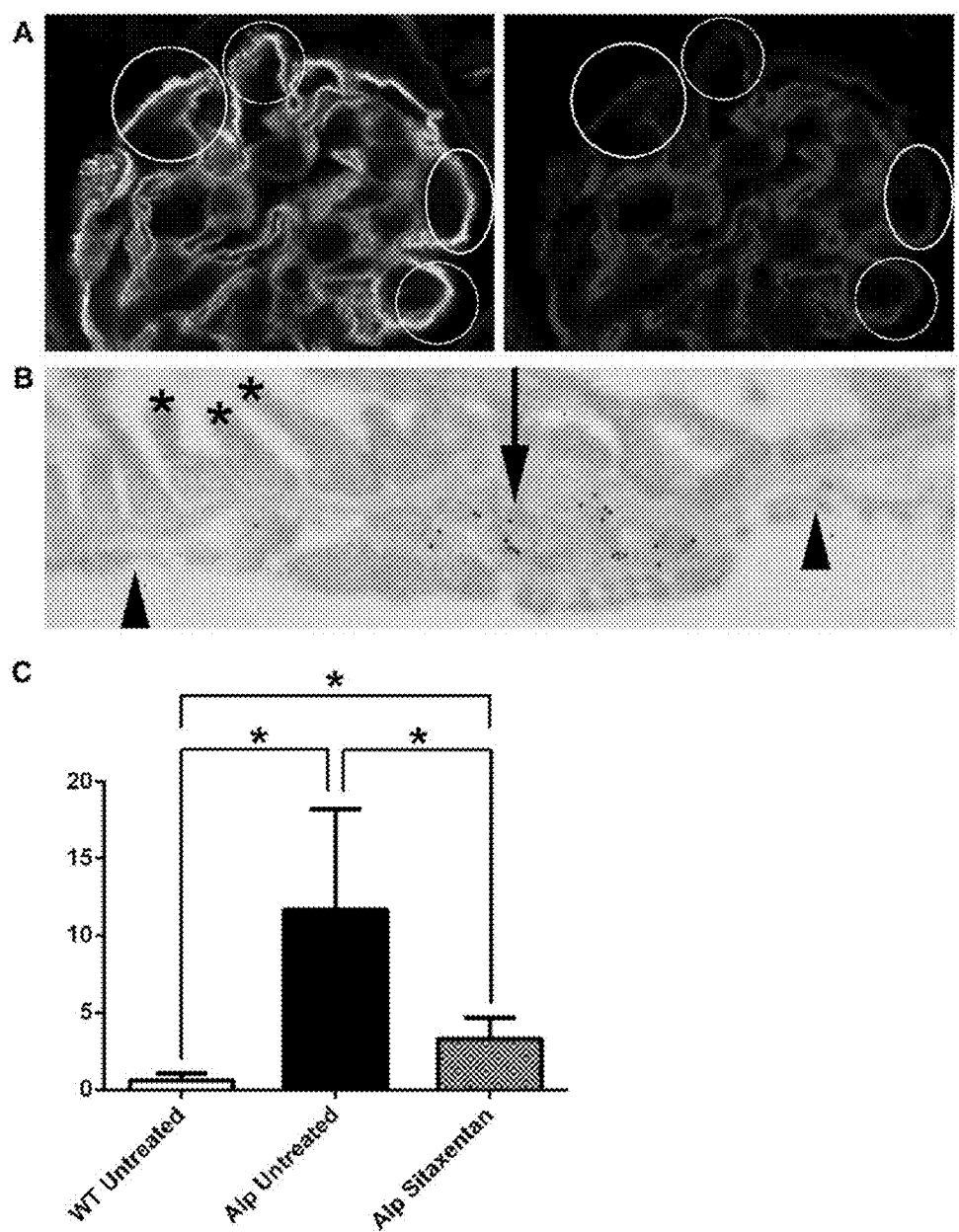
FIG. 32. Quantitative analysis of integrin $\alpha 8$ immunolabeling in the GBM demonstrates extensive filopodial invasion in 7 week Alport glomeruli that is prevented by treatment of animals with Sitaxentan. At least 6 glomeruli from at least 3 independent animals per group were analyzed by quantifying red fluorescence in circumferential capillary loops (defined by laminin $\alpha 5$ immunostaining in green) using NIH image J software. Mesangial angles were excluded. A) An example of how the capillaries were partitioned for these measures. B) Immunogold labeling for integrin $\alpha 8$ in a filopodial cross-section on the sub-endothelial aspect of an Alport capillary loop (arrow). Note the absence of immunogold labeling in the podocyte pedicles (asterisks) and the fenestrated endothelium (arrowheads). C) Quantitative results for red fluorescence in the capillary loops. The quantitative analysis clearly demonstrates extensive integrin $\alpha 8$ immunolabeling in the glomerular capillaries of Alport mice, which is significantly reduced (to near wild type control levels) in Alport mice treated with Sitaxentan.

129 Sv autosomal Alport mice were given Sitaxentan once daily by oral gavage from 2 weeks to 7 weeks of age. Kidney cryosections were immunostained using antibodies for laminin α2 and integrin α8 to determine the effect of drug treatment on laminin 211 deposition in the GBM or laminin α5 and integrin α8 to determine the degree of mesangial filopodial invasion in the glomerular capillaries. In addition, transmission electron microscopy was used to determine whether the $ET_AR$ antagonist ameliorates GBM damage. The results in FIG. 31 demonstrate that vehicle-treated Alport mice showed extensive invasion of glomerular capillaries by mesangial filopodia, which is typical for this model at 7 weeks of age. Sitaxentan-treated mice showed a near complete absence of mesangial filopodial invasion of glomerular capillaries, looking much more like the wild type glomeruli, especially with regard to the normalization of linear laminin α5 immunostaining, rather than the irregular laminin α5 immunostaining observed in glomeruli from vehicle-treated mice. A blow-up of a vehicle treated Alport glomerulus immunolabeled with laminin α5 and integrin α8 is provided in FIG. 32 (A) which demonstrates that the often punctate GBM integrin α8 immunolabeling is observed in all of the capillary loops, consistent with filopodial invasion. FIG. 32B shows quantitative analysis of total red fluorescence (integrin α8 immunostaining) in the capillary regions (laminin α5 immunopositive, but excluding the mesangial angles) from at least 6 independent glomeruli from at least three individual mice per group. The data shows a significant elevation in capillary red fluorescence in the glomeruli from vehicle-treated Alport mice compared wild type mice, and normalization of capillary integrin α8 immunostaining in the Sitaxentan treated mice. Transmission electron microscopic analysis of the GBM, which is shown at the bottom of FIG. 31, demonstrates that Sitaxentan treatment resulted in normalization of the GBM architecture.

Figure 33:
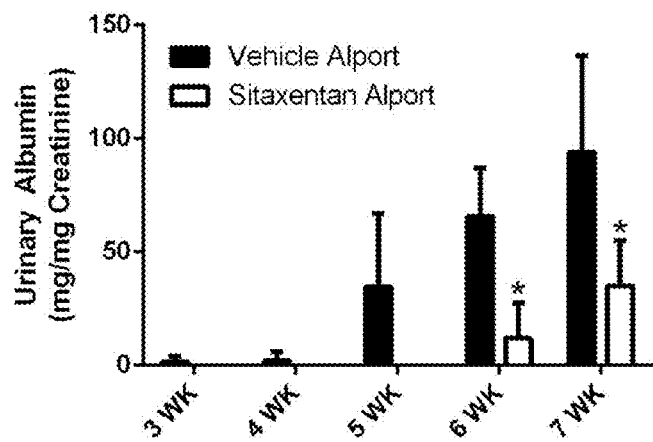
FIG. 33. Sitaxentan treatment of Alport mice significantly delays the onset and progression of proteinuria. Urine was collected at the indicated time points and analyzed for albumin using an ELISA kit. Albumin measures were normalized to urinary creatinine. Note that measurable albumin in the Sitaxentan-treated mice was not detected until 6 weeks of age indicating a delayed onset of glomerular disease.
Figure 34:
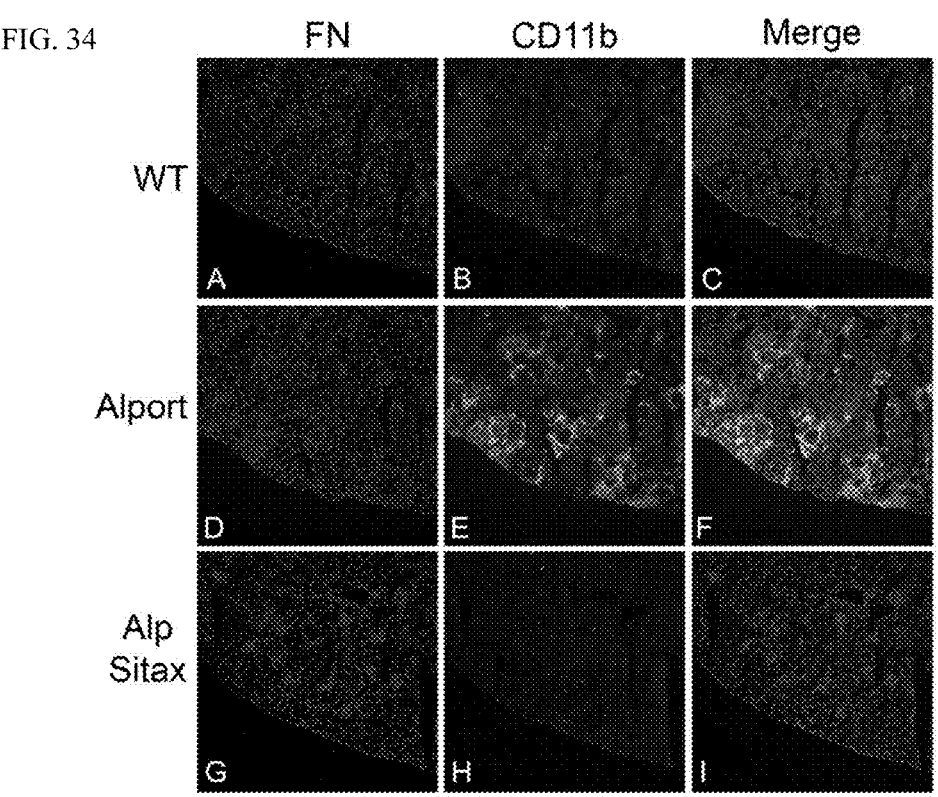
FIG. 34. Sitaxentan treatment ameliorates interstitial fibrosis and monocytic infiltration in Alport kidneys. Cryosections from Sitaxentan-treated and vehicle treated wild type and Alport mice were immunostained with antibodies specific for fibronectin (a marker for fibrosis) (A, D, and G) and CD11b (a marker for interstitial monocytes) (B, E, and H). Panels C, F, and I are a merging of results from staining with FN and CD11b. Note the complete absence of fibrosis and interstitial monocytes in the treated mice.
Figure 35:
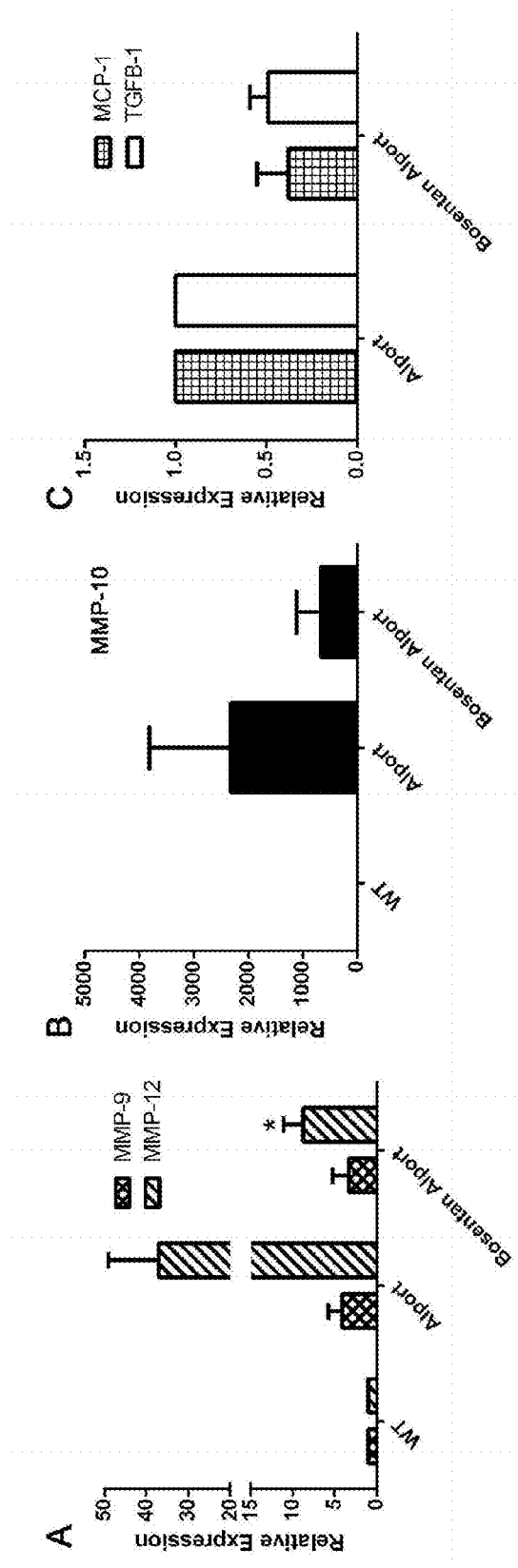
FIG. 35. Bosentan treatment reduces nRNA expression of MMP-9, MMP-10, MMP-12, MCP-1, and TGFβ1 in glomeruli from Alport mice. Glomerular RNA from Bosentan-treated and vehicle-treated mice was analysed by real time RT-PCR for MMP-9 and MMP-12 transcripts (A), MMP-10 transcripts (B), and MCP-1 and TGFβ1 transcripts (C). MMP (matrix metalloproteinase), MCP-1 (monocyte chemoattractant protein-1), TGFβ1 (transforming growth factor beta-1).

Sitaxentan treated mice showed delayed onset of proteinuria, as well as significantly reduced proteinuria after the onset (FIG. 33). Normally detected by 3 weeks of age, proteinuria was not detected until 6 weeks of age in the treated mice. This is consistent with the idea that endothelin receptor blockade works at the level of disease initiation. Sitaxentan treatment also profoundly ameliorated interstitial fibrosis and monocyte recruitment to the renal interstitium, as evidenced by fibronectin and CD11b immunostaining (FIG. 34). Very similar results were again observed when animals were treated with Bosentan. Glomerular expression of MMP-10, and -12 as well as the proinflammatory cytokines TGF-β1 and MCP-1 were significantly reduced in Bosentan-treated Alport mice relative to Alport mice given vehicle (FIG. 35). With the exception of TGF-β1, Sitaxentan gave quantitatively similar results. Collectively, these data indicate that endothelin A receptor blockade is a novel therapeutic option for the treatment of Alport syndrome, and works by blocking the activation of RAC1 and CDC42, preventing the activation of mesangial actin dynamics and thereby preventing the invasion of glomerular capillaries by mesangial filopodia. This represents a previously unrecognized etiology for the action of endothelin receptor blockade in the treatment of biomechanical strain-mediated Alport glomerular disease initiation.

The data presented above provide strong evidence that endothelin receptor activation results in mesangial process invasion of glomerular capillaries, indicating that additional drug targets aimed at blocking Alport glomerular disease initiation by uncoupling strain-mediated induction of endothelin-1.

Specific Aim 1

Cyclic cell stretching glomerular endothelial cells will result in elevated expression of endothelin-1 and other known stretch-responsive genes via the TRPC3/zyxin pathway. Previously published work shows that mechanical stretching of umbilical cord-derived human endothelial cells, and aorta derived murine endothelial cells results in elevated expression of endothelin-1 (Wojtowicz et al., 2010, Circ Res; 107(7): 898-902; Babu et al., 2012, Sci Signal; 5(254):ra91), a finding also observed in mechanically stretched astrocyte cultures (Ostrow et al., 2011, Biochem Biophys Res Commun; 410(1):81-6). Similar observations have not yet been documented for glomerular endothelial cell cultures. We have derived and qualified conditionally immortalized glomerular endothelial cells from glomerular outgrowths of the immortomouse. Our data illustrates that endothelin-1 protein expression is elevated in the endothelial cell compartment or hypertensive pre-proteinuric Alport mice relative to normotensive Alport mice (FIG. 27), suggesting that biomechanical stretching of glomerular endothelial cells induces endothelin-1 gene expression. Since glomerular endothelial cells are distinct from endothelial cells from the aorta or the umbilical veins, we will perform experiments to confirm that the pathway for stretch-induced gene expression is intact in our conditionally immortalized glomerular endothelial cell culture system. Based on preliminary evaluation of our conditionally immortalized cell cultures by real time RT-PCR, we know that they express the molecular machinery for this induction pathway (including TRPC3, ET-1, $ER_BR$, GC-A, protein kinase G and zyxin).

Cells will be differentiated for 2 weeks, serum starved, and plated on 6-well Flexcell plates pre-coated with rat tail collagen. Biomechanical stretching will be applied overnight using the Flexcell tension system (Flexcell International Corporation) as described in Example 1 (see also Meehan et al., 2009, Kidney Int; 76:968-976); and Zallocchi et al., 2013, Am J Pathol; 183(4):1269-80). RNA from these cells as well as cells treated identically but not subjected to biomechanical stretching will be analyzed by real time RT-PCR for expression of endothelin-1, Hey-1, VCAM-1 and IL-8 (all transcripts shown to be induced by stretching umbilical cord-derived primary human endothelial cells (HUVEC); (Wojtowicz et al., 2010, Circ Res; 107(7): 898-902). Primary HUVEC cell cultures will be used as a positive control in all experiments to assure that the conditions are conducive to induction of this gene set, and to determine whether the inhibitors, as applied in our system block induction of these same genes, as was previously described (Babu et al., 2012, Sci Signal; 5(254):ra91) Inhibitors for TRPC3 (Pyr3) and protein kinase G (Rp8) will be applied prior to stretching to assess the effect of these inhibitors on induction of the gene set. Protein kinase G phosphorylates zyxin, allowing it to dissociate from the plasma membrane focal adhesions and translocate to the nucleus where it activates expression of the zyxin responsive genes (Babu et al., 2012, Sci Signal; 5(254):ra91). In addition to the real time RT-PCR analysis, we will immunostain stretched and mock-stretched cells for all conditions with anti-zyxin antibodies to determine whether zyxin has translocated to the nucleus, consistent with its activation.

Preproteinuric X-linked Alport mice have very little GBM damage as determined by transmission electron microscopy, which predicts a thinner and less crosslinked GBM would result in the capillary tufts being more susceptible to biomechanical stretching than that of age/strain-matched wild type mice. Given the fact that pre-proteinuric Alport mice have elevated levels of endothelin-1 relative to age/strain-matched wild type mice (FIGS. 27-28), and that hypertensive Alport mice show further elevation of endothelin-1 expression, specifically in the endothelial cell compartment of the glomerulus (FIG. 27), we predict that the biomechanical stretching of cultured glomerular endothelial cells will result in the induction of the endothelin-1, Hey-1, VCAM-1 and IL-8 transcripts, as was observed and reported for both HUVECs and murine aortic endothelial cells (Wojtowicz et al., 2010, Circ Res; 107(7): 898-902; Babu et al., 2012, Sci Signal; 5(254):ra91). We also feel that is highly likely that the TRPC3/zyxin pathway is intact in these cells, since our conditionally immortalized glomerular endothelial cells express all of the requisite molecules and since we do not observe elevated expression of endothelin-1 in zyxin/COL4A5 double knockout mice relative to age/strain-matched wild type mice. It is likewise expected that the pre-incubation of cells with TRPC3 or protein kinase G inhibitors will, upon cyclic stretching, block the translocation of zyxin to the nucleus and block the induction of zyxin-responsive genes.

Specific Aim 2

Newly identified regulators are required for endothelin-1 mediated activation of CDC42 and subsequent formation of drebrin-positive actin microspikes in cultured mesangial cells. RNAseq analysis was performed on glomerular RNA from C57 Bl/6 wild type and X-linked Alport animals. 7 week-old animals were chosen because these animals are preproteinuric indicating a functionally intact GBM. We found that a number of genes were modulated (either up or down) in the Alport glomeruli relative to wild type. At least five of these genes, which were significantly induced in Alport glomeruli relative to wild type, are functionally linked to the activation pathway for CDC42. These include BMP-7 (bone morphogenetic protein-7) and its receptor BMP-RII, both of which have previously been shown to be expressed by mesangial cells (Yeh et al, 2009, Biochem Biophys Res Commun; 382(2):292-7), and four genes that are known to be implicated in the activation of CDC42 in other systems, but have never been described in the glomerulus or mesangial cells, including T cell differentiation protein 2 (MAL2) (Madrid et al., 2010, Dev Cell; 18(5): 814-27), golgi autoantigen, golgin subfamily a,2 (GM130) (Kodani et al., 2009, Mol Biol Cell; 20(4):1192-200), wingless-related MMTV integration site 11 (Wnt11) (Choe et al., 2013, Dev Cell; 24(3):296-309), and sortillin-related VPS10 domain containing receptor 2 (sorcs2) (Deinhardt et al., 2011, Sci Signal; 4(202):ra82). Interestingly, MAL2 and GM130 are involved in the trafficking of CDC42 to the plasma membrane, which is required for its activation (Madrid et al., 2010, Dev Cell; 18(5): 814-27; Kodani et al., 2009, Mol Biol Cell; 20(4):1192-200; Osmani et al., 2010, J Cell Biol; 191(7):1261-9). Real-time RT-PCR was performed using RNA from primary cultured mesangial cells to determine whether these newly identified glomerular transcripts are expressed in the mesangial cell compartment. The results demonstrated that all 6 transcripts linked to CDC42 activation and induced in Alport glomeruli from pre-proteinuric mice are abundantly (CT<30) expressed in the cultured mesangial cells.

The development of the in vitro bioassay for endothelin-mediated CD42 activation (FIG. 30) provides the platform for determining whether these genes are indeed linked to CDC42 activation in cultured mesangial cells. Transient SiRNA knockdown studies will be undertaken for each of the six newly identified genes. Following transfection with either gene-specific SiRNA or scrambled SiRNA, the cells will be incubated 24-48 hours, and then serum starved. Cells will then be stimulated with endothelin-1 and evaluate the cultures for the presence of cells with drebrin-positive actin-rich microspikes by dual staining with phalloidin and anti-drebrin antibodies. The cultures will be further evaluated for activated CDC42 using a commercially available ELISA assay as in FIG. 30. ELISA will be used as opposed to pull-down assays because the amount of material required for the latter is large, making this approach impractical. For the MAL2 and GM130 siRNA knockdowns (these proteins are implicated in the trafficking of CDC42 to the plasma membrane, which is a pre-requisite for activation, immunostaining with anti-CDC42 antibodies will determine whether the CDC42 is associated with the plasma membrane. As a control, we will knock down expression of the guanine nucleotide exchange factor, p21-activated kinase-interacting exchange factor (β1Pix), which has previously been shown required for the activation and membrane localization of CDC42.

Given that all 6 genes to be analyzed are induced very early in Alport glomerular pathogenesis, and that all of them are relatively abundant in cultured mesangial cells (CT values of 30 or less by real time RT-PCR), we expect them to be functionally important. Given the documentation in other cell systems that the proteins encoded by these genes are implicated in CDC42 activation, it is likely they play a role in this pathway in mesangial cells. Therefore we expect that we will find evidence that all or most of these proteins are indeed important in the activation of CDC42, identifying new aspects of this pathway that can be further explored in the mechanism of mesangial cell adhesion, migration, and filopodial formation, which has broader implications in the field of glomerular disease in addition to its importance in understanding the activation of filopodia formation in the onset of Alport glomerular disease.

Specific Aim 3

An endothelial cell-specific endothelin knockout Alport mouse will show arrested mesangial process invasion of the glomerular capillaries, preventing laminin 211-mediated FAK activation and ameliorating the initiation/progression of glomerular pathology. In the results discussed herein, we show that endothelin-1 is induced in glomeruli from pre-proteinuric Alport mice (FIGS. 27-28), but not wild type mice. We also show that mesangial cells express the endothelin A receptor, but not the endothelin B receptor (at least not within the detection limits of the methods used). As discussed in the previous example, Endothelin B receptors are the principal endothelin receptors found on glomerular endothelial cells and podocytes (see also Wendel et al., 2006, *J Histochem Cytochem;* 54(11):1193-203; Yamamoto et al., 2002, *Arch Histol Cytol;* 65(3):245-50). Blockade with endothelin A receptor antagonists was as effective as Bosentan at ameliorating glomerular and interstitial disease, which blocks both receptors, suggesting that the activation of actin cytoskeletal dynamics in the mesangial cell compartment occurs as a result of endothelin A receptor activation. Treatment of pre-proteinuric Alport mice with endothelin receptor blocking agents significantly reduced mesangial filopodial invasion of the glomerular capillaries, deposition of laminin 211 in the GBM, elevated expression of pro-pathogenic gene expression, delayed the onset and progression of proteinuria, and ameliorated the GBM dysmorphology (FIGS. 31-35).

As shown in FIG. 27, endothelin-1 is by far predominantly expressed in the glomerular endothelial cells. Earlier studies demonstrate that endothelin-1 secretion is highly regulated in glomerular endothelial cells, suggesting important homeostatic functions (Marsden et al., 1991; Babu et al., 2012, *Sci Signal;* 5(254):ra91). It has been speculated that endothelin-1 secreted by glomerular endothelial cells influences mesangial cell contractility and function (Simonson and Dunn, 1990, *J Clin Invest;* 85(3):790-7). Endothelin-1 knockout mice are not viable due to defects in the development of the heart and great vessels (Kurihara et al., 1995, *J Clin Invest;* 96(1):293-300). Interestingly, over expression of endothelin-1 causes late onset glomerulosclerosis, demonstrating that levels of endothelin-1 in healthy glomeruli are likely under tight homeostatic regulatory control (Hocher et al., 1997, *J Clin Invest;* 99(6):1380-9).

A direct way to test the role of endothelin-1 in mesangial process invasion of glomerular capillaries is to remove endothelin-1 expression from the system by way of genetic modeling. Given the lethality of the global knockout for EDN1, we will employ an endothelial cell-specific conditional knockout approach. This approach has been previously developed using the Tie2-Cre transgenic to drive endothelial cell-specific deletion of the floxed EDN1 gene (Kisanuki et al., 2010, *Hypertension;* 56(1):121-8). Importantly, these mice are found to be viable with no noted abnormalities, and have normal life spans, but interestingly lower blood pressure. This same paper documented complete deletion of endothelin-1 immunostaining in the glomerular endothelial cells of the Tie2-Cre (+) EDN1flox/flox mouse, providing proof of concept that this system will work for our purposes. The EDN1flox/flox mouse is also on the C57 Bl/6 background. These transgenics will be bred with the C57Bl/6 X-linked Alport knockout mouse to produce the endothelial cell-specific EDN1 knockout Alport mouse.

This approach will allow us to determine the extent of improved renal function that can be achieved by blocking endothelin receptor activation in Alport mesangial cells. In addition, by comparing hypertensive and hypotensive conditional EDN1 Alport mice we will be able to ascertain whether biomechanical strain results in other effects that promote Alport glomerular pathology that are independent of endothelin-1 mediated activation of glomerular mesangial cells. For instance, it has been shown that biomechanical stretching of glomerular podocytes activates angiotensin II receptors and increases expression of secreted protein acidic and rich in cysteine (SPARC) (see, for example, Durvasula and Shankland, 2005, *Am J Physiol Renal Physiol;* 289(3): F577-84). The former is associated with apoptosis, and the latter is associated with accelerated renal injury in diabetic mice. Thus, biomechanical stretching of podocytes has been shown to have some direct maladaptive effects on podocyte biology both in vivo and in vitro.

The experimental design strategy will consist of two different experiments. In the first we will compare the disease progression in wild type, EDN1 conditional KO, Alport, and EDN1 conditional KO Alport mice. All mice to be used in the study will be derived from the Tie2-Cre/Alport/EDN1flox/flox intercrosses. The first experiment will consist of one set of mice to be used for collection of time points, which will be collected at 5 week intervals starting at 5 weeks of age until 20 weeks of age (the mean lifespan for the X-linked Alport mouse model on this background is 25 weeks), and a second set of mice that will be used for longitudinal assessment of proteinuria, blood urea nitrogen levels, and lifespan. For the first set of mice, one kidney will be used for immunohistochemical analysis and transmission electron microscopy (TEM), and the other kidney will be used for RNA isolation by perfusion of glomeruli with magnetic Dynabeads. Glomerular RNA will be analyzed by real time RT-PCR for transcripts indicative of glomerular disease progression based on our earlier studies. These are essentially used as biomarkers since, as shown in Example 6, they are significantly induced in murine Alport glomeruli (see also Delimont et al., 2014, *PLoS One;* 9(6):e99083). These include MMP-10, MMP-12, MCP-1, and TGF-β1. Based on our experience with the mouse X-linked Alport mouse model, 5 animals per group will provide enough power to determine whether statistically significant differences exist in the expression of these genes when comparing groups. The five week intervals will provide information regarding the temporal kinetics of the therapeutic effect of EDN1 deletion. TEM analysis will provide an indication as to whether the EDN1 deletion improves the progression of the GBM damage and dysmorphology. Dual immunohistochemical staining for laminin α2/pFAK$^{397}$, laminin α2/laminin α5, and integrin α8/laminin α5 will provide evidence regarding the degree to which endothelial cell specific EDN1 deletion blocks mesangial filopodial invasion of the glomerular capillary loops, laminin 211 deposition in the GBM, and maladaptive pFAK activation in glomerular podocytes as a function of disease progression. The second experimental group will provide information on glomerular function (BUN/proteinuria) and will be conducted using methods are standardized in the laboratory. Lifespan will also be assessed, which will provide an indication as to the extent to which endothelin-1 receptor blockade might improve glomerular disease progression when fully optimized.

The second set of experiments are to define whether the effects of biomechanical strain are truly rooted in induction of endothelin-1 in glomerular endothelial cells (as shown in FIG. 8) and its effects on endothelin A receptor mediated activation of mesangial filopodial invasion of the glomerular capillaries (As shown in FIG. 34). Previously published work shows that we can markedly accelerate glomerular disease progression in Alport mice by making them hypertensive. These studies were the foundation of the hypothesis that the biomechanical properties of Alport GBM likely played a role in the mechanisms underlying glomerular pathogenesis. The conditional EDN1 knockout Alport mouse has a basement membrane collagen network comprised only of α1(IV)/α2(IV) chains, and thus the glomerular capillaries in pre-proteinuric mice are likely constantly subjected to abnormally high biomechanical stresses (a chronic insult that drives initiation and progression). The purpose of this experiment is to identify whether additional strain-dependent events occur that lie outside of the endothelin-1-mediated mesangial cell activation axis. Five animals per group as described above will be given L-NAME salts or regular water from 4 weeks until 10 weeks of age and blood pressure monitored once weekly using the CODA 2 tail cuff system. These ages are chosen based on our previously published findings, which demonstrate a clear influence of hypertension on glomerular disease progression within this time interval in the C57Bl/6 X-linked model (Meehan et al., 2009, *Kidney Int;* 76:968-976)). Urine will be collected at weekly intervals for proteinuria determination and blood will be collected at the termination of the experiment (10 weeks) for BUN measurements. One kidney will be used for RNA isolation and the other kidney for immunohistochemical analysis and TEM as for the first set of experiments. Analysis will be conducted as per above, with the exception that mRNA and immunohistochemistry will be conducted for SPARC expression, as this podocyte marker proved to be a reliable indicator of a biomechanical strain-mediated maladaptive podocyte-specific response in earlier work (Durvasula and Shankland, 2005, *Am J Physiol Renal Physiol;* 289(3):F577-84).

As shown in FIG. 27, endothelin A receptors are only detected on mesangial cells in the glomerulus (see also Wendel et al., 2006, *J Histochem Cytochem;* 54(11):1193-203), and the endothelin A receptor-specific antagonist Sitaxsenten ameliorates Alport glomerular disease progression at least as well as Bosentan, which blocks both endothelin A and B receptors. Based on these facts, we are confident that mesangial filopodial invasion results from paracrine activation of endothelin A receptors on mesangial cells by endothelial cell-derived endothelin-1. Endothelial cell-specific deletion of endothelin-1 should therefore produce a renoprotective phenotype similar to the endothelin A receptor blocking agent, Sitaxsentan. Since biomechanical stretching elevates expression of glomerular endothelial cell-derived endothelin-1, we predict that salt-mediated hypertension will not accelerate glomerular disease progression in the conditional EDN1 KO Alport mouse, but will accelerate progression in the Alport mouse. It is possible that hypertension will accelerate disease progression in the EDN1 conditional KO Alport mouse. If we observe this, along with elevated SPARC expression in the podocytes of these mice, we will interpret that to mean that stretch-mediated influences in the podocyte compartment may be a significant contributor to progression of Alport glomerular disease and explore this mechanism further.

Specific Aim 4

Dislocation of strain mediated induction of endothelin-1 by way of either TRPC3 or zyxin knockout will arrest endothelin induction and ameliorate mesangial process invasion of the glomerular capillaries, preventing laminin 211-mediated FAK activation and ameliorating the initiation/progression of Alport glomerular pathology, defining new targets for therapeutic intervention. Bosentan (endothelin A and B receptor blocker) and Ambrisentan (Endothelin A receptor-specific blocker, US trade name, LETAIRIS) are FDA approved drugs for the treatment of pulmonary hypertension. Both receptor blocking strategies have proven highly effective at reducing glomerular pathology and interstitial fibrosis in the Alport mouse model, as shown in the results described herein (we used Sitaxsenten as the endothelin A blocker because Ambrisentan was not available). Both were highly effective at ameliorating mesangial filopodial invasion and deposition of laminin 211 in the glomerular capillaries, and at reducing maladaptive regulation of MMPs and pro-inflammatory cytokines. These properties predict that endothelin receptor blockade (more specifically endothelin A receptor-specific blockade) may prove to be a promising new therapeutic approach for the treatment of Alport renal disease. One potential problem with this approach is that these drugs have a number of side effects. While acceptable for adults and children suffering from pulmonary hypertension, these side effects may preclude their use in children with Alport syndrome, since the therapy would continue in these patients for decades.

The purpose of this aim is to uncouple the mechanism of endothelin induction in glomerular endothelial cells using genetic modeling in order to reveal new potential targets for pharmacologic intervention. Biomechanical strain has been shown to induce the production and release of endothelin-1 in both astrocytes and endothelial cells (Hishikawa et al., 1995, *Hypertension;* 25(3):449-52; Ostrow et al., 2000, *J Cardiovasc Pharmacol;* 36(5 Suppl 1):S274-7). In endothelial cells, a major regulator of the mechanotransduction apparatus was found to be the LIM domain containing protein zyxin (Cattaruzza et al., 2004, *Circ Res;* 95(8):841-7). The zyxin protein is normally found at focal adhesions and translocates to the nucleus following a stretch-mediated phosphorylation event, where it acts as a transcription factor up-regulating pro-inflammatory gene expression, including endothelin-1 (Wojtowicz et al., 2010, *Circ Res;* 107(7):898-902). Recently it was shown that stretch-mediated activation of the transient receptor potential channel 3 (TRPC3) triggers a signaling cascade in endothelial cells culminating in the phosphorylation of zyxin, resulting in its release from focal adhesions and translocation to the nucleus (Babu et al., 2012, *Sci Signal;* 5(254):ra91). The authors demonstrated that this signaling cascade can be uncoupled at various points in vitro to block zyxin activation, and thus block stretch-mediated responses in endothelial cells.

The present approach will produce double knockout mice for the most upstream (TRPC3 activation) and downstream (zyxin activation) events in this cascade. Both zyxin and TRPC3 knockout mice are available from national repositories (MMRRC and Jackson Laboratories, respectively). Both of these knockout mice are fertile and have normal life spans. The TRPC3 mice show impaired walking behavior, presumably due to neurological effects. The zyxin knockout mice are on a pure C57Bl/6 background, and therefore can be readily bred to the X-linked Alport mouse model on this same background. The TRPC3 knockout mice are on a mixed 129 Sv/C57 Bl/6 background and thus will need to be backcrossed to C57 Bl/6 before a double knockout can be produced. This is critical as we know that strain-associated genetic modifiers exist that can profoundly affect renal disease progression which would surely introduce an unacceptable degree of variability on a mixed background.

The induction of endothelin-1 that we demonstrated in the endothelial cell compartment of hypertensive Alport mice relative to normotensive or hypotensive Alport mice (FIG. 27, N=4) combined with the demonstrated role for TRPC3 mediated activation of zyxin in this process would predict that endothelin mRNA and protein expression levels would be absent or normalized to basal (non-strain regulated) levels in both zyxin null and TRPC3 null Alport mice. As mentioned, we have already produced the zyxin/COL4A5 double knockout mouse model, and observed very low levels of endothelin-1 expression in this model, consistent with our earlier assumptions, and providing strong support for this approach. All experimental animals will be derived from intercrosses for each double knockout mouse model. We will examine wild type, Alport, TRPC3 or zyxin KO, and TRPC3 KO/Alport or zyxin KO Alport mice. Animals will be treated with Ramipril or L-NAME salts from 4 weeks until 10 weeks of age with blood pressures monitored once a week. Glomeruli will be isolated from one kidney for analysis of endothelin mRNA and protein by real time RT-PCR and western blot. Expression levels of MMP-10, MMP-12, and MCP-1 RNA will also be examined (based on preliminary data with endothelin receptor blockers). The other kidney will be examined by TEM for GBM dysmorphology and by immunohistochemistry for GBM laminin 211 deposition, podocyte FAK activation (pFAK397 immunostaining) and mesangial interposition by integrin α8 immunostaining.

A second set of experiments will be conducted specifically as outlined for Aim 1, where we will examine proteinuria, BUN and lifespan on one set of animals and the kinetics of disease progression at 5, 10, 15 and 20 weeks of age in the second set of animals.

Based on the published findings linking stretch mediated TRPC3 activation to zyxin activation in endothelial cell mechanotransduction (Babu et al., 2012, *Sci Signal;* 5(254): ra91) we feel confident that the gene deletions will ameliorate glomerular disease progression in the Alport mouse model. The fact that we observe elevated expression of endothelin-1 in the endothelial cells of Alport mice as well as the observation that hypertension further elevates the expression of endothelin-1 infers that this strain-regulated pathway is activated in our model. If true, deletion of either TRPC3 or zyxin should short circuit this signaling pathway resulting in the absence of elevated endothelin-1 expression in the glomerular endothelial cells and the amelioration of endothelin-mediated influences, including abrogation of mesangial filopodial invasion of the glomerular capillaries, deposition of laminin 211 in the GBM, and activation of FAK in Alport podocytes. To date, we have confirmed that 7 week old (preproteinuric) zyxin/COL4A5 double knockout mice express low levels of endothelin-1 relative to age/strain matched COL4A5 null mice, consistent with our central hypothesis. In the work described by Wojtowicz et al. (Wojtowicz et al., 2010, *Circ Res;* 107(7): 898-902), global gene expression analysis of stretched endothelial cells demonstrated that stretch mainly activated genes involved in pro-inflammatory pathways. Based on this, we might expect that these double knockout mice could be more effective at preventing the onset and/or progression of glomerular disease than the conditional knockout of endothelin-1 (Aim 3) or endothelin blockade with small molecule inhibitors (preliminary results). If this scenario is observed, it would suggest that therapeutic approaches aimed at this strain-responsive signaling cascade might provide superior renoprotection in Alport patients compared to endothelin blockade alone, warranting the development of new drugs that target this pathway. It is notable that endothelin receptor blockade by either Bosentan or Ambrisentan, while FDA approved for pulmonary fibrosis, might be considered toxic for use in young boys with Alport syndrome. This fact provides justification for exploring alternative means of targeting the strain-mediated regulation of endothelin-1 in Alport syndrome.

Example 7

Neutralizing Antibodies to Endothelin-1

Following procedures described in the previous examples, the effect of neutralizing antibodies to endothelin-1 or the endothelin receptor will be tested for their ability to prevent mesangial filopodial invasion of glomerular capillaries and delay Alport glomerular and interstitial disease onset.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of inhibiting Alport pathogenesis in a subject, the method comprising administering to the subject an effective amount of an antibody that specifically binds endothelin-1 and neutralizes one or more functions of endothelin-1.

2. A method of inhibiting Alport pathogenesis in a subject, the method comprising administering an effective amount of an antibody against endothelin 1 to the subject.

3. The method of claim 2, wherein the antibody against endothelin-1 or derivative thereof neutralizes one or more functions of endothelin-1.

4. The method of claim 2, wherein glomerular disease progression is inhibited.

5. The method of claim 2, wherein glomerulonephritis is treated.

6. The method of claim 2, wherein deposition of laminin 211 in the glomerular basement membrane (GBM) is inhibited.

7. The method of claim 2, wherein mesangial cell process invasion of the glomerular capillary loop in a kidney is inhibited.

8. The method of claim 2, wherein one or more sensory and/or hearing losses associated with Alport syndrome is treated or prevented.

9. The method of claim 2; the method further comprising determining that the subject is at risk for developing Alport glomerular disease.

10. The method of claim 9, wherein the determination that the subject is at risk for developing Alport glomerular disease is determined by family medical history, genetic testing, immunodiagnostic skin biopsy testing, and/or molecular diagnostic marker testing.

11. The method of claim 9, wherein the determination that the subject is at risk for developing Alport glomerular disease is made prior to the onset of proteinuria in the subject.

12. The method of claim 2, wherein the administration of an effective amount of an antibody against endothelin 1 is initiated prior to the onset of proteinuria in the subject.

* * * * *

UNITED STATES PATENT AND TRADEMARK OFFICE
CERTIFICATE OF CORRECTION

PATENT NO. : 9,719,981 B2  
APPLICATION NO. : 14/580680  
DATED : August 1, 2017  
INVENTOR(S) : Dominic Cosgrove Page 1 of 1

It is certified that error appears in the above-identified patent and that said Letters Patent is hereby corrected as shown below:

In the Claims

Column 59, Line 2: Please delete "or derivative thereof"

Signed and Sealed this  
Tenth Day of April, 2018

Andrei Iancu  
*Director of the United States Patent and Trademark Office*